US012599323B2

(12) United States Patent
Joo et al.

(10) Patent No.: US 12,599,323 B2
(45) Date of Patent: *Apr. 14, 2026

(54) METHODS AND SYSTEMS FOR TREATING PREGNANCY-RELATED HYPERTENSIVE DISORDERS COMPRISING ANTI-sEng AND ANTI-sFlt-1 ANTIBODIES

(71) Applicant: Aggamin, LLC, New York, NY (US)

(72) Inventors: Woo S. Joo, Gaithersburg, MD (US);
Karen M. Lee, Massapequa, NY (US);
Adelene Y. Tan, New York, NY (US);
Garrett D. Daniels, Mamaroneck, NY
(US); Paul Kussie, New York, NY (US)

(73) Assignee: Aggamin, LLC, New York, NY (US)

( * ) Notice: Subject to any disclaimer, the term of this patent is extended or adjusted under 35 U.S.C. 154(b) by 980 days.

This patent is subject to a terminal disclaimer.

(21) Appl. No.: 17/783,801

(22) PCT Filed: Dec. 8, 2020

(86) PCT No.: PCT/US2020/063707
§ 371 (c)(1),
(2) Date: Jun. 9, 2022

(87) PCT Pub. No.: WO2021/118957
PCT Pub. Date: Jun. 17, 2021

(65) Prior Publication Data
US 2023/0056992 A1 Feb. 23, 2023

Related U.S. Application Data

(60) Provisional application No. 62/947,821, filed on Dec. 13, 2019.

(51) Int. Cl.
*A61P 9/12* (2006.01)
*A61B 5/15* (2006.01)
*C07K 16/28* (2006.01)

(52) U.S. Cl.
CPC .................. *A61B 5/15* (2013.01); *A61P 9/12* (2018.01); *C07K 16/2863* (2013.01)

(58) Field of Classification Search
None
See application file for complete search history.

(56) References Cited

U.S. PATENT DOCUMENTS

| | | | |
|---|---|---|---|
| 7,740,849 B2 * | 6/2010 | Karumanchi | ...... A61K 38/1841 424/139.1 |
| 9,592,331 B2 * | 3/2017 | Kussie | .................... A61M 1/34 |
| 2014/0065150 A1 | 3/2014 | Kussie et al. | |
| 2015/0330989 A1 | 11/2015 | Burwick et al. | |
| 2017/0072018 A1 | 3/2017 | Karumanchi et al. | |
| 2017/0355771 A1 | 12/2017 | Salas et al. | |

FOREIGN PATENT DOCUMENTS

WO 2017189964 A2 11/2017

OTHER PUBLICATIONS

Ives et al., J Am Coll Cardiol. 2020; 76: 1690-1702 (Year: 2020).*
Cleveland Clinic website: https://my.clevelandclinic.org/health/diseases/21637-hellp-syndrome; downloaded Jun. 9, 2025 (Year: 2025).*

* cited by examiner

*Primary Examiner* — Christina M Borgeest
(74) *Attorney, Agent, or Firm* — Fox Rothschild LLP

(57) ABSTRACT

Disclosed are methods and apparatuses for treating a pregnancy related hypertensive disorder, such as pre-eclampsia and eclampsia, using ex vivo treatment with an anti-sFlt-1 antibody and an anti-sEng antibody bound to a solid support in order to reduce blood levels of sFlt-1 and sEng. The present disclosure relates to methods, systems, devices, and apparatuses for treating pregnancy-related hypertensive disorders such as pre-eclampsia and eclampsia.

25 Claims, 4 Drawing Sheets
Specification includes a Sequence Listing.

SEQUENCE LISTING

```
<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: CDR1H of AG10B

<400> SEQUENCE: 1

Gly Tyr Thr Phe Thr Asp Tyr Val Ile Ser
1               5                   10

<210> SEQ ID NO 2
<211> LENGTH: 20
<212> TYPE: PRT
<213> ORGANISM: Artificial Sequence
<220> FEATURE:
<223> OTHER INFORMATION: CDR2H of AG10B

<400> SEQUENCE: 2

Trp Ile Gly Glu Ile Tyr Pro Gly Ser Gly Ser Ile Tyr Tyr Asn Glu
1               5                   10                  15

Lys Phe Lys Gly
            20

<210> SEQ ID NO 3
<211> LENGTH: 9
<212> TYPE: PRT
<213> ORGANISM: Artificial Sequence
<220> FEATURE:
<223> OTHER INFORMATION: CDR3H of AG10B

<400> SEQUENCE: 3
```

-continued

```
Gly His Tyr Tyr Gly Tyr Phe Asp Tyr
1               5

<210> SEQ ID NO 4
<211> LENGTH: 13
<212> TYPE: PRT
<213> ORGANISM: Artificial Sequence
<220> FEATURE:
<223> OTHER INFORMATION: CDR1L of AG10B

<400> SEQUENCE: 4

Lys Ala Ser Gln Asp Val Thr Ile Thr Val Ala Trp Tyr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: CDR2L of AG10B

<400> SEQUENCE: 5

Leu Leu Ile Tyr Ser Ala Ser Tyr Arg Tyr Thr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: CDR3L of AG10B

<400> SEQUENCE: 6

Gln Gln His Tyr Thr Thr Pro Trp Thr
1               5

<210> SEQ ID NO 7
<211> LENGTH: 10
<212> TYPE: PRT
<213> ORGANISM: Artificial Sequence
<220> FEATURE:
<223> OTHER INFORMATION: CDR1H of cENG10

<400> SEQUENCE: 7

Gly Tyr Thr Ile Thr Glu His Thr Leu His
1               5                   10

<210> SEQ ID NO 8
<211> LENGTH: 17
<212> TYPE: PRT
<213> ORGANISM: Artificial Sequence
<220> FEATURE:
<223> OTHER INFORMATION: CDR2H of cENG10

<400> SEQUENCE: 8

Gly Ile Asn Phe Asp Asn Gly Gly Thr Thr Tyr Arg Gln Lys Phe Lys
1               5                   10                  15

Asp

<210> SEQ ID NO 9
<211> LENGTH: 11
<212> TYPE: PRT
<213> ORGANISM: Artificial Sequence
<220> FEATURE:
<223> OTHER INFORMATION: CDR3H of cENG10
```

<400> SEQUENCE: 9

Arg Ala Tyr Tyr Tyr Gly Ser Ala Phe Asp Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: CDR1L of cENG10

<400> SEQUENCE: 10

Arg Ala Ser Ser Ser Val Asn Tyr Val Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CDR2L of cENG10

<400> SEQUENCE: 11

Tyr Thr Ser Asn Leu Ala Pro
1               5

<210> SEQ ID NO 12
<211> LENGTH: 9
<212> TYPE: PRT
<213> ORGANISM: Artificial Sequence
<220> FEATURE:
<223> OTHER INFORMATION: CDR3L of cENG10

<400> SEQUENCE: 12

Gln Gln Phe Ile Ser Phe Pro Tyr Thr
1               5

<210> SEQ ID NO 13
<211> LENGTH: 354
<212> TYPE: DNA
<213> ORGANISM: Artificial Sequence
<220> FEATURE:
<223> OTHER INFORMATION: Nucleotide sequence of chimeric anti-sFlt-1
      antibody AG10B variable domain of heavy chain (VH) (without leader
      sequence)

<400> SEQUENCE: 13
caggttcagc tgcagcagtc tggacctgag ctggtgaagc ctgggggcttc agtgaagatg        60 tcctgcaagg cttctggata cacattcact gactatgtta taagttgggt gaaacagaga       120
actggacagg gccttgagtg gattggagag atttatcctg gaagtggtag tatttactac       180
aatgagaagt tcaagggcaa ggccacactg actgcagaca tcctccaa cacagcctac        240 atgcagctca gcagcctgac atttgaggac tctgcggtca ttttctgtgc aagagggcat       300
tattacggtt actttgacta ctggggccaa ggcaccactc tcacagtctc ctca            354

<210> SEQ ID NO 14
<211> LENGTH: 118
<212> TYPE: PRT
<213> ORGANISM: Artificial Sequence
<220> FEATURE:
<223> OTHER INFORMATION: Amino acid sequence of chimeric anti-sFlt-1
      antibody AG10B variable domain of heavy chain (VH) (without leader
      sequence)

<400> SEQUENCE: 14

-continued

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Ile Tyr Tyr Asn Glu Lys Phe
    50                  55                  60

Lys Gly Lys Ala Thr Leu Thr Ala Asp Thr Ser Ser Asn Thr Ala Tyr
65                  70                  75                  80

Met Gln Leu Ser Ser Leu Thr Phe Glu Asp Ser Ala Val Ile Phe Cys
                85                  90                  95

Ala Arg Gly His Tyr Tyr Gly Tyr Phe Asp Tyr Trp Gly Gln Gly Thr
            100                 105                 110

Thr Leu Thr Val Ser Ser
        115
```

```
<210> SEQ ID NO 15
<211> LENGTH: 321
<212> TYPE: DNA
<213> ORGANISM: Artificial Sequence
<220> FEATURE:
<223> OTHER INFORMATION: Nucleotide sequence of chimeric anti-sFlt-1
      antibody AG10B variable domain of light chain (VL) (without leader
      sequence)

<400> SEQUENCE: 15
gacattgtga tgacccagtc tcacaaattc atgtccacat cagtaggaga cagggtcagc          60
atcacctgca aggccagtca ggatgtgact attactgtag cctggtatca acagaaacca         120
ggacaatctc ctaaacttct gatttactcg gcatcctacc ggtacactgg agtccctgat         180
cgcttcactg gcagtggatc tgggacggat ttcactttca ccatcagcag tgtgcaggct         240
gaagacctgg cagtttatta ctgtcagcaa cattatacta ctccgtggac gttcggtgga         300
ggcaccaagc tggaaatcaa a                                                   321
```

```
<210> SEQ ID NO 16
<211> LENGTH: 107
<212> TYPE: PRT
<213> ORGANISM: Artificial Sequence
<220> FEATURE:
<223> OTHER INFORMATION: Amino acid sequence of chimeric anti-sFlt-1
      antibody AG10B variable domain of light chain (VL) (without leader
      sequence)

<400> SEQUENCE: 16

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Ile Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Trp
                85                  90                  95
```

Thr Phe Gly Gly Gly Thr Lys Leu Glu Ile Lys
            100                 105

<210> SEQ ID NO 17
<211> LENGTH: 1401
<212> TYPE: DNA
<213> ORGANISM: Artificial Sequence
<220> FEATURE:
<223> OTHER INFORMATION: Nucleotide sequence of chimeric anti-sFlt-1
      antibody AGB10 heavy chain

<400> SEQUENCE: 17
atgatgtcct ttgtctctct gctcctggta ggcatcctat tccatgccac ccaggcccag      60
gttcagctgc agcagtctgg acctgagctg gtgaagcctg gggcttcagt gaagatgtcc     120
tgcaaggctt ctggatacac attcactgac tatgttataa gttgggtgaa acagagaact     180
ggacagggcc ttgagtggat tggagagatt tatcctggaa gtggtagtat ttactacaat     240
gagaagttca gggcaaggc cacactgact gcagacacat cctccaacac agcctacatg     300
cagctcagca gcctgacatt tgaggactct gcggtcattt tctgtgcaag agggcattat     360
tacggttact ttgactactg gggccaaggc accactctca cagtctcctc agctagcacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga gagttgagcc caaatcttgt     720
gacaaaactc acacatgccc accgtgccca gcacctgaac tcctgggggg accgtcagtc     780
ttcctcttcc cccaaaaacc caaggacacc ctcatgatct cccggacccc tgaggtcaca     840
tgcgtggtgg tggacgtgag ccacgaagac cctgaggtca agttcaactg gtatgtggac     900
ggcgtggagg tgcataatgc caagacaaag ccgcgggagg agcagtacca aagcacgtac     960
cgtgtggtca gcgtcctcac cgtcctgcac caagactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggagga gatgaccaag    1140
aaccaagtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta ttccaagctc accgtggaca gagcaggtg gcagcagggg    1320 aacgtcttct catgctccgt gatgcatgag gctctgcaca accactacac gcagaagagc    1380
ctctccctgt ctccgggctg a                                             1401

<210> SEQ ID NO 18
<211> LENGTH: 360
<212> TYPE: PRT
<213> ORGANISM: Artificial Sequence
<220> FEATURE:
<223> OTHER INFORMATION: Amino acid sequence of chimeric anti-sFlt-1
      antibody AGB10 heavy chain

<400> SEQUENCE: 18

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

-continued

```
Val Ile Ser Trp Val Lys Gln Arg Thr Gly Gln Gly Leu Glu Trp Ile
    35                  40                  45

Gly Glu Ile Tyr Pro Gly Ser Gly Ser Ile Tyr Tyr Asn Glu Lys Phe
    50                  55                  60

Lys Gly Lys Ala Thr Leu Thr Ala Asp Thr Ser Ser Asn Thr Ala Tyr
65                  70                  75                  80

Met Gln Leu Ser Ser Leu Thr Phe Glu Asp Ser Ala Val Ile Phe Cys
                85                  90                  95

Ala Arg Gly His Tyr Tyr Gly Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr
        355                 360
```

<210> SEQ ID NO 19
<211> LENGTH: 702
<212> TYPE: DNA
<213> ORGANISM: Artificial Sequence
<220> FEATURE:
<223> OTHER INFORMATION: Nucleotide sequence of chimeric anti-sFlt-1
      antibody AGB10 light chain

<400> SEQUENCE: 19
atgatgtcct ttgtctctct gctcctggta ggcatcctat tccatgccac ccaggccgac      60
attgtgatga cccagtctca caaattcatg tccacatcag taggagacag ggtcagcatc     120
acctgcaagg ccagtcagga tgtgactatt actgtagcct ggtatcaaca gaaaccagga     180

```
caatctccta aacttctgat ttactcggca tcctaccggt acactggagt ccctgatcgc      240
ttcactggca gtggatctgg gacggatttc actttcacca tcagcagtgt gcaggctgaa      300
gacctggcag tttattactg tcagcaacat tatactactc cgtggacgtt cggtggaggc      360
accaagctgg aaatcaaacg gactgtggct gcaccatctg tcttcatctt cccgccatct      420
gatgagcagt tgaaatctgg aactgcctct gttgtgtgcc tgctgaataa cttctatccc      480
agagaggcca agtacagtg gaaggtggat aacgccctcc aatcgggtaa ctcccaggag      540
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgtt ag                         702
```

```
<210> SEQ ID NO 20
<211> LENGTH: 214
<212> TYPE: PRT
<213> ORGANISM: Artificial Sequence
<220> FEATURE:
<223> OTHER INFORMATION: Amino acid sequence of chimeric anti-sFlt-1
      antibody AGB10 light chain

<400> SEQUENCE: 20

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Ile Thr
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 21
<211> LENGTH: 360
<212> TYPE: DNA
<213> ORGANISM: Artificial Sequence
<220> FEATURE:
<223> OTHER INFORMATION: Nucleotide sequence of chimeric anti-sEng
```

-continued antibody cENG10 variable domain of heavy chain (VH) (without
    leader sequence)

<400> SEQUENCE: 21
gaggtccagc tggaacagtc tggacctgaa gtggtgaagc ctgggacttc agtgaagata    60
tcctgcaaga cttctggata cacaatcact gaacacacct tgcactggat aaagcagaac   120
cagggaaaga gccttgagtg gattggtggt attaattttg acaatggtgg tactacctac   180
aggcagaaat tcaaggacaa ggccacattg actgtggaca gtcctccag cacagccttc     240 atggagctcc gcagcctgac ttctgatgat tctgcagtct atttctgcgc aagaagggcc   300
tattactacg gtagtgcctt tgactactgg ggccaaggca ccactctcac agtctcctca   360

<210> SEQ ID NO 22
<211> LENGTH: 120
<212> TYPE: PRT
<213> ORGANISM: Artificial Sequence
<220> FEATURE:
<223> OTHER INFORMATION: Amino acid sequence of chimeric anti-sEng
    antibody cENG10 variable domain of heavy chain (VH) (without
    leader sequence)

<400> SEQUENCE: 22

Glu Val Gln Leu Glu Gln Ser Gly Pro Glu Val Val Lys Pro Gly Thr
1               5                   10                  15

Ser Val Lys Ile Ser Cys Lys Thr Ser Gly Tyr Thr Ile Thr Glu His
            20                  25                  30

Thr Leu His Trp Ile Lys Gln Asn Gln Gly Lys Ser Leu Glu Trp Ile
        35                  40                  45

Gly Gly Ile Asn Phe Asp Asn Gly Gly Thr Thr Tyr Arg Gln Lys Phe
    50                  55                  60

Lys Asp Lys Ala Thr Leu Thr Val Asp Lys Ser Ser Ser Thr Ala Phe
65                  70                  75                  80

Met Glu Leu Arg Ser Leu Thr Ser Asp Asp Ser Ala Val Tyr Phe Cys
                85                  90                  95

Ala Arg Arg Ala Tyr Tyr Tyr Gly Ser Ala Phe Asp Tyr Trp Gly Gln
            100                 105                 110

Gly Thr Thr Leu Thr Val Ser Ser
        115                 120

<210> SEQ ID NO 23
<211> LENGTH: 318
<212> TYPE: DNA
<213> ORGANISM: Artificial Sequence
<220> FEATURE:
<223> OTHER INFORMATION: Nucleotide sequence of chimeric anti-sEng
    antibody cENG10 variable domain of light chain (VL) (without
    leader sequence)

<400> SEQUENCE: 23
gaaaatgtgc tcacccagtc tccagcaatc atgtctgcat ctctagggga gaaggtcacc    60
atgacctgca gggccagctc aagtgtgaat tacgtgtact ggtaccagca gaagtcagat   120
gcctccccca aactatggat ttattacact tccaacctgg ctcctggagt cccagctcgc   180
ttcagtggca gtgggtctgg gaactcttat tctctcacaa tcagcagcat ggaggtgaa    240 gatgctgcca cttattactg ccagcagttt attagtttcc catacacgtt cggagggggg   300
accaagctgg aaataaaa                                                  318

<210> SEQ ID NO 24

-continued

```
<211> LENGTH: 106
<212> TYPE: PRT
<213> ORGANISM: Artificial Sequence
<220> FEATURE:
<223> OTHER INFORMATION: Amino acid sequence of chimeric anti-sEng
      antibody cENG10 variable domain of light chain (VL) (without
      leader sequence)

<400> SEQUENCE: 24

Glu Asn Val Leu Thr Gln Ser Pro Ala Ile Met Ser Ala Ser Leu Gly
1               5                   10                  15

Glu Lys Val Thr Met Thr Cys Arg Ala Ser Ser Ser Val Asn Tyr Val
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ile Ser Phe Pro Tyr Thr
                85                  90                  95

Phe Gly Gly Gly Thr Lys Leu Glu Ile Lys
            100                 105

<210> SEQ ID NO 25
<211> LENGTH: 1407
<212> TYPE: DNA
<213> ORGANISM: Artificial Sequence
<220> FEATURE:
<223> OTHER INFORMATION: Nucleotide sequence of chimeric anti-sEng
      antibody cENG10 heavy chain

<400> SEQUENCE: 25
atgggatggt catgtatcat cctttttcta gtagcaactg caactggagt acattcagag      60
gtccagctgg aacagtctgg acctgaagtg gtgaagcctg ggacttcagt gaagatatcc     120
tgcaagactt ctggatacac aatcactgaa cacaccttgc actggataaa gcagaaccag     180
ggaaagagcc ttgagtggat tggtggtatt aattttgaca atggtggtac tacctacagg     240
cagaaattca aggacaaggc cacattgact gtggacaagt cctccagcac agccttcatg     300
gagctccgca gcctgacttc tgatgattct gcagtctatt tctgcgcaag aagggcctat     360
tactacggta gtgcctttga ctactggggc caaggcacca ctctcacagt cctcagcct      420 agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagagagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtat     900
gtggacggcg tggaggtgca taatgccaag acaaagccgc gggaggagca gtaccaaagc     960
acgtaccgtg tggtcagcgt cctcaccgtc ctgcaccaag actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
```

-continued

```
accaagaacc aagtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctattcc aagctcaccg tggacaagag caggtggcag    1320
caggggaacg tcttctcatg ctccgtgatg catgaggctc tgcacaacca ctacacgcag    1380
aagagcctct ccctgtctcc gggctga                                       1407

<210> SEQ ID NO 26
<211> LENGTH: 449
<212> TYPE: PRT
<213> ORGANISM: Artificial Sequence
<220> FEATURE:
<223> OTHER INFORMATION: Amino acid sequence of chimeric anti-sEng
      antibody cENG10 heavy chain

<400> SEQUENCE: 26

Glu Val Gln Leu Glu Gln Ser Gly Pro Glu Val Val Lys Pro Gly Thr
1               5                   10                  15

Ser Val Lys Ile Ser Cys Lys Thr Ser Gly Tyr Thr Ile Thr Glu His
            20                  25                  30

Thr Leu His Trp Ile Lys Gln Asn Gln Gly Lys Ser Leu Glu Trp Ile
        35                  40                  45

Gly Gly Ile Asn Phe Asp Asn Gly Gly Thr Thr Tyr Arg Gln Lys Phe
    50                  55                  60

Lys Asp Lys Ala Thr Leu Thr Val Asp Lys Ser Ser Ser Thr Ala Phe
65                  70                  75                  80

Met Glu Leu Arg Ser Leu Thr Ser Asp Asp Ser Ala Val Tyr Phe Cys
                85                  90                  95

Ala Arg Arg Ala Tyr Tyr Tyr Gly Ser Ala Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300
```

-continued

```
Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
        355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly
```

```
<210> SEQ ID NO 27
<211> LENGTH: 699
<212> TYPE: DNA
<213> ORGANISM: Artificial Sequence
<220> FEATURE:
<223> OTHER INFORMATION: Nucleotide sequence of chimeric anti-sEng
      antibody cENG10 light chain

<400> SEQUENCE: 27
atgggatggt catgtatcat ccttttttcta gtagcaactg caactggagt acattcagaa      60
aatgtgctca cccagtctcc agcaatcatg tctgcatctc tagggggagaa ggtcaccatg     120 acctgcaggg ccagctcaag tgtgaattac gtgtactggt accagcagaa gtcagatgcc     180
tcccccaaac tatggattta ttacacttcc aacctggctc ctggagtccc agctcgcttc     240
agtggcagtg ggtctgggaa ctcttattct ctcacaatca gcagcatgga gggtgaagat     300
gctgccactt attactgcca gcagtttatt agtttcccat acacgttcgg aggggggacc     360
aagctggaaa taaaacggac tgtggctgca ccatctgtct tcatcttccc gccatctgat     420
gagcagttga aatctggaac tgcctctgtt gtgtgcctgc tgaataactt ctatcccaga     480
gaggccaaag tacagtggaa ggtggataac gccctccaat cgggtaactc ccaggagagt     540
gtcacagagc aggacagcaa ggacagcacc tacagcctca gcagcaccct gacgctgagc     600
aaagcagact acgagaaaca caaagtctac gcctgcgaag tcacccatca gggcctgagc     660
tcgcccgtca caaagagctt caacagggga gagtgttag                             699
```

```
<210> SEQ ID NO 28
<211> LENGTH: 213
<212> TYPE: PRT
<213> ORGANISM: Artificial Sequence
<220> FEATURE:
<223> OTHER INFORMATION: Amino acid sequence of chimeric anti-sEng
      antibody cENG10 light chain

<400> SEQUENCE: 28

Glu Asn Val Leu Thr Gln Ser Pro Ala Ile Met Ser Ala Ser Leu Gly
1               5                   10                  15

Glu Lys Val Thr Met Thr Cys Arg Ala Ser Ser Ser Val Asn Tyr Val
```

-continued

```
            20                    25                    30

Tyr Trp Tyr Gln Gln Lys Ser Asp Ala Ser Pro Lys Leu Trp Ile Tyr
        35                    40                    45

Tyr Thr Ser Asn Leu Ala Pro Gly Val Pro Ala Arg Phe Ser Gly Ser
    50                    55                    60

Gly Ser Gly Asn Ser Tyr Ser Leu Thr Ile Ser Ser Met Glu Gly Glu
65                    70                    75                    80

Asp Ala Ala Thr Tyr Tyr Cys Gln Gln Phe Ile Ser Phe Pro Tyr Thr
                85                    90                    95

Phe Gly Gly Gly Thr Lys Leu Glu Ile Lys Arg Thr Val Ala Ala Pro
                100                   105                   110

Ser Val Phe Ile Phe Pro Pro Ser Asp Glu Gln Leu Lys Ser Gly Thr
        115                   120                   125

Ala Ser Val Val Cys Leu Leu Asn Asn Phe Tyr Pro Arg Glu Ala Lys
    130                   135                   140

Val Gln Trp Lys Val Asp Asn Ala Leu Gln Ser Gly Asn Ser Gln Glu
145                   150                   155                   160

Ser Val Thr Glu Gln Asp Ser Lys Asp Ser Thr Tyr Ser Leu Ser Ser
                165                   170                   175

Thr Leu Thr Leu Ser Lys Ala Asp Tyr Glu Lys His Lys Val Tyr Ala
                180                   185                   190

Cys Glu Val Thr His Gln Gly Leu Ser Ser Pro Val Thr Lys Ser Phe
                195                   200                   205

Asn Arg Gly Glu Cys
        210
```

METHODS AND SYSTEMS FOR TREATING PREGNANCY-RELATED HYPERTENSIVE DISORDERS COMPRISING ANTI-sEng AND ANTI-sFlt-1 ANTIBODIES

CROSS REFERENCE TO RELATED APPLICATIONS

This application is a national stage patent application of International Patent Application No. PCT/US20/63707, filed on Dec. 8, 2020, which claims priority to U.S. Provisional Application No. 62/947,821, filed on Dec. 13, 2019; both of which are hereby incorporated by reference in their entireties.

STATEMENT REGARDING FEDERALLY SPONSORED RESEARCH OR DEVELOPMENT

This invention was made with government support under grant number R44 HD 075571 awarded by National Institute of Child Health and Human Development (NICHD). The government has certain rights in the invention.

REFERENCE TO A SEQUENCE LISTING

This application contains a Sequence Listing, which has been submitted electronically in text format and is hereby incorporated by reference in its entirety. Said txt copy, created on Dec. 4, 2020, is named 163173-46376_ST25-Seq-Listing.txt and is 27,991 bytes in size.

FIELD OF THE INVENTION

The present disclosure relates to methods, systems, devices, and apparatuses for treating pregnancy-related hypertensive disorders such as pre-eclampsia and eclampsia.

BACKGROUND

Pre-eclampsia is a syndrome of hypertension, edema, and proteinuria that affects 5 to 10% of pregnancies and results in substantial maternal and fetal morbidity and mortality. Pre-eclampsia accounts for at least 63,000 maternal deaths worldwide per year. The symptoms of pre-eclampsia typically appear after the $20^{th}$ week of pregnancy and are usually detected by the routine monitoring of blood pressure and protein levels in urine. However, these monitoring methods are ineffective for diagnosis of pre-eclampsia at an early stage, which could reduce the risk to the subject or developing fetus, if an effective treatment were available.

Symptoms of pre-eclampsia generally include any of the following: (1) a systolic blood pressure (BP)>140 mmHg and a diastolic BP>90 mmHg after 20 weeks gestation, (2) new onset proteinuria (1+ by dipstick on urinalysis, >300 mg of protein in a 24 hour urine collection, or random urine protein/creatinine ratio>0.3), or (3) new-onset hypertension with new-onset of any of the following: thrombocytopenia, renal insufficiency, impaired liver function, pulmonary edema, cerebral/visual symptoms. The symptoms of pre-eclampsia can also include renal dysfunction and glomerular endotheliosis or hypertrophy. Other symptoms of eclampsia may be any of the following symptoms due to pregnancy or the influence of a recent pregnancy: seizures, coma, thrombocytopenia, liver edema, pulmonary edema, or cerebral edema. Women with pre-eclampsia are further at risk of developing HELLP syndrome, which is characterized by hemolysis (H, the breakdown of red blood cells), elevated liver enzymes (EL), and low platelet count (LP).

Pre-eclampsia can vary in severity from mild to life threatening. A mild form of pre-eclampsia may be treated with bed rest and frequent monitoring. For moderate to severe cases, hospitalization is recommended and blood pressure medications or anticonvulsant medications to prevent seizures are prescribed. If the condition becomes life threatening to the mother or the fetus, the pregnancy is terminated and the fetus is delivered pre-term.

Currently, the availability of effective therapies for pre-eclampsia or eclampsia is severely limited. Premature delivery saves the mother but poses significant risks to newborns. The current standard of care is to monitor and to manage maternal symptoms. Magnesium sulfate is given to prevent seizure. Antihypertensives such as hydralazine, nicardipine, nifedipine, and β-blockers are used as emergency treatment in severe cases, but using these drugs can cause hypotension and other side effects. These small-molecule compounds can cross the placental barrier and pose direct risks to the fetus. Importantly, none of these drugs target the underlying causes of pre-eclampsia. Given the limited effectiveness of the current standard of care for pregnancy-related hypertensive disorder, additional therapies that target pre-eclampsia-specific pathological factors, relieve maternal symptoms, and safely prolong pregnancy are urgently needed.

SUMMARY OF THE INVENTION

In one aspect, provided is a method of treating or preventing a pregnancy-related hypertensive disorder in a subject in need thereof, the method comprising providing ex vivo to the subject an anti-sEng antibody or sEng-binding fragment thereof and an anti-sFlt-1 antibody or sFlt-1-binding fragment thereof, wherein the anti-sEng antibody or sEng-binding fragment thereof comprises a heavy chain variable region and a light chain variable region, wherein each of the heavy chain and the light chain variable regions comprises a CDR1, CDR2, and CDR3, and wherein the sequence of CDR1H comprises SEQ ID NO:7, the sequence of CDR2H comprises SEQ ID NO:8, the sequence of CDR3H comprises SEQ ID NO:9, the sequence of CDR1L comprises SEQ ID NO:10, the sequence of CDR2L comprises SEQ ID NO:11, the sequence of CDR3L comprises SEQ ID NO:12, and wherein the anti-sFlt-1 antibody or sFlt-1-binding fragment thereof comprises a heavy chain variable region and a light chain variable region, wherein each of the heavy chain and the light chain variable regions comprises a CDR1, CDR2, and CDR3, and wherein the sequence of CDR1H comprises SEQ ID NO:1, the sequence of CDR2H comprises SEQ ID NO:2, the sequence of CDR3H comprises SEQ ID NO:3, the sequence of CDR1L comprises SEQ ID NO:4, the sequence of CDR2L comprises SEQ ID NO:5, and the sequence of CDR3L comprises SEQ ID NO:6.

In one embodiment, the heavy chain variable region of the anti-sEng antibody or sEng-binding fragment thereof comprises SEQ ID NO:22 or a sequence at least 85% identical thereto.

In one embodiment, the heavy chain variable region of the anti-sFlt-1 antibody or sFlt-1-binding fragment thereof comprises SEQ ID NO:14 or a sequence at least 85% identical thereto.

In one embodiment, the light chain variable region of the anti-sEng antibody or sEng-binding fragment thereof comprises SEQ ID NO:24 or a sequence at least 85% identical thereto.

In one embodiment, the light chain variable region of the anti-sFlt-1 antibody or sFlt-1-binding fragment thereof comprises SEQ ID NO:16 or a sequence at least 85% identical thereto.

In one embodiment, the heavy chain variable region of the anti-sEng antibody or sEng-binding fragment thereof comprises a sequence at least 85% identical to SEQ ID NO:22 and wherein the light chain variable region of the anti-sEng antibody or sEng-binding fragment thereof comprises a sequence at least 85% identical to SEQ ID NO:24.

In one embodiment, the heavy chain variable region of the anti-sEng antibody or sEng-binding fragment thereof comprises SEQ ID NO:22 and wherein the light chain variable region of the anti-sEng antibody or sEng-binding fragment thereof comprises SEQ ID NO:24.

In one embodiment, the heavy chain variable region of the anti-sFlt-1 antibody or sFlt-1-binding fragment thereof comprises a sequence at least 85% identical to SEQ ID NO:14 and wherein the light chain variable region of the anti-sFlt-1 antibody or sFlt-1-binding fragment thereof comprises a sequence at least 85% identical to SEQ ID NO:16.

In one embodiment, the heavy chain variable region of the anti-sFlt-1 antibody or sFlt-1-binding fragment thereof comprises SEQ ID NO:14 and wherein the light chain variable region of the anti-sFlt-1 antibody or sFlt-1-binding fragment thereof comprises SEQ ID NO:16.

In one embodiment, the heavy chain variable region of the anti-sEng antibody or sEng-binding fragment thereof comprises a sequence at least 85% identical to SEQ ID NO:22, wherein the light chain variable region of the anti-sEng antibody or sEng-binding fragment thereof comprises a sequence at least 85% identical to SEQ ID NO:24, wherein the heavy chain variable region of the anti-sFlt-1 antibody or sFlt-1-binding fragment thereof comprises a sequence at least 85% identical to SEQ ID NO:14, and wherein the light chain variable region of the anti-sFlt-1 antibody or sFlt-1-binding fragment thereof comprises a sequence at least 85% identical to SEQ ID NO:16.

In one embodiment, the heavy chain variable region of the anti-sEng antibody or sEng-binding fragment thereof comprises SEQ ID NO:22, wherein the light chain variable region of the anti-sEng antibody or sEng-binding fragment thereof comprises SEQ ID NO:24, wherein the heavy chain variable region of the anti-sFlt-1 antibody or sFlt-1-binding fragment thereof comprises SEQ ID NO:14, and wherein the light chain variable region of the anti-sFlt-1 antibody or sFlt-1-binding fragment thereof comprises SEQ ID NO:16.

In one embodiment, the anti-sEng antibody or sEng-binding fragment thereof has a heavy chain comprising SEQ ID NO:26 or a sequence at least 85% identical thereto.

In one embodiment, the anti-sFlt-1 antibody or sFlt-1-binding fragment thereof has a heavy chain comprising SEQ ID NO:18 or a sequence at least 85% identical thereto.

In one embodiment, the anti-sEng antibody or sEng-binding fragment thereof has a light chain comprising SEQ ID NO:28 or a sequence at least 85% identical thereto.

In one embodiment, the anti-sFlt-1 antibody or sFlt-1-binding fragment thereof has a light chain comprising SEQ ID NO:20 or a sequence at least 85% identical thereto.

In one embodiment, the anti-sEng antibody or sEng-binding fragment thereof has a heavy chain comprising a sequence at least 85% identical to SEQ ID NO:26 and wherein the anti-sEng antibody or sEng-binding fragment thereof has a light chain comprising a sequence at least 85% identical to SEQ ID NO:28.

In one embodiment, the anti-sEng antibody or sEng-binding fragment thereof has a heavy chain comprising SEQ ID NO:26 and wherein the anti-sEng antibody or sEng-binding fragment thereof has a light chain comprising SEQ ID NO:28.

In one embodiment, the anti-sFlt-1 antibody or sFlt-1-binding fragment thereof has a heavy chain comprising a sequence at least 85% identical to SEQ ID NO:18 and wherein the anti-sFlt-1 antibody or sFlt-1-binding fragment thereof has a light chain comprising a sequence at least 85% identical to SEQ ID NO:20.

In one embodiment, the anti-sFlt-1 antibody or sFlt-1-binding fragment thereof has a heavy chain comprising SEQ ID NO:18 and wherein the anti-sFlt-1 antibody or sFlt-1-binding fragment thereof has a light chain comprising SEQ ID NO:20.

In one embodiment, the anti-sEng antibody or sEng-binding fragment thereof has a heavy chain comprising a sequence at least 85% identical to SEQ ID NO:26, wherein the anti-sEng antibody or sEng-binding fragment thereof has a light chain comprising a sequence at least 85% identical to SEQ ID NO:28, wherein the anti-sFlt-1 antibody or sFlt-1-binding fragment thereof has a heavy chain comprising a sequence at least 85% identical to SEQ ID NO:18 and wherein the anti-sFlt-1 antibody or sFlt-1-binding fragment thereof has a light chain comprising a sequence at least 85% identical to SEQ ID NO:20.

In one embodiment, the anti-sEng antibody or sEng-binding fragment thereof has a heavy chain comprising SEQ ID NO:26, wherein the anti-sEng antibody or sEng-binding fragment thereof has a light chain comprising SEQ ID NO:28, wherein the anti-sFlt-1 antibody or sFlt-1-binding fragment thereof has a heavy chain comprising SEQ ID NO:18 and wherein the anti-sFlt-1 antibody or sFlt-1-binding fragment thereof has a light chain comprising SEQ ID NO:20.

In one embodiment, provided in a method of treating or preventing a pregnancy-related hypertensive disorder in a subject in need thereof, the method comprising providing ex vivo to the subject an anti-sEng antibody or sEng-binding fragment thereof and an anti-sFlt-1 antibody or sFlt-1-binding fragment thereof, wherein the anti-sEng antibody or sEng-binding fragment thereof competes for binding to sEng with an anti-sEng antibody or sEng-binding fragment thereof provided herein, and an anti-sFlt-1 antibody or sFlt-1-binding fragment thereof competes for binding to sFlt-1 with the anti-sFlt-1 antibody or sFlt-1-binding fragment thereof provided herein.

In one embodiment, the anti-sEng antibody or sEng-binding fragment thereof binds to the orphan domain of human sEng.

In one embodiment, the anti-sFlt-1 antibody or sFlt-1-binding fragment thereof binds to one or more domains 1-3 of sFlt-1.

In one embodiment, the anti-sEng antibody or sEng-binding fragment thereof does not block ligand binding to sEng.

In one embodiment, the anti-sFlt-1 antibody or sFlt-1-binding fragment thereof does not block ligand binding to sFlt-1.

In some embodiments, provided is a method of treating or preventing a pregnancy-related hypertensive disorder in a subject in need thereof, wherein the pregnancy-related hypertensive disorder is eclampsia, pre-eclampsia, or HELLP syndrome. In one embodiment, the pregnancy-related hypertensive disorder is pre-eclampsia. In one embodiment, the pregnancy-related hypertensive disorder is HELLP syndrome.

In one embodiment, the subject is a pregnant human or a postpartum human. In one embodiment, the subject is a pregnant human.

In one embodiment, provided is a method of treating or preventing a pregnancy-related hypertensive disorder in a subject in need thereof, the method comprising providing ex vivo to the subject an anti-sEng antibody or sEng-binding fragment thereof and an anti-sFlt-1 antibody or sFlt-1-binding fragment thereof, wherein the anti-sEng antibody or sEng-binding fragment thereof and the anti-sFlt-1 antibody or sFlt-1-binding fragment thereof are bound to one or more solid supports. In one embodiment, the support-bound anti-sEng antibody or sEng-binding fragment thereof and the support-bound anti-sFlt-1 antibody or sFlt-1-binding fragment thereof are bound to the same solid support. In one embodiment, the support-bound sEng antibody or sEng-binding fragment thereof and the support-bound anti-sFlt-1 antibody or sFlt-1-binding fragment thereof are bound to different solid supports.

In one embodiment, provided is a method of treating or preventing a pregnancy-related hypertensive disorder in a subject in need thereof, the method comprising providing ex vivo to the subject an anti-sEng antibody or sEng-binding fragment thereof and an anti-sFlt-1 antibody or sFlt-1-binding fragment thereof, wherein the method comprises the steps of (a) removing blood from the subject, (b) passing the blood or a component thereof over one or more solid supports to which are bound anti-sEng antibodies or sEng-binding fragments thereof and anti-sFlt-1 antibodies or sFlt-1-binding fragments thereof, to decrease the levels of sEng and sFlt-1 in the blood or component thereof, and (c) returning the blood or component thereof to the subject's body.

In one embodiment, the blood or a component thereof comprises plasma and the method comprises removing a volume of the subject's blood and separating the blood into plasma and cellular components and passing the plasma over the one or more solid supports. In one embodiment, the support-bound anti-sEng antibody or sEng-binding fragment thereof and the support-bound anti-sFlt-1 antibody or sFlt-1-binding fragment thereof are provided in a single column. In one embodiment, the support-bound anti-sEng antibody or sEng-binding fragment thereof is provided in a first column and the support-bound anti-sFlt-1 antibody or sFlt-1-binding fragment thereof is provided in a second column. In one embodiment, the blood or a component thereof is passed over the first column and the second column concurrently. In another embodiment, the blood or a component thereof is passed over the first column and the second column consecutively. In one embodiment, the blood or a component thereof is passed over the first column and subsequently over the second column. In another embodiment, the blood or a component thereof is passed over the second column and subsequently over the first column.

In one aspect, provided is a system comprising: (a) an anti-sEng antibody or sEng-binding fragment thereof disclosed herein and an anti-sFlt-1 antibody or sFlt-1-binding fragment thereof disclosed herein, wherein the anti-sEng antibody or sEng-binding fragment thereof and the anti-sFlt-1 antibody or sFlt-1-binding fragment thereof are each bound to one or more solid supports, (b) a first means for conveying blood or a component thereof from a subject to the anti-sEng antibody or sEng-binding fragment thereof and anti-sFlt-1 antibody or sFlt-1-binding fragment thereof bound to the one or more solid supports so as to contact the blood or a component thereof with the anti-sEng antibody or sEng-binding fragment thereof and the anti-sFlt-1 antibody or sFlt-1-binding fragment thereof and thereby to remove sEng and sFlt-1 from the blood or a component thereof, and (c) a second means for conveying the blood or a component thereof to the subject following contact of the blood or a component thereof with the anti-sEng antibody or sEng-binding fragment thereof and the anti-sFlt-1 antibody or sFlt-1-binding fragment thereof.

In one aspect, provided is a system comprising: (a) an anti-sEng antibody or sEng-binding fragment thereof that competes for binding to sEng with an anti-sEng antibody or sEng-binding fragment thereof disclosed herein, wherein the anti-sEng antibody or sEng-binding fragment thereof that competes for binding to sEng is bound to one or more solid supports, (b) an anti-sFlt-1 antibody or sFlt-1-binding fragment thereof that competes for binding to sFlt-1 with an anti-sFlt-1 antibody or sFlt-1-binding fragment thereof of disclosed herein, wherein the anti-sFlt-1 antibody or sFlt-1-binding fragment thereof that competes for binding to sFlt-1 is bound to one or more solid supports, (c) a first means for conveying blood or a component thereof from a subject to the anti-sEng antibody or sEng-binding fragment thereof and anti-sFlt-1 antibody or sFlt-1-binding fragment thereof bound to the one or more solid supports so as to contact the blood or a component thereof with the anti-sEng antibody or sEng-binding fragment thereof and the anti-sFlt-1 antibody or sFlt-1-binding fragment thereof and thereby to remove sEng and sFlt-1 from the blood or a component thereof, and (d) a second means for conveying the blood or a component thereof to the subject following contact of the blood or a component thereof with the anti-sEng antibody or sEng-binding fragment thereof and the anti-sFlt-1 antibody or sFlt-1-binding fragment thereof.

In one embodiment, the first means comprises: (i) an access device, inserted into a blood vessel of the subject, for accessing the subject's blood system, and (ii) a conduit system, which fluidly connects the access device to the anti-sEng antibody or sEng-binding fragment thereof and the anti-sFlt-1 antibody or sFlt-1-binding fragment thereof, bound to the one or more solid supports, thereby allowing the subject's blood or a component thereof to flow to and contact the anti-sEng antibody or sEng-binding fragment thereof and the anti-sFlt-1 antibody or sFlt-1-binding fragment thereof.

In one embodiment, the second means comprises: (i) a conduit system; and (ii) a return device, where the return device is inserted into a blood vessel of the subject, and where the conduit system fluidly connects the blood or a component thereof in contact with the anti-sEng antibody or sEng-binding fragment thereof and the anti-sFlt-1 antibody or sFlt-1-binding fragment thereof, to the return device so as to allow for the return of the blood or a component thereof to the subject.

In one embodiment, the first means comprises a device for separating the subject's blood into plasma and cellular components. In one embodiment, the device for separating the subject's blood into plasma and cellular components is a centrifuge or an apheresis device.

In one embodiment, the support-bound anti-sEng antibody or sEng-binding fragment thereof and the support-bound anti-sFlt-1 antibody or sFlt-1-binding fragment thereof are bound to the same solid support in the system.

In one embodiment, the support-bound anti-sEng antibody or sEng-binding fragment thereof and the support-bound anti-sFlt-1 antibody or sFlt-1-binding fragment thereof are bound to different solid supports in the system.

In one aspect, provided is a column comprising an anti-sEng antibody or sEng-binding fragment thereof disclosed herein and an anti-sFlt-1 antibody or sFlt-1-binding fragment thereof disclosed herein, wherein the anti-sEng antibody or sEng-binding fragment thereof and the anti-sFlt-1 antibody or sFlt-1-binding fragment thereof are bound to a solid support. In one embodiment, the support-bound anti-sEng antibody or sEng-binding fragment thereof and the support-bound anti-sFlt-1 antibody or sFlt-1-binding fragment thereof are bound to the same solid support.

In one aspect, provided is a column comprising (1) an anti-sEng antibody or sEng-binding fragment thereof that competes for binding to sEng with an anti-sEng antibody or sEng-binding fragment thereof of disclosed herein, wherein the anti-sEng antibody or sEng-binding fragment thereof that competes for binding to sEng is bound to a solid support, and (2) an anti-sFlt-1 antibody or sFlt-1-binding fragment thereof that competes for binding to sFtl-1 with an anti-sFlt-1 antibody or sFlt-1-binding fragment thereof of disclosed herein, wherein the anti-sFlt-1 antibody or sFlt-1-binding fragment thereof that competes for binding to sFtl-1 is bound to a solid support. In one embodiment, the support-bound anti-sEng antibody or sEng-binding fragment thereof that competes for binding to sEng and the support-bound anti-sFlt-1 antibody or sFlt-1-binding fragment thereof that competes for binding to sFtl-1 are bound to the same solid support.

In one embodiment, provided is a combination comprising a first column comprising an anti-sEng antibody or sEng-binding fragment thereof of disclosed herein and a second column comprising an anti-sFlt-1 antibody or sFlt-1-binding fragment thereof disclosed herein.

DETAILED DESCRIPTION

Figure 1:
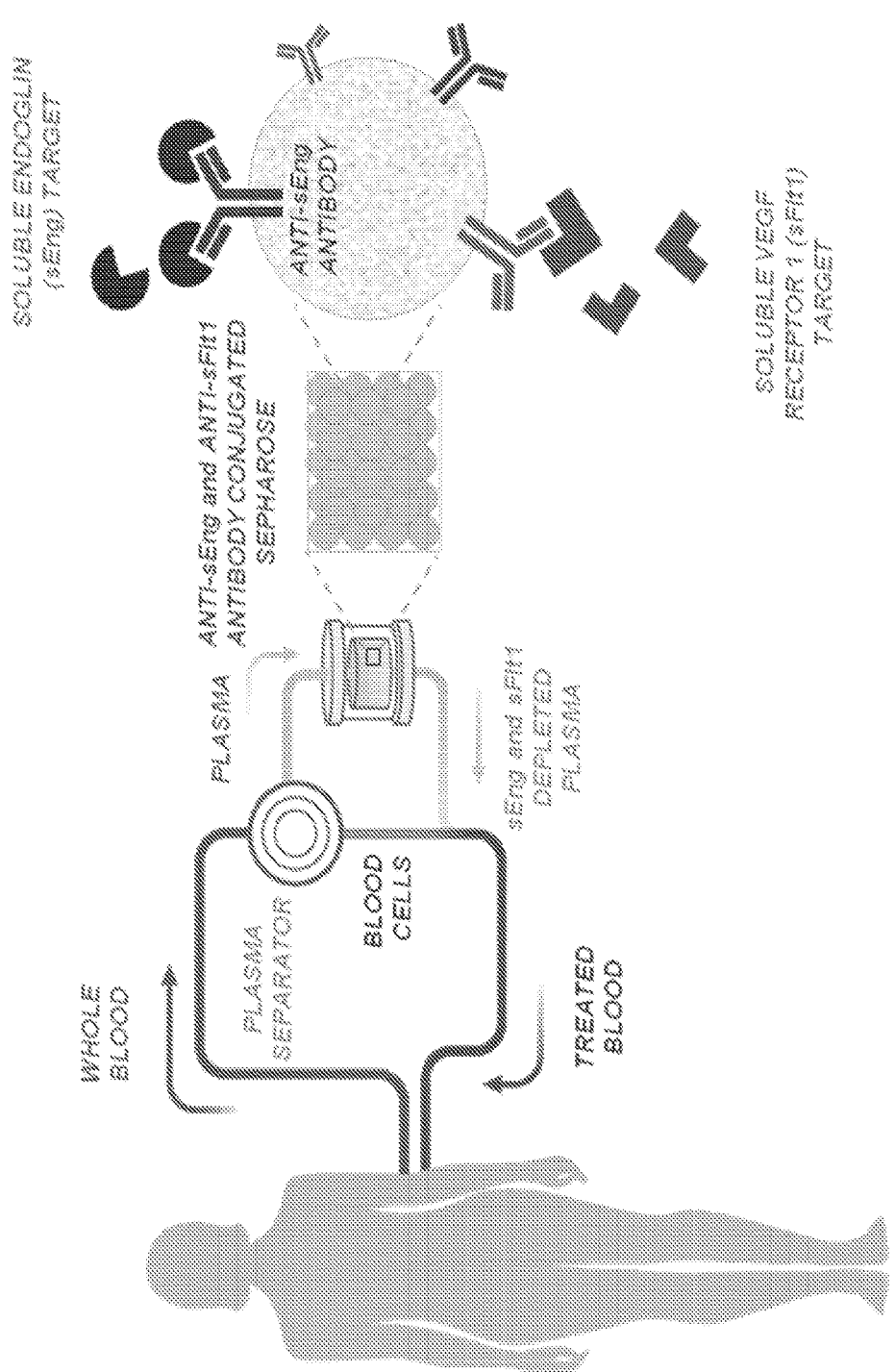
FIG. 1 illustrates one embodiment of the present disclosure, wherein blood from a subject is separated into plasma and cellular components. The cellular components are returned to the subject, while the plasma is conveyed to a column filled with SEPHAROSE® beads to which anti-sEng and anti-sFlt-1 antibodies have been bound. The anti-sEng and anti-sFlt-1 antibodies deplete the plasma of sEng and sFlt-1, and the sEng- and sFlt-1-depleted plasma recombines with cellular components and is returned to the subject.

The present invention provides a method of treating or preventing an sFlt-1- and sEng-related disease or disorder comprising providing ex vivo to the subject anti-sFlt-1 binding substances and anti-sEng binding substances in amounts sufficient and for a time sufficient to decrease the subject's blood levels of sFlt-1 and sEng. Such anti-sFlt-1 and anti-sEng binding substances include, but are not limited to, sFlt-1 ligands and binding proteins, anti-sFlt-1 antibodies and sFlt-1-binding fragments thereof, sEng ligands and binding proteins, anti-sEng antibodies, and sEng-binding fragments thereof "Ex vivo" refers to practicing the methods of treatment or prevention disclosed herein outside the body of a subject, i.e., extracorporeally, whereby the subject's blood or blood component (e.g., plasma) is contacted with anti-sFlt-1 antibodies or sFlt-1-binding fragments thereof and anti-sEng antibodies or sEng-binding fragments thereof outside the body of the subject.

In one embodiment, provided is a method of treating or preventing a pregnancy-related hypertensive disorder in a subject having or at risk of developing a pregnancy-related hypertensive disorder and thus in need of treatment or prevention for a pregnancy-related hypertensive disorder comprising providing ex vivo to the subject anti-sFlt-1 and anti-sEng binding substances—including but not limited to sFlt-1 ligands and binding proteins, anti-sFlt-1 antibodies and sFlt-1-binding fragments thereof, sEng ligands and binding proteins, anti-sEng antibodies, and sEng-binding fragments thereof—in amounts sufficient and for a time sufficient to decrease the subject's blood levels of sFlt-1 and sEng, thereby treating or preventing the pregnancy-related hypertensive disorder in the subject. In some embodiments, the pregnancy-related hypertensive disorder is eclampsia, pre-eclampsia, HELLP syndrome, or postpartum hypertension. In certain embodiments, the pregnancy-related hypertensive disorder is pre-eclampsia. In certain embodiments, the pregnancy-related hypertensive disorder is HELLP syndrome.

In another embodiment, provided is a method of treating or preventing a non-hypertensive sFlt-1 and sEng-related disorder in a subject having or at risk of developing a non-hypertensive sFlt-1 and sEng-related disorder and thus in need of treatment or prevention for a non-hypertensive sFlt-1 and sEng-related disorder, comprising providing ex vivo to the subject anti-sFlt-1 and anti-sEng binding substances—including but not limited to sFlt-1 ligands and binding proteins, anti-sFlt-1 antibodies and sFlt-1-binding fragments thereof, sEng ligands and binding proteins, anti-sEng antibodies, and sEng-binding fragments thereof—in an amount sufficient and for a time sufficient to decrease the subject's blood levels of sEng, thereby treating or preventing the non-hypertensive sFlt-1 and sEng-related disorder.

In some embodiments, the non-hypertensive sFlt-1 and sEng-related disorder is chronic kidney disease or systemic sclerosis (scleroderma). In another embodiment, the invention provides a method of treating or preventing chronic kidney disease. In another embodiment, the invention provides a method of treating or preventing systemic sclerosis (scleroderma).

sFlt-1 and sEng levels are typically elevated during the last several weeks of a normal pregnancy, and may not be accompanied by a hypertensive disorder. Accordingly, in some embodiments, the invention is used to treat non-hypertensive sFlt-1 and sEng-related disorders of late stage pregnancy and labor or prophylactically to prevent occurrence of such disorders. In one embodiment, the non-hypertensive sFlt-1 and sEng-related disorder of late stage pregnancy and labor is pre-term labor.

Several factors have been reported to have an association with fetal and placental development and severe pre-eclampsia. They include vascular endothelial growth factor (VEGF), soluble Flt-1 receptor (sFlt-1), and placental growth factor (PlGF). VEGF is an endothelial cell-specific mitogen, an angiogenic inducer, and a mediator of vascular permeability. VEGF has also been shown to be important for glomerular capillary repair. VEGF is disclosed in U.S. Pat. Nos. 5,332,671; 5,240,848; and 5,194,596; as well as in Charnock-Jones et al., 1993, Biol. Reproduction, 48: 1120-1128. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. VEGF includes several family members or isoforms (e.g., VEGF-A, VEGF-B, VEGF-C, VEGF-D, VEGF-E, VEGF189, VEGF165, or VEGF 121); see Tischer et al., 1991, J. Biol. Chem. 266, 11947-11954; Neufed et al., 1996, Cancer Metastasis 15:153-158; U.S. Pat. Nos. 6,447,768; 5,219,739; and 5,194,596. Also known are mutant forms of VEGF such as the KDR-selective VEGF and Flt-selective VEGF described in Gille et al., 2001, J. Biol. Chem. 276:3222-3230. Modified forms of VEGF are described in LeCouter et al., 2003, Science 299:890-893.

VEGF binds as a homodimer to two homologous membrane-spanning tyrosine kinase receptors, the fins-like tyrosine kinase (Flt-1) and the kinase domain receptor (KDR), which are differentially expressed in endothelial cells obtained from many different tissues. GenBank accession number AF063657 provides the nucleotide and amino acid sequences of human Flt-1. Flt 1, but not KDR, is highly expressed by trophoblast cells which contribute to placental formation. PlGF is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not to the KDR receptor. Both PlGF and VEGF contribute to the mitogenic activity and angiogenesis that are critical for the developing placenta.

sFlt-1, also known as sVEGFR1, lacks the transmembrane and cytoplasmic domains of the full-length Flt-1 receptor and was identified in the culture medium of human umbilical vein endothelial cells. The in vivo expression of sFlt-1 was subsequently demonstrated in placental tissue. sFlt-1 binds to VEGF with high affinity but does not stimulate mitogenesis of endothelial cells. The elevated levels of sFlt-1 found in the serum samples taken from pregnant women suffering from, or at risk of developing, a pregnancy-related hypertensive disorder (e.g., pre-eclampsia or eclampsia) indicate that sFlt-1 is acting as a "physiologic sink" to bind to and deplete the trophoblast cells and maternal endothelial cells of functional growth factors required for the proper development and angiogenesis of the fetus and/or the placenta.

"Soluble Flt-1 (sFlt-1)" refers to a soluble form of the Flt-1 receptor that is identical or homologous to the protein defined by GenBank accession number AF063657, and has sFlt-1 biological activity. The biological activity of sFlt-1 may be assayed using any standard method, for example, by assaying sFlt-1-binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 includes any sFlt-1 family member or isoform. Non-limiting examples include sFlt-1 isoforms that are recognized to be splice variants. The splice variants have a common transcription start site, but do not contain all 30 spliced exons that encode Flt-1. One isoform is encoded by an mRNA having the first 13 exons followed by a portion of intron 13 and a poly(A) signal sequence and contains the first six Ig-like domains, but not the seventh Ig-like domain, transmembrane domain, or intracellular domain. (GenBank Accession No. AF063657; Kendall et al., Proc. Natl. Acad. Sci. USA 1993, 90:10705-9). Another isoform is encoded by an mRNA having the first 14 exons followed by a new alternatively spliced terminal exon 15 and a poly(A) signal sequence. The isoform is truncated in the seventh extracellular Ig-like domain (GenBank Accession No. AI188382; Thomas et al., 2007, FASEB J. 21:3885-3895). Several other alternatively spliced mRNAs and their translation products have also been reported or predicted. Each of these proteins contain unique C-terminal sequences that include amino acids encoded by the alternatively spliced 3' end of the mRNA up to the first translation termination codon. sFlt-1 can also mean degradation products or fragments that result from enzymatic cleavage of the Flt-1 receptor where such degradation products or fragments maintain sFlt-1 biological activity. In one example, specific metalloproteinases released from the placenta may cleave the extracellular domain of Flt-1 receptor to release the N-terminal portion of Flt-1 into circulation.

Another factor associated with fetal and placental development and severe pre-eclampsia is soluble Endoglin (sEng). Increased sEng levels in pregnant women precede the onset of pre-eclampsia symptoms and are highly correlated with disease severity and clinical outcome.

Endoglin, also known as CD105, is an accessory receptor for transforming growth factor ligands (TGF-β). Eng is a homodimeric, disulfide-linked transmembrane glycoprotein comprising a large extracellular domain (ectodomain), a hydrophobic transmembrane domain, and a short intracellular domain. Two isoforms of Eng receptor exist, L (long) and S (short), which differ in the length of intracellular domain, tissue distribution, and degree of phosphorylation. GenBank accession numbers NM_001114753 and NM_000118 provide the nucleotide and amino acid sequences of human L-Endoglin and S-Endoglin receptors, respectively. Both of these isoforms of Endoglin are highly expressed in endothelial cells and placental syncytiotrophoblast cells, as well as in monocytes and erythropoietic cells at lower levels.

Soluble Endoglin (sEng) lacks the transmembrane and cytoplasmic domains of the full-length L- and S-Endoglin receptors, as it is cleaved from the transmembrane domain and the cytoplasmic domain of the L- or S-Endoglin membrane-bound receptors. "Soluble Endoglin (sEng)" refers to a soluble form of the receptor Endoglin that is identical or homologous to the protein defined by GenBank accession number X72012, and has sEng biological activity. As used herein, sEng may refer to any sEng family member, sEng spliced isoform, and/or sEng degradation product. Non-limiting examples include sEng isoforms that are recognized to be cleaved between residues in the ectodomain. In one embodiment, sEng is the full soluble ectodomain product cleaved by a membrane-bound metalloprotease at the junction between ectodomain and the transmembrane domain of the L-Endoglin receptor, the major isoform with a cytoplasmic tail of 47 residues (Transcript variant 1, Accession #NM_001114753), and the S-Endoglin receptor containing a 14 residue cytoplasmic tail (Transcript variant 2, Accession #NM_000118). The term sEng may also refer to degradation products or fragments that result from enzymatic or cleavages other than metalloproteases that cleave at the C-terminal end of the extracellular domain (residues 26 to 586). In one embodiment, the soluble Endoglin product released from the placenta and into the circulation of pre-eclampsia patients is truncated at the ZP domain, with the truncated sEng product spanning residues 27 to 393 (Venkatesha et al, Nat Med. 2006 June; 12(6):642-9). The biological activity of sEng may be assayed using any standard method, for example, by binding to Bone Morphogenetic Protein 9 (BMP9) or BMP10, to TGF-β1 or TGF-β3 ligand in complex with TGFβ Receptor I or II, or by assaying its ability to inhibit BMP10-induced alkaline phosphatase production in MC3T3E1 mouse pre-osteoblast cell line.

In endothelial cells, TGF-β1 and TGF-β3 bind Endoglin with high affinity in the presence of TGF-β receptor II (TGFβ RII) and/or the TGF-β receptor I (TGF-β RI, or ALK5), to promote proliferation and activation of endothelial cells. As such, The TGF-β1 and TGF-β3 ligands contribute to angiogenesis that is critical for the developing fetus and/or the placenta.

The sEng protein sequesters the TGF-β1 and TGF-β3 ligands when these ligands are bound to TGF-β receptor I and/or II. As such, sEng prevents ligand binding to the membrane-bound forms of Eng, thereby attenuating the TGF-β and Smad-mediated signaling and angiogenesis. Also, sEng downregulates TGF-β signaling and attenuates endothelial nitric acid synthase (eNOS) activation in endothelial cells, leading to decreased nitric oxide availability and disrupted vascular homeostasis.

On endothelial cells, BMP ligands bind membrane forms of Endoglin and activate another type I receptor called the activin receptor-like kinase 1 (ALK1) and a type II BMP-RII receptor. ALK1 activation leads to a Smad-mediated signaling distinct from TGF-β pathway and affects cell proliferation, angiogenesis and vascular homeostasis. The sEng protein can also bind directly to BMP9 and BMP10 ligands.

sEng was identified in sera of pregnant women and was found to be expressed in the placenta and released into the circulation of severe pre-eclampsia patients (Venkatesha et al, Nat Med. 2006 June; 12(6):642-9). Adenoviral overexpression of sEng and sFlt-1 in rats resulted in severe pre-eclampsia phenotypes of increased blood pressure, high proteinuria and severe glomerular endotheliosis, and over-expression of sEng and sFlt-1 in mice interfered with endothelial cell stability and development of periventricular edema. Increased sEng levels were also found in the vascular surgical samples of patients with brain arteriovenous malformations, similar to those found in hereditary hemorrhagic telangiectasia type 1 (HHT1) patients, in which Endoglin haploinsufficiency may be an underlying cause of focal loss of capillaries and arteriovenous malformations. The elevated levels of sEng and sFlt-1 found in the sera of pregnant women suffering from, or at risk of developing, a pregnancy-related hypertensive disorder (e.g., severe pre-eclampsia, eclampsia, or HELLP syndrome) indicate that sEng acts as a "physiologic sink" to bind to and deplete the trophoblast cells and maternal endothelial cells of functional growth factors such as TGF-β ligands required for the proper development and angiogenesis of the fetus and/or the placenta.

"sFlt-1-binding substances" include antibodies, antibody fragments, ligands, and any other binding molecules (e.g., natural or synthetic proteins, polypeptides, and polymers) that selectively bind to sFlt-1. "Anti-sFlt antibody" refers to an antibody or fragment thereof that is capable of binding to sFlt-1. "sFlt-1-binding fragment" of an anti-sFlt-1 antibody refers to a portion of an anti-sFlt-1 antibody that retains the ability to bind sFlt-1. "sFlt-1 ligand" refers to a protein or derivative thereof that binds to sFlt-1. Naturally occurring sFlt-1 ligands include, without limitation, vascular endothelial growth factor (VEGF), and placental growth factor (PlGF). The VEGF is preferably VEGF-A or VEGF-B. VEGF includes its isoforms, including without limitation, VEGF121, VEGF165, and VEGF189. PlGF includes it isoforms, including without limitation, PlGF-1, PlGF-2, PlGF-3, and PlGF-4. Derivatives include without limitation VEGF and PlGF fusion proteins and sequence variants of VEGF and PlGF that bind to sFlt-1.

The sFlt-1-binding substances disclosed herein are effective to efficiently deplete sFlt-1 in blood or plasma from a subject. The sFlt-1 can be soluble, or in microparticles circulating in the bloodstream. sFlt-1 is removed from the blood or plasma by virtue of being captured by the solid-support bound sFlt-1-binding substances disclosed herein, and is no longer available to bind to, and thus reduce the concentration of, ligands such as VEGF and/or PlGF in the blood or plasma. Further, when captured by solid support-bound antibodies or binding fragments thereof, sFlt-1 is no longer available to form heterodimers with membrane-bound Flt-1 or KDR. Heparin can be administered to the subject to release tissue-bound sFlt-1, enhancing ex vivo depletion of sFlt-1 and minimizing the pool of non-circulating sFlt-1 left in the subject.

In one aspect, an sFlt-1-binding substance binds to a site on sFlt-1 such that binding of VEGF and/or PlGF to sFlt-1 is not blocked.

In one embodiment, the sFlt-1-binding substances disclosed herein bind to one or more extracellular Ig-like domains of Flt-1. In certain embodiments, the sFlt-1-binding substances disclosed herein bind to one or more of domains 1-3 of sFlt-1. The domain structure of Flt-1 has been described. (See, e.g., Davis-Smyth et al., 1996, EMBO Journal, 15(18):4919-27). For example, the first Ig-like domain extends from about Pro32 to about Ile128. The second Ig-like domain extends from about Pro134 to about Thr226. The third Ig-like domain extends from about Val232 to about Lys331. The fourth Ig-like domain, which is thought to be critical for receptor dimer formation, extends from about Phe333 to about Pro428. The fifth Ig-like domain extends from about Tyr431 to about Thr553. The sixth Ig-like domain extends from about Gly558 to about Arg656. The seventh Ig-like domain extends from about Tyr662 to about Thr751.

In certain embodiments, the sFlt-1-binding substances disclosed herein bind to sFlt-1 so as to prevent dimerization.

Binding of Flt-1 ligand to Flt-1 is understood to be cooperative, such that a stable receptor-ligand complex includes a ligand dimer bound to a receptor dimer. Accordingly, blocking receptor dimerization destabilizes receptor-ligand interactions. When sFlt-1-binding substances that block dimerization are employed in the ex vivo methods disclosed herein, such sFlt-1-binding substances bind to sFlt-1 and reduce the amount of circulating sFlt-1. Thus, the amount of sFlt-1 in a subject is reduced without a substantial reduction of sFlt-1 ligand. Since dimerization of bound sFlt-1 is blocked, the stability of any sFlt-1 monomer with ligand is reduced. Thus, any reduction of sFlt-1 ligand in the subject may be insubstantial.

In certain embodiments, the sFlt-1-binding substances disclosed herein bind to sFlt-1 but do not substantially block or inhibit sFlt-1 dimerization. In certain embodiments, the sFlt binding substances disclosed herein bind to an epitope that is present in all isoforms of sFlt-1.

In one embodiment, the sFlt-1-binding substances disclosed herein bind to Ig-like domain 1 of sFlt-1. In another embodiment, the sFlt-1-binding substances disclosed herein bind to Ig-like domain 2 of sFlt-1. In another embodiment, the sFlt-1-binding substances disclosed herein bind to Ig-like domain 3 of sFlt-1. In yet another embodiment, the sFlt-1-binding substances disclosed herein bind to Ig-like domains 1-2 of sFlt-1. In another embodiment, the sFlt-1-binding substances disclosed herein bind to Ig-like domains 2-3 of sFlt-1. In still another embodiment, the sFlt-1-binding substances disclosed herein bind to Ig-like domains 1 and 3 of sFlt-1.

"sEng-binding substances" include antibodies, antibody fragments, ligands, and any other binding molecules (e.g., natural or synthetic proteins, polypeptides, and polymers) that selectively bind to sEng. "Anti-sEng antibody" refers to an antibody or fragment thereof that is capable of binding to sEng. "sEng-binding fragment" of an anti-sEng antibody refers to a portion of an anti-sEng antibody that retains the ability to bind sEng. "sEng ligand" refers to a protein or derivative thereof that binds to sEng. Naturally occurring sEng ligands include, without limitation, BMP9, BMP10, and TGF-β, including, but not limited to TGF-β1 and TGF-β3.

The sEng-binding substances disclosed herein are effective to efficiently deplete sEng in blood or plasma from a subject. The sEng can be soluble, or in microparticles circulating in the bloodstream. sEng is removed from the blood or plasma by virtue of being captured by the solid-support bound sEng-binding substances disclosed herein, and is no longer available to bind to, and thus reduce the concentration of, ligands such as TGF-β1 and/or TGF-β3 in the blood or plasma. Heparin can be administered to the subject to release tissue-bound sEng, enhancing ex vivo depletion of sEng and minimizing the pool of non-circulating sEng left in the subject.

In one aspect, the sEng binding substance binds to a site on sEng such that binding of TGF-β1 and/or TGF-β3 to sEng is not blocked.

In one embodiment, the sEng-binding substances disclosed herein are employed in the ex vivo methods disclosed herein, and bind to sEng molecules that are not bound by sEng ligands, removing those sEng molecules from blood or plasma.

In one embodiment, the sEng-binding substances disclosed herein bind to the ectodomain of an Endoglin monomer, dimer, or oligomer. In one aspect, the sEng-binding substances disclosed herein bind to the extracellular orphan domain (OD) of an sEng monomer, dimer or oligomer and optionally to the linker region between the OD and the ZPD of an sEng monomer, dimer or oligomer.

In certain embodiments, the sEng-binding substances disclosed herein bind to an epitope that is present in all degradation products, fragments or isoforms of sEng.

Non-limiting examples of anti-sFlt-1 antibody sequences are provided. In certain embodiments, the anti-sFlt-1 antibodies or sFlt-1-binding fragments thereof comprise one, two, or three heavy chain CDRs having SEQ ID NO:1, SEQ ID NO:2, and/or SEQ ID NO:3 and/or one, two, or three light chain CDRs having SEQ ID NO:4, SEQ ID NO:5, and/or SEQ ID NO:6. In certain embodiments, anti-sFlt-1 antibodies or sFlt-1-binding fragments thereof comprise one, two, or three heavy chain CDRs having substantially the same sequence as SEQ ID NO:1, SEQ ID NO:2, and/or SEQ ID NO:3 and/or one, two, or three light chain CDRs having substantially the same sequence as SEQ ID NO:4 SEQ ID NO:5, and/or SEQ ID NO:6. In one embodiment, the anti-sFlt-1 antibody or sFlt-1-binding fragment thereof comprises a heavy chain variable region and a light chain variable region, wherein each of the heavy chain and the light chain variable regions comprises a CDR1, CDR2, and CDR3, and wherein CDR1H comprises SEQ ID NO:1, CDR2H comprises SEQ ID NO:2, CDR3H comprises SEQ ID NO:3, CDR1L comprises SEQ ID NO:4, CDR2L comprises SEQ ID NO:5, and CDR3L comprises SEQ ID NO:6. In certain embodiments, the anti-sFlt-1 antibody or sFlt-1-binding fragment thereof comprises at least one variable region comprising an amino acid sequence selected from SEQ ID NOs:14 and 16, or a sequence at least 85% at least 90%, at least 95%, at least 96%, at least 97%, at least 98%, or at least 99%, identical to SEQ ID NOs:14 or 16.

"Identity" refers to the number or percentage of identical positions shared by two amino acid or nucleic acid sequences, taking into account the number of gaps, and the length of each gap, which need to be introduced for optimal alignment of the two sequences. "Substantially identical" means an amino acid sequence that which differs only (i) by conservative amino acid substitutions, for example, substitution of one amino acid for another of the same class (e.g., valine for glycine, arginine for lysine, etc.) or (ii) by one or more non-conservative substitutions, deletions, or insertions located at positions of the amino acid sequence which do not destroy the function of the protein. Preferably, the amino acid sequence is at least 80%, at least 85%, at least 90%, at least 95%, at least 96%, at least 97%, at least 98%, or at least 99% similar to another amino acid sequence. Methods and computer programs for determining sequence similarity are publicly available, including, but not limited to, the GCG program package (Devereux et al., Nucleic Acids Research 12:387, 1984), BLASTP, BLASTN, FASTA (Altschul et al., J. Mol. Biol. 215:403 (1990), and the ALIGN program (version 2.0). The well-known Smith-Waterman algorithm may also be used to determine similarity. The BLAST program is publicly available from NCBI and other sources (BLAST Manual, Altschul, et al., NCBI NLM NIH, Bethesda, Md. 20894; BLAST 2.0). In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

It is observed herein that the ability of an antibody to deplete sFlt-1 from blood or a component thereof is not necessarily dependent on binding affinity, but also can depend on certain other characteristics, such as the domains or epitope of sFlt-1 to which the antibody binds.

In certain embodiments, the anti-sFlt-1 antibody or sFlt-1-binding fragment thereof competes for binding with an antibody which comprises one, two, or three heavy chain CDRs comprising SEQ ID NO:1, SEQ ID NO:2, and/or SEQ ID NO:3 and/or one, two, or three light chain CDRs comprising SEQ ID NO:4, SEQ ID NO:5, and/or SEQ ID NO:6. In certain embodiments, the anti-sFlt-1 antibody or sFlt-1-binding fragment thereof competes for binding with an antibody which comprises one, two, or three heavy chain CDRs comprising substantially the same sequence as SEQ ID NO:1, SEQ ID NO:2, and/or SEQ ID NO:3 and/or one, two, or three light chain CDRs comprising substantially the same sequence as SEQ ID NO:4, SEQ ID NO:5, and/or SEQ ID NO:6. In certain embodiments, the anti-sFlt-1 antibody or sFlt-1-binding fragment thereof competes with an antibody comprising a CDR1H comprising SEQ ID NO:1, a CDR2H comprising SEQ ID NO:2, a CDR3H comprising SEQ ID NO:3, a CDR1L comprising SEQ ID NO:4, a CDR2L comprising SEQ ID NO:5, and a CDR3L comprising SEQ ID NO:6. In some embodiments, the anti-sFlt-1 antibody or sFlt-1-binding fragment thereof competes for binding with an anti-sFlt-1 antibody or sFlt-1-binding fragment thereof, which comprises at least one variable region comprising an amino acid sequence selected from SEQ ID NOs:14 and 16, or a sequence at least 85% at least 90%, at least 95%, at least 96%, at least 97%, at least 98%, or at least 99%, identical thereto. In some embodiments, the anti-sFlt-1 antibody or sFlt-1-binding fragment thereof competes for binding with an anti-sFlt-1 antibody or sFlt-1-binding fragment thereof, which comprises at least one amino acid sequence selected from SEQ ID NOs:18 and 20, or a sequence at least 85% at least 90%, at least 95%, at least 96%, at least 97%, at least 98%, or at least 99%, identical thereto. Two antibodies "compete" (i.e., bind to the same or overlapping epitope) if each competitively inhibits (blocks) binding of the other to the antigen. That is, a 1×, 5×, 10×, 20×, or 100× excess of one antibody inhibits binding of the other by at least 50%, preferably 75%, 90%, or even 99% as measured in a competitive binding assay (see, e.g., Junghans et al., Cancer Res. 50:1495, 1990). Additional methods of determining whether one antibody binds to the same or overlapping epitope as another antibody are well known in the art.

In certain embodiments, the sFlt-1 antibody or sFlt-1-binding fragment thereof binds to an epitope on human sFlt-1 that is bound by an antibody referred to herein as AG10B.

In certain embodiments, the anti-sFlt-1 antibody or sFlt-1-binding fragment thereof binds human sFlt-1 but does not bind human Flt-1. In certain embodiments, the anti-sFlt-1 antibody or sFlt-1-binding fragment thereof that binds sFlt-1 recognizes the extracellular domain of Flt-1. In certain embodiments, the anti-sFlt-1 antibody, or sFlt-1-binding fragment thereof recognizes an epitope in sFlt-1 that is not present in Flt-1. In certain embodiments, such an epitope not present in Flt-1 includes amino acids from the carboxy terminus of sFlt-1. In certain embodiments, such an epitope not present in Flt-1 is a discontinuous epitope or a conformational epitope of sFlt-1. In certain embodiments, the anti-sFlt-1 antibodies, or sFlt-1-binding fragments thereof, bind to the ligand binding site of Flt-1.

In one embodiment, the anti-sFlt-1 antibody or sFlt-1-binding fragment thereof comprises one or more variable regions comprising SEQ ID NO:14 and/or SEQ ID NO:16 and a human IgG1 constant region. In one embodiment, the anti-sFlt-1 antibody or sFlt-1-binding fragment thereof comprises SEQ ID NO:18 and/or SEQ ID NO:20.

The antibodies may also be modified to minimize or eliminate other effects. In one embodiment, the constant region of the anti-sFlt-1 antibody of fragment thereof disclosed herein may include a mutation that prevents glycosylation. For example, the heavy chain of anti-sFlt-1 antibody AG10B (SEQ ID NO:18) contains a N298Q mutation. Antibodies containing this mutation are deficient in effector functions, such as complement activation and binding to Fc. In another embodiment, the anti-sFlt-1 antibody of fragment thereof disclosed herein may contain a mutation that disrupts binding of the antibody to neonatal Fc receptor (FcRn). The FcRn receptor facilitates transport of maternal IgG across the placenta to the fetus. Accordingly, an anti-sFlt-1 antibody or sFlt-1-binding fragment thereof with a mutation that disrupts binding of the antibody to FcRn would bind sFlt-1 in the treatment subject, but would not be transported to the growing fetus. For example, the heavy chain of anti-sFlt-1 antibody AB10B (SEQ ID NO:18) may contain a I254A mutation. In one embodiment, the anti-sFlt-1 antibody or sFlt-1-binding fragment thereof disclosed herein may contain both mutations (for example N298Q and I254A in SEQ ID NO:18).

Non-limiting examples of anti-sEng antibody sequences are provided. In certain embodiments, the anti-sEng antibodies or sEng-binding fragments thereof comprise one, two, or three heavy chain CDRs having SEQ ID NO:7, SEQ ID NO:8, and/or SEQ ID NO:9 and/or one, two, or three light chain CDRs having SEQ ID NO:10, SEQ ID NO:11, and/or SEQ ID NO:12. In certain embodiments, anti-sEng antibodies or sEng-binding fragments thereof comprise one, two, or three heavy chain CDRs having substantially the same sequence as SEQ ID NO:7, SEQ ID NO:8, and/or SEQ ID NO:9 and/or one, two, or three light chain CDRs having substantially the same sequence as SEQ ID NO:10 SEQ ID NO:11, and/or SEQ ID NO:12. In one embodiment, the anti-sEng antibody or sEng-binding fragment thereof comprises a heavy chain variable region and a light chain variable region, wherein each of the heavy chain and the light chain variable regions comprises a CDR1, CDR2, and CDR3, and wherein CDR1H comprises SEQ ID NO:7, CDR2H comprises SEQ ID NO:8, CDR3H comprises SEQ ID NO:9, CDR1L comprises SEQ ID NO:10, CDR2L comprises SEQ ID NO:11, and CDR3L comprises SEQ ID NO:12. In certain embodiments, the anti-sEng antibody or sEng-binding fragment thereof comprises at least one variable region comprising an amino acid sequence selected from SEQ ID NOs:22 and 24, or a sequence at least 85% at least 90%, at least 95%, at least 96%, at least 97%, at least 98%, or at least 99%, identical to SEQ ID NOs:22 or 24.

It is observed herein that the ability of an antibody to deplete sEng from blood or a component thereof is not necessarily dependent on binding affinity, but also can depend on certain other characteristics, such as the domains or epitope of sEng to which the antibody binds.

In certain embodiments, the anti-sEng antibody or sEng-binding fragment thereof competes for binding with an antibody which comprises one, two, or three heavy chain CDRs comprising SEQ ID NO:7, SEQ ID NO:8, and/or SEQ ID NO:9 and/or one, two, or three light chain CDRs comprising SEQ ID NO:10, SEQ ID NO:11, and/or SEQ ID NO:12. In certain embodiments, the anti-sEng antibody or sEng-binding fragment thereof competes for binding with an antibody which comprises one, two, or three heavy chain CDRs comprising substantially the same sequence as SEQ ID NO:7, SEQ ID NO:8, and/or SEQ ID NO:9 and/or and one, two, or three light chain CDRs comprising substantially the same sequence as SEQ ID NO:10, SEQ ID NO:11, and/or SEQ ID NO:12. In certain embodiments, the anti-sEng antibody or sEng-binding fragment thereof competes with an antibody comprising a CDR1H comprising SEQ ID NO:7, a CDR2H comprising SEQ ID NO:8, a CDR3H comprising SEQ ID NO:9, a CDR1L comprising SEQ ID NO:10, a CDR2L comprising SEQ ID NO:11, and a CDR3L comprising SEQ ID NO:12. In some embodiments, the anti-sEng antibody or sEng-binding fragment thereof competes for binding with an anti-sEng antibody or sEng-binding fragment thereof, which comprises at least one variable region comprising an amino acid sequence selected from SEQ ID NOs:22 and 24, or a sequence at least 85% at least 90%, at least 95%, at least 96%, at least 97%, at least 98%, or at least 99%, identical thereto. In some embodiments, the anti-sEng antibody or sEng-binding fragment thereof competes for binding with an anti-sEng antibody or sEng-binding fragment thereof, which comprises at least one amino acid sequence selected from SEQ ID NOs:26 and 28, or a sequence at least 85% at least 90%, at least 95%, at least 96%, at least 97%, at least 98%, or at least 99%, identical thereto.

In certain embodiments, the sEng antibody or sEng-binding fragment thereof binds to an epitope on human sEng that is bound by one or more of the antibodies referred to herein as MAb 210 or cENG10.

In certain embodiments, anti-sEng antibody or sEng-binding fragment thereof binds human sEng but does not bind human Eng. In certain embodiments, the anti-sEng antibody or sEng-binding fragment thereof recognizes the extracellular domain of Endoglin. In certain embodiments, anti-sEng antibody or sEng-binding fragment thereof recognizes an epitope in sEng that is not present in membrane-bound Eng. In certain embodiments, such an epitope not present in membrane-bound Eng is a discontinuous epitope or a conformational epitope of Eng. In certain embodiments, anti-sEng antibody or sEng-binding fragment thereof binds to the ligand binding site of sEng.

In one embodiment, the anti-sEng antibody or sEng-binding fragment thereof comprises one or more variable regions comprising SEQ ID NO:22 and/or SEQ ID NO:24 and a human IgG1 constant region. In one embodiment, the anti-sEng antibody or sEng-binding fragment thereof comprises SEQ ID NO:26 and/or SEQ ID NO:28.

The antibodies may also be modified to minimize or eliminate other effects. In one embodiment, the constant region of the anti-sEng antibody of fragment thereof disclosed herein may include a mutation that prevents glycosylation. For example, the heavy chain of anti-sEng antibody cENG10 (SEQ ID NO:26) contains a N300Q mutation. Antibodies containing this mutation are deficient in effector functions, such as complement activation and binding to Fc. In another embodiment, the anti-sEng antibody of fragment thereof disclosed herein may contain a mutation that disrupts binding of the antibody to neonatal Fc receptor (FcRn). The FcRn receptor facilitates transport of maternal IgG across the placenta to the fetus. Accordingly, an anti-sEng antibody or sEng-binding fragment thereof with a mutation that disrupts binding of the antibody to FcRn would bind sEng in the treatment subject, but would not be transported to the growing fetus. For example, the heavy chain of anti-sEng antibody cENG10 (SEQ ID NO:26) may contain a I256A mutation. In one embodiment, the anti-sEng antibody or sEng-binding fragment thereof disclosed herein may contain both mutations (for example N300Q and I256A in SEQ ID NO:26).

In certain embodiments, the anti-sFlt-1 antibodies or sFlt-1-binding fragments thereof and the anti-sEng antibodies or sEng-binding fragments thereof disclosed herein are particularly suitable for administration to a subject. For example, the antibodies can be modified to minimize immunogenicity and/or hypersensitivity in a subject. Such modifications can provide an additional safety factor in the event that antibodies are leached from a column or other solid support used for ex vivo treatment of a subject.

Further, in certain embodiments, the anti-sFlt-1 antibodies or sFlt-1-binding fragments thereof and the anti-sEng antibodies or sEng-binding fragments thereof disclosed herein can be administered in vivo to treat a pregnancy-related hypertensive disorder. In some embodiments, the pregnancy-related hypertensive disorder is eclampsia, pre-eclampsia, HELLP syndrome, or postpartum hypertension. In certain embodiments, the pregnancy-related hypertensive disorder is pre-eclampsia.

In certain embodiments, the anti-sEng antibodies or sEng-binding fragments thereof disclosed herein can be administered in vivo to treat a non-hypertensive sEng-related disorder. In some embodiments, the non-hypertensive sFlt-1 and sEng-related disorder is chronic kidney disease, systemic sclerosis (scleroderma), or a non-hypertensive sFlt-1 and sEng-related disorder of late stage pregnancy and labor. In one embodiment, the non-hypertensive sFlt-1 and sEng-related disorder of late stage pregnancy and labor is pre-term labor.

Thus, for both ex vivo and in vivo treatment, antibodies disclosed herein include chimeric or humanized antibodies, as well as antigen binding fragments of the anti-sFlt-1 antibodies and the anti-sEng antibodies disclosed herein.

Disclosed herein are anti-sFlt-1 antibodies or sFlt-1-binding fragments thereof and anti-sEng antibodies or sEng-binding fragments thereof that are suitable for use in the present methods and systems, including, but not limited to antibodies AG10B and cENG10. Also contemplated are anti-sFlt-1 antibodies and sFlt-1-binding fragments thereof that comprise the variable region sequences and/or CDRs of the anti-sFlt-1 antibodies and sFlt-1-binding fragments thereof disclosed herein as well as anti-sFlt-1 antibodies and sFlt-1-binding fragments thereof that comprise variable region sequences or CDRs that have certain specified levels of identity in amino acid sequence to the variable region sequences or CDRs of the anti-sFlt-1 antibodies and sFlt-1-binding fragments thereof disclosed herein. Likewise, also contemplated are anti-sEng antibodies and sEng-binding fragments thereof that comprise the variable region sequences and/or CDRs of the anti-sEng antibodies and sFlt-1-binding fragments thereof disclosed herein as well as anti-sEng antibodies and sFlt-1-binding fragments thereof that comprise variable region sequences or CDRs that have certain specified levels of identity in amino acid sequence to the variable region sequences or CDRs of the anti-sEng antibodies and sFlt-1-binding fragments thereof disclosed herein.

In designing and producing additional anti-sFlt-1 antibodies and anti-sEng antibodies, those skilled in the art may be guided by certain well known features of antibodies. The structure of typical naturally occurring antibodies is well known and includes two identical heavy chains and two identical light chains, with each light chain covalently linked to a heavy chain by an interchain disulfide bond. The two heavy chains are linked to one another by additional disulfide bonds. Individual heavy and light chains can fold into domains having similar sizes (110-125 amino acids) and structures, but different functions. Light chains can comprise one variable domain ($V_L$) and/or one constant domain ($C_L$). Heavy chains can also comprise one variable domain ($V_H$) and/or three or four constant domains ($C_H1$, $C_H2$, $C_H3$ and $C_H4$), depending on the class or isotype of antibody. In humans, the isotypes are IgA, IgD, IgE, IgG, and IgM, with IgA and IgG further subdivided into subclasses or subtypes ($IgA_{1-2}$ and $IgG_{1-4}$).

It has been found to be convenient to consider certain portions of antibody molecules individually. The portion of an antibody consisting of $V_L$ and $V_H$ domains is designated Fv (fragment variable) and constitutes the antigen-binding site. An antibody fragment containing a $V_L$ domain and a $V_H$ domain on one polypeptide chain is referred to as a single chain Fv (scFv) and generally contains the N terminus of one domain and the C terminus of the other domain joined by a flexible linker (see, e.g., U.S. Pat. No. 4,946,778 and International Patent Publication WO 88/09344.

For certain embodiments disclosed herein, it may be advantageous to employ scFv fragments because scFv fragments lack some or all of the constant domains of whole antibodies. Therefore, they can overcome some of the side-effects associated with the use of whole antibodies. For example, scFv fragments tend to be free of certain undesired interactions between heavy-chain constant regions and other biological molecules.

In certain embodiments, the anti-sFlt-1 antibodies or sFlt-1-binding fragments thereof and/or the anti-sEng antibodies or sEng-binding fragments thereof disclosed herein are multivalent single chain antibodies, where multiple single chain antibodies, each single chain having one $V_H$ and one $V_L$ domain covalently linked by a first peptide linker, are covalently linked by at least one or more second peptide linkers to form a multivalent single chain antibody. Each chain of a multivalent single chain antibody includes a variable light chain fragment and a variable heavy chain fragment, and is linked by the second peptide linker to at least one other chain. The second peptide linker is preferably composed of at least fifteen and fewer than one hundred amino acid residues.

In certain embodiments, the anti-sFlt-1 antibodies or sFlt-1-binding fragments thereof and/or the anti-sEng antibodies or sEng-binding fragments thereof disclosed herein are diabodies, where two single chain antibodies are combined to form a diabody. Diabodies have two chains and two binding sites, each specific for sFlt-1 or sEng. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites.

In certain embodiments, the anti-sFlt-1 antibodies or sFlt-1-binding fragments thereof and/or the anti-sEng antibodies or sEng-binding fragments thereof disclosed herein are triabodies, where three single chain antibodies are combined to form a triabody. In triabodies, the amino acid terminus of a $V_L$ or $V_H$ domain is directly fused to the carboxyl terminus of a $V_L$ or $V_H$ domain, i.e., without any linker sequence. The triabody has three Fv heads with the polypeptides arranged in a cyclic, head-to-tail fashion.

In certain embodiments, the anti-sFlt-1 antibodies or sFlt-1-binding fragments thereof and/or the anti-sEng antibodies or sEng-binding fragments thereof disclosed herein are Fab fragments. Fab fragments are fragments of an antibody consisting of $V_L$, $C_L$, $V_H$, and $C_H1$ domains. Those generated following papain digestion simply are referred to as Fab and lack the heavy chain hinge region. Following pepsin digestion, various Fabs retaining the heavy chain hinge are generated. Those divalent fragments with the interchain disulfide bonds intact are referred to as $F(ab')_2$, while a monovalent Fab results when the disulfide bonds are not retained.

Thus, anti-sFlt-1 antibodies or sFlt-1-binding fragments thereof and/or anti-sEng antibodies or sEng-binding fragments thereof for use in the methods and systems disclosed herein include, but are not limited to, naturally occurring antibodies, bivalent fragments such as $(Fab')_2$, monovalent fragments such as Fab, single chain antibodies, single chain Fv (scFv), single domain antibodies, multivalent single chain antibodies, diabodies, triabodies, and the like that bind sFlt-1 or sEng, respectively.

In certain embodiments, specificity of antibodies, or fragments thereof, can be determined based on affinity and/or avidity. "Affinity", represented by the equilibrium constant for the dissociation of an antigen with an antibody ($K_d$), measures the binding strength between an antigenic determinant and an antibody-binding site. "Avidity" is the measure of the strength of binding between an antibody with its antigen. Avidity is related to both the affinity between an epitope with its antigen-binding site on the antibody, and the valence of the antibody, which refers to the number of antigen binding sites of a particular epitope. Antibodies typically bind with a dissociation constant ($K_d$) of $10^{-5}$ to $10^{-11}$ moles/liter (M). Any $K_d$ greater than $10^{-4}$ moles/liter is generally considered to indicate nonspecific binding. The lesser the value of the $K_d$, the stronger the binding strength between an antigenic determinant and the antibody binding site.

In certain embodiments, the anti-sFlt-1 antibodies or sFlt-1-binding fragments thereof disclosed herein bind sFlt-1 with a dissociation constant ($K_d$) of about $10^{-5}$ to $10^{-11}$ moles/liter, about $10^{-6}$ to $10^{-10}$ moles/liter, or about $10^{-7}$ to $10^{-9}$ moles/liter. In certain embodiments, the anti-sFlt-1 antibodies or sFlt-1-binding fragments thereof bind to sFlt-1 with a dissociation constant ($K_d$) of at least about $10^{-5}$ moles/liter, at least $10^{-6}$ moles/liter, at least $10^{-7}$ moles/liter, at least $10^{-8}$ moles/liter, at least $10^{-9}$ moles/liter, at least $10^{-10}$ moles/liter, or at least $10^{-11}$ moles/liter. In certain embodiments, the $K_d$ is from $10^{-9}$ moles/liter to $10^{-10}$ moles/liter. In certain embodiments, embodiments, the $K_d$ is from $10^{-10}$ moles/liter to $10^{-11}$ moles/liter. In certain embodiments, embodiments, the $K_d$ is from $10^{-8}$ moles/liter to $10^{-10}$ moles/liter. In certain embodiments, embodiments, the $K_d$ is from $10^{-7}$ moles/liter to $10^{-10}$ moles/liter.

In certain embodiments, the anti-sEng antibodies or sEng-binding fragments thereof disclosed herein bind sEng with a dissociation constant ($K_d$) of about $10^{-5}$ to $10^{-11}$ moles/liter, about $10^{-6}$ to $10^{-10}$ moles/liter, or about $10^{-7}$ to $10^{-9}$ moles/liter. In certain embodiments, the anti-sEng antibodies or sEng-binding fragments thereof bind to sEng with a dissociation constant ($K_d$) of at least about $10^{-5}$ moles/liter, at least $10^{-6}$ moles/liter, at least $10^{-7}$ moles/liter, at least $10^{-8}$ moles/liter, at least $10^{-9}$ moles/liter, at least $10^{-10}$ moles/liter, or at least $10^{-11}$ moles/liter. In certain embodiments, the $K_d$ is from $10^{-9}$ moles/liter to $10^{-10}$ moles/liter. In certain embodiments, embodiments, the $K_d$ is from $10^{-10}$ moles/liter to $10^{-11}$ moles/liter. In certain embodiments, embodiments, the $K_d$ is from $10^{-8}$ moles/liter to $10^{-10}$ moles/liter. In certain embodiments, embodiments, the $K_d$ is from $10^{-7}$ moles/liter to $10^{-10}$ moles/liter.

The anti-sFlt-1 antibodies or sFlt-1-binding fragments thereof and anti-sEng antibodies or sEng-binding fragments disclosed herein further include those for which binding characteristics have been improved by direct mutation, methods of affinity maturation, phage display, or chain shuffling. Affinity and specificity can be modified or improved by mutating CDRs and screening for antigen binding sites having the desired characteristics (see, e.g., Yang et al., J. Mol. Biol., 254: 392-403 (1995)). CDRs can be mutated in a variety of ways. One way is to randomize individual residues or combinations of residues so that in a population of otherwise identical antigen binding sites, all twenty amino acids are found at particular positions. Alternatively, mutations may be induced over a range of CDR residues by error-prone PCR or other mutagenic methods (see, e.g., Hawkins et al., J. Mol. Biol., 226: 889-896 (1992)). For example, phage display vectors containing heavy and light chain variable region genes can be propagated in mutator strains of E. coli (see, e.g., Low et al., J. Mol. Biol., 250: 359-368 (1996)). These methods of mutagenesis are illustrative of the many methods known to one of skill in the art.

Antibodies disclosed herein can be obtained by standard hybridoma technology (e.g., Harlow & Lane, ed., Antibodies: A Laboratory Manual, Cold Spring Harbor, 211-213 (1998), which is incorporated by reference herein) or by using transgenic mice (e.g., KM mice, originally from Medarex, San Jose, Calif.) that produce human immunoglobulin gamma heavy and kappa light chains. In certain mice known in the art, a substantial portion of the human antibody producing genome is inserted into the genome of the mice, and the mice are rendered deficient in the production of endogenous murine antibodies. Such mice may be immunized with part or all of sFlt-1 (e.g., human sFlt-1) or with part or all of sEng (e.g., human sEng), optionally in a suitable adjuvant, e.g., complete or incomplete Freund's adjuvant.

Methods for the preparation of antibodies suitable for use in the methods and systems disclosed herein are well known in the art and are described, e.g., in U.S. Pat. Nos. 6,054,297; 5,821,337; 6,365,157; and 6,165,464; U.S. Patent Application Publication No. 2006/0067937; International Patent Publication WO 06/034507; which are incorporated herein by reference.

The anti-sFlt-1 antibodies or sFlt-1-binding fragments thereof and the anti-sEng antibodies or sEng-binding fragments thereof disclosed herein may include polyclonal antibodies, monoclonal antibodies, humanized or chimeric antibodies, Fv fragments, single chain Fv fragments, Fab fragments, or F(ab')₂ fragments. In certain embodiments, the antibodies are mouse monoclonal antibodies. The anti-sFlt-1 antibodies or sFlt-1-binding fragments thereof and the anti-sEng antibodies or sEng-binding fragments thereof disclosed herein may include a variety of antibody isotypes, such as IgG1, IgG2, IgG3, IgG4, IgM, IgA1, IgA2, secretory IgA, IgD, and IgE.

"Chimeric antibody" refers to a polypeptide comprising at least the antigen-binding portion of an antibody molecule linked to at least part of another protein (typically an immunoglobulin constant domain).

"Humanized antibody" refers to an antibody with a framework region (FR) having substantially the amino acid sequence of a human immunoglobulin and a complementarity determining region (CDR) having substantially the amino acid sequence of a non-human immunoglobulin (the "import" sequences). Generally, a humanized antibody has one or more amino acid residues introduced into it from a source that is non-human. The humanized antibody will usually comprise substantially all of at least one, and typically two, variable domains (Fab, Fab', F(ab')₂, Fabc, Fv) in which all or substantially all of the CDR regions correspond to those of a non-human immunoglobulin and all or substantially all of the FR regions are those of a human immunoglobulin or a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains. The FR and CDR regions of the humanized antibody need not correspond precisely to the parental sequences, e.g., the import CDR or the human or consensus human FR may be mutagenized by substitution, insertion, or deletion of at least one residue so that the CDR or FR residue at that site does not correspond to either the consensus or the import sequence. Such mutations, however, will not be extensive. Usually, at least 75%, preferably 90%, and most preferably at least 95% of the humanized antibody residues will correspond to those of the parental FR and CDR sequences.

The anti-sFlt-1 antibodies or sFlt-1-binding fragments thereof and the anti-sEng antibodies or sEng-binding fragments thereof disclosed herein may be obtained directly from hybridomas, which express the anti-sFlt-1 antibodies or sFlt-1-binding fragments thereof or the anti-sEng antibodies or sEng-binding fragments thereof disclosed herein, or may be cloned and recombinantly expressed in suitable host cells (e.g., CHO cells, NS/0 cells, HEK293 cells). Suitable host cells include plant cells, mammalian cells, and microorganisms such as E. coli and yeast. Alternatively, the anti-sFlt-1 antibodies or sFlt-1-binding fragments thereof and the anti-sEng antibodies or sEng-binding fragments thereof disclosed herein may be produced recombinantly in a transgenic non-human plant or animal, e.g., a transgenic mouse.

In certain embodiments, the anti-sFlt-1 antibodies or sFlt-1-binding fragments thereof and the anti-sEng antibodies or sEng-binding fragments thereof may be modified prior to, or after, attachment or binding to a solid support. Possible modifications include glycosylation, deglycosylation, aglycosylation, acetylation, pegylation, phosphorylation, amidation, derivatization with protecting or blocking groups, proteolytic cleavage, or linkage to a cellular ligand or other protein. In certain embodiments, the anti-sFlt-1 antibodies or sFlt-1-binding fragments thereof and the anti-sEng antibodies or sEng-binding fragments thereof may contain one or more non-classical amino acids.

Also provided herein are nucleic acids encoding the anti-sFlt-1 antibodies or sFlt-1-binding fragments thereof and the anti-sEng antibodies or sEng-binding fragments thereof disclosed herein, as well as vectors, host cells, and expression systems. The term "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

In one embodiment, provided is a nucleic acid encoding a variable chain sequence comprising SEQ ID NO:14 and/or SEQ ID NO:16. In one embodiment, provided is a nucleic acid comprising SEQ ID NO:13 and/or SEQ ID NO:15.

In one embodiment, provided is a nucleic acid encoding a variable chain sequence comprising SEQ ID NO:22 and/or SEQ ID NO:24. In one embodiment, provided is a nucleic acid comprising SEQ ID NO:21 and/or SEQ ID NO:23.

In one embodiment, provided is a nucleic acid encoding a heavy chain sequence comprising SEQ ID NO:18. In one embodiment, provided is a nucleic acid encoding a light chain sequence comprising SEQ ID NO:20. In one embodiment, provided is a nucleic acid comprising SEQ ID NO:17 and/or SEQ ID NO:19.

In one embodiment, provided is a nucleic acid encoding a heavy chain sequence comprising SEQ ID NO:26. In one embodiment, provided is a nucleic acid encoding a light chain sequence comprising SEQ ID NO:28. In one embodiment, provided is a nucleic acid comprising SEQ ID NO:25 and/or SEQ ID NO:27.

The nucleic acids encoding the anti-sFlt-1 antibodies or sFlt-1-binding fragments thereof and/or the anti-sEng antibodies or sEng-binding fragments thereof disclosed herein may be, e.g., DNA, cDNA, RNA, synthetically produced DNA or RNA, or a recombinantly produced chimeric nucleic acid molecule comprising any of those polynucleotides either alone or in combination. For example, provided is an expression vector comprising a polynucleotide sequence encoding an anti-sFlt-1 antibody or sFlt-1-binding fragment thereof or an anti-sEng antibody or sEng-binding fragment thereof disclosed herein operably linked to expression control sequences suitable for expression in a eukaryotic and/or prokaryotic host cell.

The term "vector" refers to a nucleic acid molecule capable of transporting another nucleic acid to which it has been linked. A "vector" includes, but is not limited to, a viral vector, a plasmid, a RNA vector or a linear or circular DNA or RNA molecule, which may consist of a chromosomal, non-chromosomal, semi-synthetic or synthetic nucleic acids. In some embodiments, the employed vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g., adeno associated viruses, AAV), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, and spumavirus.

A variety of expression vectors have been developed for the efficient synthesis of antibodies and antigen binding fragments thereof in prokaryotic cells such as bacteria and in eukaryotic systems, including but not limited to yeast and mammalian cell culture systems have been developed. The vectors can comprise segments of chromosomal, non-chromosomal and synthetic DNA sequences.

Also provided are cells comprising expression vectors for the expression of the contemplated anti-sFlt-1 antibodies or sFlt-1-binding fragments thereof and anti-sEng antibodies or sEng-binding fragments thereof.

In one aspect, the anti-sFlt-1 antibodies or sFlt-1-binding fragments and anti-sEng antibodies or sEng-binding fragments thereof disclosed herein are suitable for ex vivo treatment of an sFlt-1- and sEng-related disorder. "Suitable" means that the antibodies effectively reduce the concentration of sFlt-1 and sEng in a subject's blood or plasma when used in an effective amount for an effective time. For example, using a 50 mL/minute flow rate, 5 liters of plasma (approximately 1.5 human blood volumes) would be processed in 100 minutes or less. In one embodiment, a volumetric flow rate of 1 mL/min is applied to a 1 mL column. This is comparable to a volumetric 50 mL/min flow rate using a 50 mL column (and comparable to a residence time of 1 min). In other embodiments, a volumetric flow rate of 0.25, 0.5, or 2 ml/min is applied to a 1 ml column.

In one embodiment, the volumetric flow rate is between 0.05 and 100 mL/min. In one embodiment, the volumetric flow rate is between 0.1 mL/min and 10 mL/min. In one embodiment, the volumetric flow rate is between 0.25 mL/min and 5 mL/min. In one embodiment, the volumetric flow rate is between 0.5 mL/min and 3 mL/min. In one embodiment, the volumetric flow rate is 0.05 mL/min, 0.1 mL/min, 0.25 mL/min, 0.5 mL/min, 1 mL/min, 1.5 mL/min, 2 mL/min, 2.5 mL/min, 3 mL/min, 3.5 mL/min, 4 mL/min, 4.5 mL/min, 5 mL/min, 10 mL/min, 25 mL/min, 50 mL/min, or 100 mL/min. In one embodiment, the volumetric flow rate is less than 0.1 mL/min, less than 0.25 mL/min, less than 0.5 mL/min, less than 1 mL/min, less than 1.5 mL/min, less than 2 mL/min, less than 2.5 mL/min, less than 3 mL/min, less than 3.5 mL/min, less than 4 mL/min, less than 4.5 mL/min, less than 5 mL/min, less than 10 mL/min, less than 25 mL/min, less than 50 mL/min, or less than 100 mL/min.

In one embodiment, the linear flow rate is between 5 cm/h and 300 cm/h. In one embodiment, the linear flow rate is between 5 cm/h and 100 cm/h. In one embodiment, the linear flow rate is between 5 cm/h and 40 cm/h. In one embodiment, the linear flow rate is between 10 cm/h and 250 cm/h. In one embodiment, the linear flow rate is 9 cm/h, 18 cm/h, 38 cm/h, 73 cm/h, 76 cm/h, 113 cm/h, or 230 cm/h. In one embodiment, the linear flow rate is less than 9 cm/h, less than 18 cm/h, less than 38 cm/h, less than 73 cm/h, less than 76 cm/h, less than 113 cm/h, or less than 230 cm/h. In one embodiment, the linear flow rate is 10 cm/h, 20 cm/h, 30 cm/h, 40 cm/h, 50 cm/h, 70 cm/h, 80 cm/h, or 100 cm/h, 110 cm/h, 120 cm/h, 150 cm/h, 180 cm/h, 240 cm/h, or 300 cm/h. In one embodiment, the linear flow rate is less than 10 cm/h, less than 20 cm/h, less than 30 cm/h, less than 40 cm/h, less than 50 cm/h, less than 70 cm/h, less than 80 cm/h, less than 100 cm/h, less than 110 cm/h, less than 120 cm/h, less than 150 cm/h, less than 180 cm/h, less than 240 cm/h, or less than 300 cm/h.

The residence time of a given material, such as plasma, flowing through a volume, such as a column, is a measure of how much time the matter spends in the volume. Residence time depends on the flow velocity and the bed height of the column bed. In one embodiment, the residence time is between 0.25 min and 5 min. In one embodiment, the residence time is between 0.5 min and 2 min. In one embodiment, the residence time is between 2 min and 5 min. In one embodiment, the residence time is 0.25 min, 0.33 min, 0.5 min, 0.67 min, 1 min, 1.5 min, 2 min, 2.5 min, 3 min, 3.5 min, 4 min, 4.5 min, or 5 min. In one embodiment, the residence time is at least 0.33 min, at least 0.5 min, at least 0.67 min, at least 1 min, at least 1.5 min, at least 2 min, at least 2.5 min, at least 3 min, at least 3.5 min, at least 4 min, at least 4.5 min, or at least 5 min.

The anti-sFlt-1 antibodies or sFlt-1-binding fragments and/or anti-sEng antibodies or sEng-binding fragments thereof disclosed herein can be linked to Sepharose beads in amounts of, for example, 0.025, 0.05, 0.1, 0.2, 0.25, 0.4, 0.5, 0.8, 1, 2, or 5 mg antibody/ml beads. In some embodiments, the anti-sFlt-1 antibodies or sFlt-1-binding fragments and/or anti-sEng antibodies or sEng-binding fragments thereof disclosed herein are linked to Sepharose beads in amounts of at least 0.025, at least 0.05, at least 0.1, at least 0.2, at least 0.25, at least 0.4, at least 0.5, at least 0.8, at least 1, at least 2, or at least 5 mg antibody/ml beads.

In some embodiments, for example for research purposes, columns of various dimensions containing 0.1-50 ml of Sepharose beads coupled with anti-sFlt-1 antibodies or sFlt-1-binding fragments thereof and anti-sEng antibodies or sEng-binding fragments thereof may be tested for their ability to deplete recombinant sFlt-1 and sEng spiked into buffered solutions or animal serum or human plasma, or native sFlt-1 and sEng in amniotic fluid or blood plasma of pre-eclampsia patients. The columns provided herein may have various aspect ratios (length:width). In some embodiments, the aspect ratio is about 1:1, about 2:1, about 5:1, about 10:1, about 20:1, about 30:1, about 40:1, or about 50:1.

In some embodiments, the sFlt-1 and/or sEng depletion experiments are conducted with columns containing anti-sFlt-1 antibody- and anti-sEng antibody-coupled Sepharose beads at 0.025-20 mg of antibodies per 1 ml of beads (0.065-52 billion antibody molecules per single bead), at flow rates of 0.05-50 ml/min, at linear flow rates of 10-300 cm/h, and residence times of 0.25-5 minutes. In some embodiments, 1 to 400 times the column bed volumes of buffered solutions, serum or plasma containing sFlt-1 and sEng are applied to the columns at anti-sFlt-1 antibody: sFlt-1 ratios and/or anti-sEng antibody:sEng ratios of 5:1 to 5,000:1 (w/w), or molar ratios of 1.25:1 to 1,250:1. Under these ranges of conditions, columns containing Sepharose beads coupled with anti-sFlt-1 antibodies and anti-sEng antibodies is expected to deplete 50 to 100% of sFlt-1 and sEng in buffered solutions, serum or plasma.

In some embodiments, the antibody:target ratio in the column is 100:1 (w/w), 200:1 (w/w), 300:1 (w/w), 400:1 (w/w), 500:1 (w/w), 600:1 (w/w), 700:1 (w/w), 800:1 (w/w), 900:1 (w/w), 1,000:1 (w/w), 1,100:1 (w/w), 1,200:1 (w/w), 1,300:1 (w/w), 1,400:1 (w/w), 1,500:1 (w/w), 2,000:1 (w/w), 3,000:1 (w/w), 4,000:1 (w/w), or 5,000:1 (w/w), wherein the target is sFlt-1 or sEng. In some embodiments, the antibody:target ratio is at least 100:1 (w/w), at least 200:1 (w/w), at least 300:1 (w/w), at least 400:1 (w/w), at least 500:1 (w/w), at least 600:1 (w/w), at least 700:1 (w/w), at least 800:1 (w/w), at least 900:1 (w/w), at least 1,000:1 (w/w), at least 1,100:1 (w/w), at least 1,200:1 (w/w), at least 1,300:1 (w/w), at least 1,400:1 (w/w), at least 1,500:1 (w/w), at least 2,000:1 (w/w), at least 3,000:1 (w/w), at least 4,000:1 (w/w), or at least 5,000:1 (w/w), wherein the target is sFlt-1 or sEng.

In some embodiments, the antibody:target molar ratio in the column is 1.25:1, 2:1, 3:1, 4:1, 5:1, 10:1, 15:1, 20:1, 25:1, 30:1, 50:1, 75:1, 100:1, 125:1, 150:1, 200:1, 250:1, 300:1, 400:1, or 500:1, wherein the target is sFlt-1 or sEng. In some embodiments, the antibody:target molar ratio is at least 1.25:1, at least 2:1, at least 3:1, at least 4:1, at least 5:1, at least 10:1, at least 15:1, at least 20:1, at least 25:1, at least 30:1, at least 50:1, at least 75:1, at least 100:1, at least 125:1, at least 150:1, at least 200:1, at least 250:1, at least 300:1, at least 400:1, or at least 500:1, wherein the target is sFlt-1 or sEng.

In other embodiments, for clinical treatments, columns of various dimensions containing 25 to 750 ml of Sepharose beads coupled with anti-sFlt-1 antibodies and sFlt binding fragments and anti-sEng antibodies or sEng-binding fragments thereof are used to deplete native sFlt-1 and sEng of various isoforms from blood plasma of patients suffering from diseases associated with high levels of sFlt-1 and/or sEng in blood, including pregnancy-related hypertensive disorders like pre-eclampsia, eclampsia, HELLP syndrome, or postpartum hypertension, and non-hypertensive sFlt-1 and sEng-related disorders.

In some embodiments, the columns contain anti-sFlt-1 antibody- and anti-sEng antibody-coupled Sepharose beads at 0.1-5 mg of antibodies per 1 ml of beads (5-250 mg per 50 ml beads; 0.26-13 billion antibody molecules per single bead), at flow rates of 10-100 ml/min, at linear flow rates of 10-300 cm/h, and residence times of 0.2-5 minutes. Patients with average weight will have about 8 Liters of blood circulating in their body (about 4 Liters of plasma). In some embodiments, about 0.25-3 times the total body plasma volume (1-12 Liters of plasma), which corresponds to 20 to 240 times the column bed volumes of blood plasma (for a 50 ml column), containing 0.04-0.48 mg of native sFlt-1 or sEng (for a patient with 40 ng/ml sFlt-1 or sEng level in plasma) of various forms, are applied to the columns containing anti-sFlt-1 antibody- and anti-sEng antibody-coupled beads at antibody to target ratios of 50:1 to 2,000:1 (w/w), or molar ratios of 12.5:1 to 500:1. Under these ranges of conditions, columns containing Sepharose beads coupled with anti-sFlt-1 antibodies or sFlt-1-binding fragments thereof and anti-sEng antibodies or sEng-binding fragments thereof are expected to deplete 50 to 100% of sFlt-1 and sEng from plasma of patients with high sFlt-1 and/or sEng levels in their blood.

In one aspect, provided is a method of treating or preventing a pregnancy-related hypertensive disorder in a subject in need thereof, the method comprising providing ex vivo to the subject an anti-sEng antibody or sEng-binding fragment thereof and an anti-sFlt-1 antibody or sFlt-1-binding fragment thereof. In one embodiment, the anti-sEng antibody or sEng-binding fragment thereof and the anti-sFlt-1 antibody or sFlt-1-binding fragment thereof are provided together in a single column.

In another embodiment of the methods disclosed herein, the anti-sFlt-1 antibody or sFlt-1-binding fragment thereof is provided in one column, and the anti-sEng antibody or sEng-binding fragment thereof is provided in another column. As such, also contemplated is a combination of a column comprising an anti-sFlt-1 antibody or sFlt-1-binding fragment thereof and a column comprising an anti-sEng antibody or sEng-binding fragment thereof, wherein the combination may be used in the methods disclosed herein.

In one embodiment, the anti-sFlt-1 column and the anti-sEng column are used consecutively to deplete the blood or plasma of a subject in need thereof of sFlt-1 and sEng. In one embodiment, the anti-sFlt-1 column is used before the anti-sEng column to deplete the blood or plasma of a subject in need thereof of sFlt-1 and sEng. In one embodiment, the anti-sEng column is used before the anti-sFlt-1 column to deplete the blood or plasma of a subject in need thereof of sFlt-1 and sEng. In one embodiment, the anti-sFlt-1 column and the anti-sEng column are used concurrently to deplete the blood or plasma of a subject in need thereof of sFlt-1 and sEng. In one embodiment, the anti-sFlt-1 column and the anti-sEng column are physically connected. In one embodiment, more than one anti-sFlt-1 column and/or more than one anti-sEng column is used.

In one embodiment, provided is a method of treating or preventing a disorder associated with sFlt-1 and sEng, such as a pregnancy-related hypertensive disorder, in a subject comprising providing ex vivo to the subject an anti-sFlt antibody or sFlt-1-binding fragment thereof and an anti-sEng antibody or sEng-binding fragment thereof, wherein the anti-sFlt antibody or sFlt-1-binding fragment thereof and the anti-sEng antibody or sEng-binding fragment thereof are bound to a solid support, and wherein the molar antibody to target (sEng or sFlt-1 respectively) ratio is 500.

In one embodiment, provided is a method of treating or preventing a disorder associated with sFlt-1 and sEng, such as a pregnancy-related hypertensive disorder, in a subject in need thereof, the method comprising providing ex vivo to the subject an anti-sFlt antibody or sFlt-1-binding fragment thereof and an anti-sEng antibody or sEng-binding fragment thereof, wherein the anti-sFlt antibody or sFlt-1-binding fragment thereof and the anti-sEng antibody or sEng-binding fragment thereof are bound to a solid support, and wherein the molar antibody to target (sEng or sFlt-1 respectively) ratio is 400.

In one embodiment, provided is a method of treating or preventing a disorder associated with sFlt-1 and sEng, such as a pregnancy-related hypertensive disorder, in a subject in need thereof, the method comprising providing ex vivo to the subject an anti-sFlt antibody or sFlt-1-binding fragment thereof and an anti-sEng antibody or sEng-binding fragment thereof, wherein the anti-sFlt antibody or sFlt-1-binding fragment thereof and the anti-sEng antibody or sEng-binding fragment thereof are bound to a solid support, and wherein the molar antibody to target (sEng or sFlt-1 respectively) ratio is 250.

In one embodiment, provided is a method of treating or preventing a disorder associated with sFlt-1 and sEng, such as a pregnancy-related hypertensive disorder, in a subject in need thereof, the method comprising providing ex vivo to the subject an anti-sFlt antibody or sFlt-1-binding fragment thereof and an anti-sEng antibody or sEng-binding fragment thereof, wherein the anti-sFlt antibody or sFlt-1-binding fragment thereof and the anti-sEng antibody or sEng-binding fragment thereof are bound to a solid support, and wherein the molar antibody to target (sEng or sFlt-1 respectively) ratio is 100.

In still other embodiments, provided is a method of treating or preventing a disorder associated with sFlt-1 and sEng, such as a pregnancy-related hypertensive disorder, in a subject in need thereof, the method comprising providing ex vivo to the subject an anti-sFlt antibody or sFlt-1-binding fragment thereof and an anti-sEng antibody or sEng-binding fragment thereof, wherein the anti-sFlt antibody or sFlt-1-binding fragment thereof and the anti-sEng antibody or sEng-binding fragment thereof are bound to a solid support, and wherein the molar antibody to target (sEng or sFlt-1 respectively) ratio is 50, 25, or 12.5.

In some embodiments, the anti-sFlt-1 antibodies or sFlt-1-binding fragments thereof and sEng antibodies or sEng-binding fragments thereof disclosed herein efficiently deplete sFlt-1 and sEng in blood or plasma from a subject. The sFlt-1 and the sEng can be soluble and/or in micropar-ticles circulating in the bloodstream. In some embodiments, the anti-sFlt antibody or sFlt-1-binding fragment thereof depletes at least 70%, or at least 80%, or at least 90%, or at least 95%, or at least 99%, or from 70% to 80%, or from 80% to 90%, or from 90% to 95%, or from 95% to 99% of sFlt-1 from human blood or plasma in an in vitro analysis. In some embodiments, the anti-sEng antibody or sEng-binding fragment thereof depletes at least 70%, or at least 80%, or at least 90%, or at least 95%, or at least 99%, or from 70% to 80%, or from 80% to 90%, or from 90% to 95%, or from 95% to 99% of sEng from human blood or plasma in an in vitro analysis.

In another embodiment, provided is an analysis method, wherein human serum is spiked with sFlt-1 and/or sEng. In certain embodiments, the analysis is performed using Sep-harose bead-bound anti-sFlt-1 antibodies or sFlt-1-binding fragments thereof and anti-sEng antibodies or sEng-binding fragments thereof mixed in sFlt-1 and/or sEng-spiked plasma. In certain embodiments, the analysis is performed over a time period that replicates a residence time on a clinical column of 0.25, 0.5, 1, 1.5, 2, 2.5, 3, 4, or 5 minutes. Such an analysis can be performed using a solution of bead-bound anti-sFlt-1 antibodies or sFlt-1-binding frag-ments thereof and bead-bound anti-sEng antibodies or sEng-binding fragments in a column and sFlt-1 and/or sEng-spiked plasma applied at a flow rate to obtain a desired residence time. Alternatively, the analysis could be per-formed using sFlt-1 and/or sEng spiked in amniotic fluid, serum (e.g., horse serum), or a buffer solution (e.g., phos-phate buffered saline, PBS), but plasma, particularly human plasma, is preferred. The analysis can be performed using anti-sFlt-1 antibodies or sFlt-1-binding fragments thereof and anti-sEng antibodies or sEng-binding fragments thereof bound to a column support (e.g., Sepharose beads) at various densities and sFlt-1 and/or sEng spiked in plasma at various concentrations. The anti-sFlt-1 antibodies or sFlt-1-binding fragments thereof and/or the anti-sEng antibodies or sEng-binding fragments thereof can be linked to Sepharose beads on amounts of 0.025, 0.050, 0.25, 0.5, 1, 2, or 5 mg/bead. The volumetric flow rate can be 0.05, 0.1, 0.25, 0.5, 1, 2, 2.5, 5, 10, 25, 50, or 100 ml/min, and linear flow rates can be 10, 20, 30, 50, 75, 100, 150, 180, 240, or 300 cm/hr.

In certain embodiments, when an antibody disclosed herein is bound to a solid support (e.g., Sepharose beads), and contacted with a solution containing sFlt-1 and sEng such that the antibody to target ratio is 50, the anti-sFlt-1 antibody or sFlt-1-binding fragment thereof depletes (binds to) at least 70%, or at least 80%, or at least 90%, or at least 95% of sFlt-1, and the anti-sEng antibody or sEng-binding fragment thereof depletes (binds to) at least 70%, or at least 80%, or at least 90%, or at least 95% of sEng. In certain embodiments, the sFlt-1 antibody or sFlt-1-binding frag-ment thereof depletes from 70% to 80%, of from 80% to 90%, or from 90% to 95%, of from 95 to 99% of sFlt-1. In certain embodiments, the sEng antibody or sEng-binding fragment thereof depletes from 70% to 80%, of from 80% to 90%, or from 90% to 95%, of from 95 to 99% of sEng. The solution can be blood, plasma, serum, or a buffer solution.

In certain embodiments, when an anti-sFlt-1 antibody or sFlt-1-binding fragment thereof disclosed herein is bound to a solid support (e.g., Sepharose beads), and contacted with a solution containing sFlt-1 and sFlt-1 such that the anti-sFlt-1 antibody or sFlt-1-binding fragment thereof to sFlt-1 ratio is 100, the anti-sFlt-1 antibody or sFlt-1-binding frag-ment thereof depletes at least 70%, or at least 80%, or at least 90%, or at least 95% of sFlt-1. In certain embodiments, the anti-sFlt-1 antibody or sFlt-1-binding fragment thereof depletes from 70% to 80%, of from 80% to 90%, or from 90% to 95%, of from 95 to 99% of sFlt-1. In certain embodiments, when an anti-sFlt-1 antibody or sFlt-1-bind-ing fragment thereof disclosed herein is bound to a solid support (e.g., Sepharose beads), and contacted with a solu-tion containing sFlt-1 and sFlt-1 such that the anti-sFlt-1 antibody or sFlt-1-binding fragment thereof to sFlt-1 ratio is 250, the anti-sFlt-1 antibody or sFlt-1-binding fragment thereof depletes at least 70%, or at least 80%, or at least 90%, or at least 95% of sFlt-1. In certain embodiments, the anti-sFlt-1 antibody or sFlt-1-binding fragment thereof depletes from 70% to 80%, of from 80% to 90%, or from 90% to 95%, of from 95 to 99% of sFlt-1. In certain embodiments, when an anti-sFlt-1 antibody or sFlt-1-binding fragment thereof disclosed herein is bound to a solid support (e.g., Sepharose beads), and contacted with a solution containing sFlt-1 and sFlt-1 such that the anti-sFlt-1 antibody or sFlt-1-binding fragment thereof to sFlt-1 ratio is 400, the anti-sFlt-1 antibody or sFlt-1-binding fragment thereof depletes at least 70%, or at least 80%, or at least 90%, or at least 95% of sFlt-1. In certain embodiments, the anti-sFlt-1 antibody or sFlt-1-binding fragment thereof depletes from 70% to 80%, of from 80% to 90%, or from 90% to 95%, of from 95 to 99% of sFlt-1.

In certain embodiments, when an anti-sEng antibody or sEng-binding fragment thereof disclosed herein is bound to a solid support (e.g., Sepharose beads), and contacted with a solution containing sFlt-1 and sEng such that the anti-sEng antibody or sEng-binding fragment thereof to sEng ratio is 100, the anti-sEng antibody or sEng-binding fragment thereof depletes at least 70%, or at least 80%, or at least 90%, or at least 95% of sEng. In certain embodiments, the anti-sEng antibody or sEng-binding fragment thereof depletes from 70% to 80%, of from 80% to 90%, or from 90% to 95%, of from 95 to 99% of sEng. In certain embodiments, when an anti-sEng antibody or sEng-binding fragment thereof disclosed herein is bound to a solid support (e.g., Sepharose beads), and contacted with a solution containing sFlt-1 and sEng such that the anti-sEng antibody or sEng-binding fragment thereof to sEng ratio is 250, the anti-sEng antibody or sEng-binding fragment thereof depletes at least 70%, or at least 80%, or at least 90%, or at least 95% of sEng. In certain embodiments, the anti-sEng antibody or sEng-binding fragment thereof depletes from 70% to 80%, of from 80% to 90%, or from 90% to 95%, of from 95 to 99% of sEng. In certain embodiments, when an anti-sEng antibody or sEng-binding fragment thereof disclosed herein is bound to a solid support (e.g., Sepharose beads), and contacted with a solution containing sFlt-1 and sEng such that the anti-sEng antibody or sEng-binding fragment thereof to sEng ratio is 400, the anti-sEng antibody or sEng-binding fragment thereof depletes at least 70%, or at least 80%, or at least 90%, or at least 95% of sEng. In certain embodiments, the anti-sEng antibody or sEng-binding fragment thereof depletes from 70% to 80%, of from 80% to 90%, or from 90% to 95%, of from 95 to 99% of sEng.

In certain embodiments, the anti-sFlt-1 antibody or sFlt-1-binding fragment thereof is capable, under suitable conditions, of reducing the concentration of sFlt-1 in the subject's blood or plasma containing sFlt-1 to less than about 100 ng/ml, less than about 90 ng/ml, less than about 80 ng/ml, less than about 70 ng/ml, less than about 60 ng/ml, less than about 50 ng/ml, less than about 40 ng/ml, less than about 25 ng/ml, less than about 10 ng/ml, less than about 5 ng/ml, less than about 4 ng/ml, less than about 3 ng/ml, less than about 2 ng/ml, less than about 1 ng/ml, less than about 0.75 ng/ml, or less than about 0.5 ng/ml. In certain embodiments, the anti-sEng antibody or sEng-binding fragment thereof is capable, under suitable conditions, of reducing the concentration of sEng in the subject's blood or plasma containing sEng to less than about 100 ng/ml, less than about 90 ng/ml, less than about 80 ng/ml, less than about 70 ng/ml, less than about 60 ng/ml, less than about 50 ng/ml, less than about 40 ng/ml, less than about 25 ng/ml, less than about 10 ng/ml, less than about 5 ng/ml, less than about 4 ng/ml, less than about 3 ng/ml, less than about 2 ng/ml, less than about 1 ng/ml, less than about 0.75 ng/ml, or less than about 0.5 ng/ml.

In certain embodiments, an sFlt-1 molecule is removed from blood plasma by immobilization to a solid support, for example, using an anti-sFlt-1 antibody or sFlt-1-binding fragment thereof. When sFlt-1 is immobilized to a solid support, ligand binding is less favored compared to the case where sFlt-1 is free in solution. Accordingly, sFlt-1 levels are reduced in the subject, and any reduction of circulating sFlt-1 ligand may be insubstantial. In certain embodiments, an sEng molecule is removed from blood plasma by immobilization to a solid support, for example, using an anti-sEng antibody or sEng-binding fragment thereof. When sEng is immobilized to a solid support, ligand binding is less favored compared to the case where sEng is free in solution. Accordingly, sEng levels are reduced in the subject, and any reduction of circulating sEng ligand may be insubstantial.

In certain embodiments, provided are methods comprising:

(a) removing blood from the subject, (b) passing the blood or a component thereof over one or more solid supports to which are bound (i) anti-sFlt-1 antibodies or sFlt-1-binding fragments thereof or sFlt-1 ligands, and (ii) anti-sEng antibodies or sEng-binding fragments thereof or sEng ligands to decrease the levels of sFlt-1 and sEng in the blood or component thereof, and (c) returning the blood or component thereof to the subject's body.

In certain embodiments, the blood is separated into plasma and cellular components and only the plasma is contacted with the anti-sFlt-1 antibodies or sFlt-1-binding fragments thereof and the anti-sEng antibodies or sEng-binding fragments thereof, while the cellular components are returned to the subject without such contact or, in certain embodiments, disposed of rather than returned to the subject.

Accordingly, in certain embodiments, the method comprises removing a volume of the subject's blood, separating the blood into plasma and cellular components, bringing the plasma into contact with the anti-sFlt-1 antibodies or sFlt-1-binding fragments thereof and the anti-sEng antibodies or sEng-binding fragments thereof to bind sFlt-1 and sEng in the plasma to the anti-sFlt-1 antibodies or sFlt-1-binding fragments thereof and to the anti-sEng antibodies or sEng-binding fragments thereof, thereby decreasing the amounts of sFlt-1 and sEng in the subject's plasma, returning the plasma to the subject, and, optionally, returning the cellular components to the subject.

When practicing the above embodiment, the cellular components may be returned to the subject at any time. That is, the cellular components may be returned to the subject before the plasma is contacted with the anti-sFlt-1 antibodies or sFlt-1-binding fragments thereof and the anti-sEng antibodies or sEng-binding fragments thereof. The cellular components may be returned to the subject after the plasma is contacted with the anti-sFlt-1 antibodies or sFlt-1-binding fragments thereof and the anti-sEng antibodies or sEng-binding fragments thereof. In certain embodiments, the cellular components may be combined with the plasma after the plasma has been contacted with the anti-sFlt-1 antibodies or sFlt-1-binding fragments thereof and the anti-sEng antibodies or sEng-binding fragments thereof, and the combined cellular components and plasma are returned to the subject at the same time, through the same conduit system and/or the same return device.

In certain embodiments, provided are methods for treating and/or preventing an sFlt-1 and sEng-related disorder, wherein the sFlt-1 and sEng-related disorder is a pregnancy-related hypertensive disorder. In some embodiments, the pregnancy-related hypertensive disorder is eclampsia, pre-eclampsia, HELLP syndrome, or postpartum hypertension. In certain embodiments, the pregnancy-related hypertensive disorder is pre-eclampsia. In certain embodiments, the pregnancy-related hypertensive disorder is HELLP syndrome.

In certain embodiments, provided are methods for treating and/or preventing a sFlt-1 and sEng-related disorder, wherein the sFlt-1 and sEng-related disorder a non-hypertensive sFlt-1 and sEng-related disorder. In some embodiments, the non-hypertensive sFlt-1 and sEng-related disorder is chronic kidney disease or systemic sclerosis (scleroderma). sEng levels are typically elevated during the last several weeks of a normal pregnancy, and may not be accompanied by a hypertensive disorder. Accordingly, in some embodiments, the non-hypertensive sFlt-1 and sEng-related disorder is a non-hypertensive sFlt-1 and sEng-related disorder of late stage pregnancy and labor. In one embodiment, the non-hypertensive sFlt-1 and sEng-related disorder of late stage pregnancy and labor is pre-term labor.

In certain embodiments, the subject is a pregnant human, a postpartum human, or a pregnant or postpartum non-human (e.g., a cow, a horse, a sheep, a pig, a goat, a dog, or a cat). In certain embodiments, the subject is a pregnant human or a postpartum human. In certain embodiments, the subject is a pregnant human.

In certain embodiments, the methods disclosed herein may be practiced on a subject who is being treated with standard pre-eclampsia or eclampsia therapies. Such standard therapies are known to the skilled artisan and include the methods described in U.S. Patent Application Publication No. US 2004/0126828; U.S. Patent Application Publication No. US 2005/0025762; U.S. Patent Application Publication No. US 2005/0170444; and U.S. Patent Application Publication No. US 2006/0067937 as well as in International Patent Publication WO 2004/008946; International Patent Publication WO 2005/077007; and International Patent Publication WO 06/034507.

The methods disclosed herein may be practiced using a combination of different sFlt-1 and sEng-binding substances. For example, two or more of anti-sFlt-1 antibodies or sFlt-1-binding fragments thereof or sFlt-1 ligands may be used. Likewise, two or more of anti-sEng antibodies or sEng-binding fragments thereof or sEng ligands may be used.

The methods disclosed herein may be practiced on a subject who is being treated with chronic hypertension medications. Medications used for the treatment of hypertension during pregnancy include methyldopa, hydralazine hydrochloride, or labetalol.

In certain embodiments, the methods provided herein can further include the step of administering an anti-hypertensive compound to the subject. Such administration may be by conventional means, e.g., administering an oral dosage form comprising an anti-hypertensive compound.

In certain embodiments, the methods provided herein can further include administering a growth factor or cytokine, such as, without limitation, a Vascular Endothelial Growth Factor Receptor (VEGFR) ligand, to the subject. In one embodiment, the growth factor is Vascular Endothelial Growth Factor (VEGF). In another embodiment, the growth factor is Placental Growth Factor (PlGF).

The methods disclosed herein may be practiced during pregnancy for the treatment or prevention of pre-eclampsia or eclampsia or after pregnancy to treat postpartum pre-eclampsia or eclampsia.

"Treating" refers to practicing the ex vivo methods disclosed herein for therapeutic purposes. To "treat" or to use for "therapy" refers to administering treatment to a subject already diagnosed as having or suffering from a pregnancy-related hypertensive disorder to improve the subject's condition. For example, the subject may be diagnosed as having or suffering from pre-eclampsia or eclampsia, based on identification of any of the characteristic symptoms described herein or based on measurement of the concentrations of sFlt-1 and sEng in the subject's blood, as described herein. The object of the treatment is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

"Prevent" refers to prophylactic treatment of a subject who is not yet ill, but who is susceptible to, or otherwise at risk for, developing a pregnancy-related hypertensive disorder, e.g., a subject who is determined to be at risk for developing pre-eclampsia or eclampsia.

"Pregnancy-related hypertensive disorder" refers to any condition or disease during pregnancy that is associated with or characterized by an increase in blood pressure. Included among these conditions and diseases are pre-eclampsia (including early-onset pre-eclampsia, late-onset pre-eclampsia, severe pre-eclampsia), eclampsia, gestational hypertension, HELLP syndrome, (hemolysis, elevated liver enzymes, low platelets), placental abruption, chronic hypertension during pregnancy, pregnancy with intra uterine growth restriction (IUGR), and pregnancy with a small for gestational age (SGA) fetus.

"Pre-eclampsia" refers to a multi-system disorder that is characterized by hypertension with proteinuria or edema, or both, glomerular dysfunction, brain edema, liver edema, or coagulation abnormalities due to pregnancy or the influence of a recent pregnancy. All forms of pre-eclampsia, such as early-onset, late-onset, mild, moderate, and severe pre-eclampsia are included in this definition. Pre-eclampsia generally occurs after the 20th week of gestation. Pre-eclampsia is generally defined as some combination of the following symptoms: (1) a systolic blood pressure (BP)>140 mm Hg and a diastolic BP>90 mm Hg after 20 weeks gestation (generally measured on two occasions, 4-168 hours apart), (2) new onset proteinuria (1+ by dipstick on urinalysis, >300 mg of protein in a 24-hour urine collection, or a single random urine sample having a protein/creatinine ratio>0.3), and (3) new-onset hypertension with new-onset of any of the following: thrombocytopenia, renal insufficiency, impaired liver function, pulmonary edema, cerebral/visual symptoms. Severe pre-eclampsia is generally defined as (1) a diastolic BP>110 mm Hg (generally measured on two occasions, 4-168 hours apart) or (2) proteinuria characterized by a measurement of 3.5 grams or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. HELLP syndrome is characterized by evidence of thrombocytopenia (<100,000 cells/μl), increased LDH (>600 IU/L) and increased AST (>70 IU/L). Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

"Subject" refers to a mammal, including, but not limited to, a human or non-human mammal such as a baboon, a monkey, a cow, a horse, a sheep, a pig, a goat, a dog, or a cat.

"At risk of developing" a pregnancy-related hypertensive disorder such as pre-eclampsia or eclampsia refers to a subject who does not currently have, but has a greater than average chance of developing, a pregnancy-related hypertensive disorder. Such at-risk subjects include pregnant women with an sFlt-1 blood concentration of greater than about 3 ng/ml, greater than about 4 ng/ml, greater than about 5 ng/ml, greater than about 6 ng/ml, greater than about 7 ng/ml, greater than about 8 ng/ml, greater than about 9 ng/ml, greater than about 10 ng/ml, greater than about 15 ng/ml, greater than about 20 ng/ml, greater than about 25 ng/ml, greater than about 30 ng/ml, greater than about 40 ng/ml, greater than about 45 ng/ml, greater than about 60 ng/ml, or greater than about 100 ng/ml, but who show no other signs of a pregnancy-related hypertensive disorder such as pre-eclampsia. At-risk subjects also include pregnant women with an sEng blood concentration of greater than about 3 ng/ml, greater than about 4 ng/ml, greater than about 5 ng/ml, greater than about 6 ng/ml, greater than about 7 ng/ml, greater than about 8 ng/ml, greater than about 9 ng/ml, greater than about 10 ng/ml, greater than about 15 ng/ml, greater than about 20 ng/ml, greater than about 25 ng/ml, greater than about 30 ng/ml, greater than about 40 ng/ml, greater than about 45 ng/ml, greater than about 60 ng/ml, or greater than about 100 ng/ml, but who show no other signs of a pregnancy-related hypertensive disorder such as pre-eclampsia.

The stage of pregnancy at which the methods described herein may be practiced depends on various clinical factors including the overall health of the subject and the severity of the symptoms of pre-eclampsia. In general, once pre-eclampsia or a predisposition to pre-eclampsia is detected, the methods may be employed. Treatment can be continued for a period of time ranging from 1 to 100 days, more preferably 1 to 60 days, 1 to 10 days, or 1 to 5 days, and most preferably 1 to 20 days.

In certain embodiments, the method is carried out on a subject on or after the 14th week of pregnancy, the 16th week of pregnancy, the 18th week of pregnancy, the 20th week of pregnancy, the 22nd week of pregnancy, the 24th week of pregnancy, the 26th week of pregnancy, the 28th week of pregnancy, the 30th week of pregnancy, the 32nd week of pregnancy, the 34th week of pregnancy, or the 36th week of pregnancy. In certain embodiments, the method is carried out on a subject between the 14th and 16th weeks of pregnancy, the 16th and 18th weeks of pregnancy, the 18th and 20th weeks of pregnancy, the 20th and 22nd weeks of pregnancy, the 22nd and 24th weeks of pregnancy, the 24th and 26th weeks of pregnancy, the 26th and 28th weeks of pregnancy, the 28th and 30th weeks of pregnancy, the 30th and 32nd weeks of pregnancy, the 32nd and 34th weeks of pregnancy, or the 34th and 36th weeks of pregnancy.

In certain embodiments, the subject's blood or plasma is contacted with the anti-sFlt-1 antibodies or sFlt-1-binding fragments thereof or sFlt-1 ligands and the anti-sEng antibodies or sEng-binding fragments thereof or sEng ligands only to the extent necessary to reduce sFlt-1 and sEng to desired levels. A desired level can be, for example, a level of sFlt-1 or sEng characteristic of a normal pregnancy. It has been observed that in normal pregnancy, the serum concentrations of sFlt-1 and sEng decrease from 8-12 weeks to 16-20 weeks, gradually increases at 26-30 weeks, rapidly elevates at 35-39 weeks, and returns to normal level after delivery. Accordingly, in one embodiment, the desired level is the normal level for the subject's stage of pregnancy. In another embodiment, the level is higher or lower that the normal level for the subject's stage of pregnancy. One of ordinary skill in the art would be able to determine a desired level, depending for example on the patient and the frequency with which the ex vivo procedure is to be performed.

The desired sFlt-1 and sEng levels can be achieved by controlling, for example, the length of time a subject is treated (i.e., the volume of blood or plasma treated for a particular flow rate), the flow rate over the immobilized antibody or ligand, and/or the binding capacity of the solid support bearing the antibody or ligand that binds to sFlt-1 or sEng. In one embodiment, a diagnostic is used to measure sFlt-1 and sEng levels at the time of treatment. In another embodiment, the diagnostic provides a real-time measure of sFlt-1 and sEng levels and treatment is stopped when the desired sFlt-1 and sEng levels are reached. In another embodiment, the time, flow rate, and/or capacity is predetermined based on the sFlt-1 and sEng levels diagnosed in the subject at the start of the procedure and the sFlt-1 and sEng levels desired to be reached.

In certain embodiments, the method decreases blood levels of sFlt-1 in the subject by 10%-90%, 20%-80%, or 30%-50%, as compared to the blood levels of sFlt-1 in the subject before the method is practiced on the subject. In certain embodiments, the method decreases blood levels of sFlt-1 in the subject by 10%-20%, 20%-30%, 30%-40%, 40%-50%, 50%-60%, 60%-70%, 70%-80%, 80%-90%, or 90%-100% as compared to the blood levels of sFlt-1 in the subject before the method is practiced on the subject. In certain embodiments, the method decreases blood levels of sEng in the subject by 10%-90%, 20%-80%, or 30%-50%, as compared to the blood levels of sEng in the subject before the method is practiced on the subject. In certain embodiments, the method decreases blood levels of sEng in the subject by 10%-20%, 20%-30%, 30%-40%, 40%-50%, 50%-60%, 60%-70%, 70%-80%, 80%-90%, or 90%-100% as compared to the blood levels of sEng in the subject before the method is practiced on the subject.

In one aspect, provided are systems for treating or preventing an sFlt-1- and sEng-related disease or disorder.

Provided herein is a system comprising anti-sFlt-1 antibodies or sFlt-1-binding fragments thereof and anti-sEng antibodies or sEng-binding fragments thereof bound to one or more solid supports, a first means for conveying blood from a subject to the anti-sFlt-1 antibodies or sFlt-1-binding fragments thereof and the anti-sEng antibodies or sEng-binding fragments thereof bound to the one or more solid supports so as to contact the blood with the anti-sFlt-1 antibodies or sFlt-1-binding fragments thereof and the anti-sEng antibodies or sEng-binding fragments thereof, and thereby remove sFlt-1 and sEng from the blood, and second means for conveying the blood to the subject following contact of the blood with the anti-sFlt-1 antibodies or sFlt-1-binding fragments thereof and the anti-sEng antibodies or sEng-binding fragments thereof.

In certain embodiments of the present invention, plasma, rather than blood, is contacted with anti-sFlt-1 antibodies or sFlt-1-binding fragments thereof and anti-sEng antibodies or sEng-binding fragments thereof bound to a solid support, in order to treat or prevent a pregnancy-related hypertensive disorder. Accordingly, in certain embodiments, the first means includes a device for separating the subject's blood into plasma and cellular components.

In certain embodiments, the first and/or second means may also comprise one or more sensors for determining the pressure and/or the flow rate of the blood in the conduit system.

In one aspect, provided is a system comprising:
- (a) anti-sFlt-1 antibodies or sFlt-1-binding fragments thereof and anti-sEng antibodies or sEng-binding fragments thereof;
  - wherein the anti-sFlt-1 antibodies or sFlt-1-binding fragments thereof and the anti-sEng antibodies or sEng-binding fragments thereof are bound to one or more solid supports;
  - wherein the anti-sFlt-1 antibodies or sFlt-1-binding fragments thereof deplete at least 70%, at least 80%, at least 90%, at least 95%, at least 96%, at least 97%, at least 98%, or at least 99% of sFlt-1 from human plasma in an in vitro analysis;
  - wherein the anti-sEng antibodies or sEng-binding fragments thereof deplete at least 70%, at least 80%, at least 90%, at least 95%, at least 96%, at least 97%, at least 98%, or at least 99% of sEng from human plasma in an in vitro analysis; and
  - wherein the sFlt-1 antibody or sFlt-1-binding fragment thereof to sFlt-1 molar ratio is 50 and/or wherein the sEng antibody or sEng-binding fragment thereof to sEng molar ratio is 50;
- (b) a first means for conveying blood or a component thereof from a subject to the anti-sFlt-1 antibodies or sFlt-1-binding fragments thereof and the anti-sEng antibodies or sEng-binding fragments thereof bound to the one or more solid supports so as to contact the blood or a component thereof with the anti-sFlt-1 antibodies or sFlt-1-binding fragments thereof and the anti-sEng antibodies or sEng-binding fragments thereof and thereby to remove sFlt-1 and sEng from the blood or a component thereof; and
- (c) a second means for conveying the blood or a component thereof to the subject following contact of the blood or a component thereof with the anti-sFlt-1 antibodies or sFlt-1-binding fragments thereof and the anti-sEng antibodies or sEng-binding fragments thereof.

In one embodiment, the first means comprises a device for separating the subject's blood into plasma and cellular components. In one embodiment, the device for separating the subject's blood into plasma and cellular components is a centrifuge or an apheresis device.

In one embodiment, the first means comprises
- a) an access device, inserted into a blood vessel of the subject, for accessing the subject's blood system; and
- b) a conduit system, which fluidly connects the access device to the anti-sFlt-1 antibodies or sFlt-1-binding fragments thereof and the anti-sEng antibodies or sEng-binding fragments thereof, bound to the one or more solid supports, thereby allowing the subject's blood or a component thereof to flow to and contact the anti-sFlt-1 antibodies or sFlt-1-binding fragments thereof and the anti-sEng antibodies or sEng-binding fragments thereof.

In certain embodiments, the first means comprises an access device, such as a catheter, needle, cannula, or the like, inserted into a blood vessel of the subject, for accessing the subject's blood system, a conduit system, such as tubing, piping, hollow fibers, or the like, which fluidly connects the access device to the anti-sFlt-1 antibodies or sFlt-1-binding fragments thereof and the anti-sEng antibodies or sEng-binding fragments thereof bound to the one or more solid supports, thereby allowing the subject's blood to flow to and contact the anti-sFlt-1 antibodies or sFlt-1-binding fragments thereof and the anti-sEng antibodies or sEng-binding fragments thereof and, optionally, a pump (e.g., a peristaltic pump) or the like, for moving blood from the subject through the access device and conduit system to the anti-sFlt-1 antibodies or sFlt-1-binding fragments thereof and the anti-sEng antibodies or sEng-binding fragments thereof.

In one embodiment, the second means comprises
- a) a conduit system; and
- b) a return device, where the return device is inserted into a blood vessel of the subject, and where the conduit system fluidly connects the blood or a component thereof in contact with the anti-sFlt-1 antibodies or sFlt-1-binding fragments thereof and the anti-sEng antibodies or sEng-binding fragments thereof, to the return device so as to allow for the return of the blood or a component thereof to the subject.

In certain embodiments, the second means comprises a conduit system, such as tubing, piping, hollow fibers, or the like, and a return device, such as a catheter, needle, cannula, or the like, where the return device is inserted into a blood vessel (e.g., a vein) of the subject, where the conduit system fluidly connects the blood or plasma in contact with the anti-sFlt-1 antibodies or sFlt-1-binding fragments thereof or sFlt-1 ligands and the anti-sEng antibodies or sEng-binding fragments thereof or sEng ligands, to the return device so as to allow for the return of the blood or plasma to the subject. Optionally, the second means also comprises a pump (e.g., a peristaltic pump) or the like, for moving the blood or plasma from the anti-sFlt-1 antibodies or sFlt-1-binding fragments thereof or sFlt-1 ligands and the anti-sEng antibodies or sEng-binding fragments thereof or sEng ligands, through the conduit system to the return device. This pump or the like may be the same pump or the like that is part of the first means or, alternatively, the motive force for the second means for conveying the blood or plasma to the subject may be a separate pump or the like, specific to the second means.

In one embodiment, the system comprises
- (i) an anti-sFlt-1 antibody or sFlt-1-binding fragment thereof disclosed herein and/or an anti-sFlt-1 antibody that competes for binding to sFlt-1 with an anti-sFlt-1 antibody or sFlt-1-binding fragment thereof disclosed herein; and
- (ii) an anti-sEng antibody or sEng-binding fragment thereof disclosed herein and/or an anti-sEng antibody that competes for binding to sEng with an anti-sEng antibody or sEng-binding fragment thereof disclosed herein.

The anti-sFlt-1 antibodies or sFlt-1-binding fragments thereof and the anti-sEng antibodies or sEng-binding fragments thereof, bound to a solid support, can be used to remove sFlt-1 and sEng from the body fluids of subjects suffering from, or at risk of developing, pre-eclampsia or eclampsia. In certain embodiments, the anti-sFlt-1 antibodies or sFlt-1-binding fragments thereof and the anti-sEng antibodies or sEng-binding fragments thereof, bound to a solid support, are used to remove sFlt-1 and sEng from blood or blood plasma. In certain embodiments, the anti-sFlt-1 antibodies or sFlt-1-binding fragments thereof and the anti-sEng antibodies or sEng-binding fragments thereof, bound to a solid support are used in extracorporeal immunoabsorbent devices, which are known in the art. Blood or plasma is exposed to the bound support-bound anti-sFlt-1 antibodies or sFlt-1-binding fragments thereof and anti-sEng antibodies or sEng-binding fragments thereof, resulting in partial or complete removal of circulating sFlt-1 and sEng (free or in complexes with other blood proteins), following which the blood or plasma is returned to the subject's body. The methods disclosed herein may be implemented in a continuous flow arrangement, with or without interposing a cell removal step, e.g., a centrifugation step, prior to contact of the blood or plasma with the anti-sFlt-1 antibodies or sFlt-1-binding fragments thereof and the anti-sEng antibodies or sEng-binding fragments thereof.

Solid supports for use in the methods described herein preferably should be non-toxic and stable when exposed to blood or blood components. The solid supports may be chosen from among those well known in the art. For example, any suitable porous material may be used as the solid support. Examples of suitable solid supports include, e.g., carbohydrate-based materials such as the various types of SEPHAROSE® (a crosslinked, beaded-form of agarose), e.g., SEPHAROSE 4B®, 4FF®, CL-4B® and CL-6B.

The solid support may be comprised of organic or inorganic molecules, or a combination of organic and inorganic molecules, and may be comprised of one or more functional groups, e.g., hydroxyl groups, suitable for forming covalent bonds with activating agents. The solid support may be comprised of a hydrophilic compound, a hydrophobic compound, or any combination thereof. The solid support may be comprised of a polymer or a copolymer.

Examples of suitable materials for use in solid supports include, but are not limited to, agarose, cellulose, polyether sulfones, polyamides, polysaccharides, polytetrafluoroethylene, polyesters, polyurethanes, polyvinylidene fluoride, polypropylene, fluorocarbons, e.g., poly(tetrafluoroethylene-co-perfluoro(alkyl vinyl ether)), polyethylene, glass, polycarbonates, polyacrylate, polyacrylamide, poly(azolactone), polystyrene, ceramics, and nylon.

The solid support need not be in any particular shape. For example, the solid support may be in the form of beads, membranes, gels, columns, chips, plates, tubes, sheets, fibers, or hollow fibers. The solid support can also be in the form of a coating on the interior of one or more lengths of tubing, piping, or hollow fibers through which blood or plasma flows. In such embodiments, the tubing, piping, or hollow fibers are preferably coiled or otherwise convoluted or bent, in order to maximize the amount of solid support contacted by the blood or plasma flowing through the tubing, piping, or hollow fibers.

Methods of attaching or binding antibodies and ligands to a solid support are well known in the art and may be used to attach or bind the anti-sFlt-1 antibodies or sFlt-1-binding fragments thereof and the anti-sEng antibodies or sEng-binding fragments thereof, used in the methods described herein to a solid support. Such methods include, without limitation, the use of cyanogen bromide, 1,1'-carbonyldiimidazole (CDI), or triethylamine.

In general, solid supports may be activated for the attachment or binding of anti-sFlt-1 antibodies or sFlt-1-binding fragments thereof and anti-sEng antibodies or sEng-binding fragments thereof, by contacting the solid supports with an activating agent such as an aldehyde, an epoxide, a cyanogen, or an activated carboxylic acid.

Methods of attaching or binding antibodies to solid supports are well known in the art. See, e.g., Hermanson et al. 1992, Immobilized Affinity Ligand Techniques, Academic Press; U.S. Pat. Nos. 5,874,165; 3,932,557; 4,772,635; 4,210,723; 5,250,6123; European Patent Application EP 1 352 957 A1, and International Patent Publication WO 2004/074471. Typically, the solid support is activated with a reactive functional group such as an epoxide (e.g., by the use of epichlorohydrin), cyanogens (e.g., cyanogen bromide (CNBr)), N,N-disuccinimidylcarbonate (DSC), aldehydes, or an activated carboxylic acid (e.g., N-hydroxysuccinimide (NHS) esters, or carbonyldiimidazole (CDI) activated esters). Activated groups may be attached directly to the solid support, as is generally the case for CNBr, or the activated groups may be part of a linker or spacer molecule, which is typically a linear chain of carbon, optionally substituted with oxygen and/or nitrogen atoms. A typical example of such a linker is the ten membered chain of carbon and oxygen found in the linker butanediol digycidyl ether (a common epoxide coupling agent). The activated solid support is then contacted with the antibody under coupling conditions.

Other linkers may include a branched, unbranched, or cyclic carbon chain comprising from 1 to 30 carbon atoms. In certain embodiments, the linker may be comprised of more than 30 carbon atoms. The linker may comprise at least one hetero-atom such as nitrogen, oxygen, or sulfur.

The commercial product AFFI-GEL 15® (BioRad, Hercules, Calif.) may be used for linker-assisted coupling. AFFI-GEL 15® is an agarose support derivatized with an NHS activated carboxylic acid as part of a linker arm containing a positively charged secondary amine. Another charged linker is disclosed in U.S. Pat. No. 5,260,373. A shorter linker arm comprised of arginine may be used to facilitate coupling to an agarose support. The arginine linker is activated with NHS and carries a positive charge.

Anti-sFlt-1 antibodies, sFlt-1-binding fragments thereof, and sFlt-1 specific polypeptides and ligands can be covalently or non-covalently coupled to a solid support in a manner that provides more uniform orientation and efficient sFlt-1-binding. Likewise, anti-sEng antibodies, sEng-binding fragments thereof, and sEng specific polypeptides and ligands can be covalently or non-covalently coupled to a solid support in a manner that provides more uniform orientation and efficient sEng-binding. Most methods involve modifying a protein with a unique chemical group at a predefined position, and reacting that group with a complementary group on the solid support. In another embodiment, anti-sFlt-1 antibodies, sFlt-1-binding fragments thereof, sFlt-1 ligands, anti-sEng antibodies, sEng-binding fragments thereof, or sEng ligands are produced with N- or C-terminal linkers capable of being coupled to a solid support. In certain embodiments, polypeptides and ligands are synthesized directly on a solid support.

In one aspect, provided is a housing or chamber such as a column containing anti-sFlt-1 antibodies or sFlt-1-binding fragments thereof and anti-sEng antibodies or sEng-binding fragments thereof bound to a solid support, where the housing or chamber is suitable for use in treating or preventing a pregnancy-related hypertensive disorder such as eclampsia or pre-eclampsia.

In certain embodiments, the housing or chamber is a column. "Column" refers to a container, chamber, or housing, generally cylindrical in shape, containing a solid support to which anti-sFlt-1 antibodies or sFlt-1-binding fragments thereof or sFlt-1 ligands and anti-sEng antibodies or sEng-binding fragments thereof or sEng ligands can be or have been bound.

In certain embodiments, the column contains a volume of about 0.1 to 5 ml, about 5 ml to 2000 ml, about 10 ml to about 1000 ml, about 50 ml to about 500 ml, or about 200 ml to about 400 ml of anti-sFlt-1 antibodies or sFlt-1-binding fragments and anti-sEng antibodies or sEng-binding fragments thereof, bound to a solid support. In certain embodiments, the column contains a volume of about 0.1 to 5 ml, about 5 ml, about 10 ml, about 25 ml, about 50 ml, about 100 ml, about 200 ml, about 300 ml, about 500 ml, about 750 ml, about 1000 ml, about 1500 ml, or about 2000 ml of anti-sFlt-1 antibodies or sFlt-1-binding fragments and anti-sEng antibodies or sEng-binding fragments thereof, bound to a solid support. In certain embodiments, the column contains one or more anti-coagulant substances, e.g., heparin. In certain embodiments, the interior of the column has been treated in a manner intended to reduce the amount of bacteria, *mycoplasma* and/or viruses in the interior of the column. In embodiments, the interior of the column is sterile.

In certain embodiments, the column contains sufficient anti-sFlt-1 antibodies or sFlt-1-binding fragments thereof, bound to a solid support, to remove at least 10 µg, at least 25 µg, at least 50 µg, at least 75 µg, at least 100 µg, at least 150 µg, at least 200 µg, at least 300 µg, at least 400 µg, at least 500 µg, at least 600 µg, at least 700 µg, at least 800 µg, at least 900 µg, at least 1000 µg, at least 1500 µg, or at least 2000 µg of sFlt-1 from human blood or plasma. In certain embodiments, the column contains sufficient anti-sFlt-1 antibodies or sFlt-1-binding fragments thereof, bound to a solid support, to remove at least 10 µg to 2000 µg, at least 20 µg to 1000 µg, at least 50 µg to 500 µg, or at least 100 µg to 200 µg of sFlt-1 from human blood or plasma. In certain embodiments, the column contains sufficient anti-sEng antibodies or sEng-binding fragments thereof, bound to a solid support, to remove at least 10 µg, at least 25 µg, at least 50 µg, at least 75 µg, at least 100 µg, at least 150 µg, at least 200 µg, at least 300 µg, at least 400 µg, at least 500 µg, at least 600 µg, at least 700 µg, at least 800 µg, at least 900 µg, at least 1000 µg, at least 1500 µg, or at least 2000 µg of sEng from human blood or plasma. In certain embodiments, the column contains sufficient anti-sEng antibodies or sEng-binding fragments thereof, bound to a solid support, to remove at least 10 µg to 2000 µg, at least 20 µg to 1000 µg, at least 50 µg to 500 µg, or at least 100 µg to 200 µg of sEng from human blood or plasma.

In one aspect, provided are methods of making a device for treating or preventing a pregnancy-related hypertensive disorder such as eclampsia or pre-eclampsia comprising:

(a) binding anti-sFlt-1 antibodies or sFlt-1-binding fragments thereof to a solid support to produce anti-sFlt-1 antibodies or sFlt-1-binding fragments thereof bound to a solid support, and binding anti-sEng antibodies or sEng-binding fragments thereof to a solid support to produce anti-sEng antibodies or sEng-binding fragments thereof bound to a solid support, (b) introducing the anti-sFlt-1 antibodies or sFlt-1-binding fragments thereof and the anti-sEng antibodies or sEng-binding fragments thereof bound to the solid support into a housing or chamber such as a column to produce a housing or chamber containing the anti-sFlt-1 antibodies or sFlt-1-binding fragments thereof and the anti-sEng antibodies or sEng-binding fragments thereof, bound to the solid support, (c) fluidly connecting the housing or chamber containing the anti-sFlt-1 antibodies or sFlt-1-binding fragments thereof and the anti-sEng antibodies or sEng-binding fragments thereof, bound to the solid support, to a means for conveying blood or plasma from a subject to the anti-sFlt-1 antibodies or sFlt-1-binding fragments thereof and the anti-sEng antibodies or sEng-binding fragments thereof, bound to the solid support, (d) fluidly connecting the housing or chamber containing the anti-sFlt-1 antibodies or sFlt-1-binding fragments thereof and the anti-sEng antibodies or sEng-binding fragments thereof, bound to the solid support, to a means for conveying the blood or plasma from the anti-sFlt-1 antibodies or sFlt-1-binding fragments thereof and the anti-sEng antibodies or sEng-binding fragments thereof, bound to the solid support, to the subject, where the means are connected to the housing or chamber so as to allow for contact of the blood or plasma from the subject with the anti-sFlt-1 antibodies or sFlt-1-binding fragments thereof and the anti-sEng antibodies or sEng-binding fragments thereof, bound to the solid support, and thereby remove sFlt-1 and sEng from the blood or plasma.

In one aspect, provided are methods of making a device for treating or preventing a pregnancy-related hypertensive disorder such as eclampsia or pre-eclampsia comprising modifying a dialysis or apheresis device or system so as to provide the dialysis or apheresis device or system with a housing or chamber such as a column containing anti-sFlt-1 antibodies or sFlt-1-binding fragments thereof and anti-sEng antibodies or sEng-binding fragments thereof, bound to a solid support, so as to allow the dialysis or apheresis device or system to provide for the contact of blood or plasma from a subject with the anti-sFlt-1 antibodies or sFlt-1-binding fragments thereof and the anti-sEng antibodies or sEng-binding fragments thereof, bound to the solid support, and thereby remove sFlt-1 and sEng from the blood or plasma to produce sFlt-1- and sEng-depleted blood or plasma.

In certain embodiments, provided are methods of identifying an anti-sFlt-1 antibody or sFlt-1-binding fragment thereof and an anti-sEng antibody or sEng-binding fragment thereof suitable for use in ex vivo methods of treating or preventing a pregnancy-related hypertensive disorder such as eclampsia or pre-eclampsia comprising:

(a) obtaining an antibody or antigen-binding fragment thereof that binds to sFlt-1 and obtaining an antibody or antigen-binding fragment thereof that binds to sEng;

(b) binding the antibody or antigen-binding fragment thereof that binds to sFlt-1 to a solid support to produce a solid support comprising bound anti-sFlt-1 antibody or sFlt binding fragment thereof and binding the antibody or antigen-binding fragment thereof that binds to sEng to a solid support to produce a solid support comprising bound anti-sEng antibody or sEng-binding fragment thereof;

(c) determining if the solid support comprising bound anti-sFlt-1 antibody or sFlt-1-binding fragment thereof and bound anti-sEng antibody or sEng-binding fragment thereof a can bind sFlt-1 and sEng in a fluid sample from a subject and thereby remove sFlt-1 and sEng from the fluid sample;

where if the solid support comprising bound anti-sFlt-1 antibody or sFlt-1-binding fragment thereof and anti-sEng antibody or sEng-binding fragment thereof can bind sFlt-1 and sEng in a fluid sample from a subject and thereby remove sFlt-1 and sEng from the fluid sample, the antibodies of step (a) are identified as an anti-sFlt-1 antibody or sFlt-1-binding fragment thereof and as an anti-sEng antibody or sEng-binding fragment thereof suitable for use in ex vivo methods of treating or preventing a pregnancy-related hypertensive disorder such as eclampsia or pre-eclampsia.

In certain embodiments, the subject is a mammal. In certain embodiments, the subject is a human.

In certain embodiments, the fluid sample is blood, plasma, amniotic fluid, or urine.

A modified dialysis or apheresis system can be used to practice the methods disclosed herein, wherein the modified dialysis or apheresis system provides the means by which blood is removed, passed over a solid support containing bound anti-sFlt-1 antibodies or sFlt-1-binding fragments thereof and anti-sEng antibodies or sEng-binding fragments thereof and returned to the subject's body following removal of sFlt-1 and sEng from the blood by the anti-sFlt-1 antibodies or sFlt-1-binding fragments thereof and the anti-sEng antibodies or sEng-binding fragments thereof. In some embodiments, the apheresis system is a plasmapheresis system and plasma rather than blood is passed over a solid support containing bound anti-sFlt-1 antibodies or sFlt-1-binding fragments thereof and anti-sEng antibodies or sEng-binding fragments thereof, and returned to the subject's body following removal of sFlt-1 and sEng from the plasma by the anti-sFlt-1 antibodies or sFlt-1-binding fragments thereof and anti-sEng antibodies or sEng-binding fragments thereof.

In certain embodiments, the methods disclosed herein may be carried out using a modified version of a device known in the art that enables removal and extracorporeal treatment of a body fluid such as whole blood or plasma. One such device is a dialysis machine. Dialysis machines are in routine use and methods to control blood flow, remove air bubbles, and maintain proper electrolyte balance, blood sugar, oxygenation, temperature, sterility, and other vital factors during dialysis, are well known and established in the art. In certain embodiments, the methods disclosed herein may be carried out using existing dialysis systems where the dialyzer is replaced by a housing or chamber, such as a column, containing a solid support to which anti-sFlt-1 antibodies or sFlt-1-binding fragments thereof and anti-sEng antibodies or sEng-binding fragments thereof, are bound. When blood flows through the housing or chamber, the anti-sFlt-1 antibodies or sFlt-1-binding fragments thereof and anti-sEng antibodies or sEng-binding fragments thereof, remove sFlt-1 and sEng from the blood, thereby lowering the concentrations of sFlt-1 and sEng in the blood and treating or preventing a pregnancy-related hypertensive disorder such as pre-eclampsia or eclampsia.

Another well-known device that can be used to practice the methods described herein is an apheresis system, e.g., a plasmapheresis system. Plasmapheresis involves the extracorporeal manipulation and removal of certain cellular components of the blood, after which the blood is re-infused into the subject to induce a desired clinical effect. During plasmapheresis, blood is initially taken out of the body through an access device such as a needle or catheter. Plasma is then removed from the blood by a cell separator. Three procedures are commonly used to separate the plasma from blood cells: (1) Discontinuous flow centrifugation, where, typically, a 300 ml volume of blood is removed at a time and centrifuged to separate plasma from blood cells. (2) Continuous flow centrifugation, where centrifugation is used to continuously spin out plasma. (3) Plasma filtration, where the plasma is filtered using standard hemodialysis equipment.

Apheresis devices suitable for modification for use in the methods disclosed herein are described, e.g., in U.S. Pat. Nos. 5,098,372; 5,112,298; and 6,319,471. Other suitable devices include the LIFE-18® plasma therapy device from PlasmaSelect (Munich, Germany), the Diapact® CRRT from B. Braun (Melsungen, Germany), the COBE SPECTRA®, a product of Cobe BCT, Incorporated, 1201 Oak Street, Lakewood, Co. 80215, and the ELUTRA® Cell Separation System of Gambro BCT, Inc.

In certain embodiments of the systems disclosed herein, the access device for accessing a subject's blood system and/or the return device for returning blood, plasma, or cellular components of blood to a subject is a single lumen catheter or a double lumen catheter such as, e.g., the single lumen or double lumen catheters sold by Fresenius Medical Care (Bad Homburg, Germany). Such catheters may be made of thermos-sensitive polyurethane that adapts to the contour of a blood vessel as the polyurethane heats to body temperature.

In certain embodiments of the methods disclosed herein, removing blood from the subject includes removing an amount of blood from the subject sufficient to derive at least about 300 milliliters of plasma from the blood. In certain embodiments, removing the blood from the subject includes removing at least 650 milliliters of blood from the subject. In certain embodiments, removing the blood from the subject includes removing at least two liters of blood from the subject. In certain embodiments, removing the blood from the subject includes continuously removing blood from the subject until substantially the entire blood volume of the subject is contacted with anti-sFlt-1 antibodies or sFlt-1-binding fragments thereof and anti-sEng antibodies or sEng-binding fragments thereof, at least once, at least twice, or at least three times. In certain embodiments, removing the blood from the subject includes continuously removing blood from the subject until about two-thirds, about half, about one-fourth, about one-fifth, or about one-tenth of the entire blood volume of the subject is contacted with anti-sFlt-1 antibodies or sFlt-1-binding fragments thereof and anti-sEng antibodies or sEng-binding fragments thereof. In certain embodiments, removing the blood from the subject includes continuously removing blood from the subject until the concentrations of sFlt-1 and sEng in the subject's blood reach a preselected concentration. In certain embodiments, the preselected concentration is less than about 50 ng/ml, less than about 40 ng/ml, less than about 25 ng/ml, less than about 10 ng/ml, less than about 5 ng/ml, less than about 4 ng/ml, less than about 3 ng/ml, less than about 2 ng/ml, less than about 1 ng/ml, less than about 0.75 ng/ml, or less than about 0.5 ng/ml. In certain embodiments, the preselected concentration is about 40-50 ng/ml, about 30-40 ng/ml, about 20-30 ng/ml, about 10-20 ng/ml, about 5-10 ng/ml, about 5-8 ng/ml, about 3-7 ng/ml, about 1-5 ng/ml, about 1-3 ng/ml, about 0.75-2 ng/ml, or about 0.5-1 ng/ml.

The concentrations of sFlt-1 and sEng concentration can be measured automatically in blood or plasma, either continuously, or at preset intervals. For example, plasma samples from the subject can be reacted with a labeled reagent that binds to sFlt-1 or particles containing sFlt-1 and the amount of sFlt-1 measured. Alternatively, a sensor with a linked reagent that specifically binds to sFlt-1 (including particles containing sFlt-1) can be used to continuously detect the amount of bound sFlt-1. Likewise, plasma samples from the subject can be reacted with a labeled reagent that binds to sEng or particles containing sEng and the amount of sEng measured. Alternatively, a sensor with a linked reagent that specifically binds to sEng (including particles containing sEng) can be used to continuously detect the amount of bound sEng. The blood filtration procedure is terminated when the concentrations of sFlt-1 and/or sEng detected in a subject's blood or plasma drop below a predetermined value.

Diagnostic methods known in the art can be used to monitor a subject's pre-eclampsia or eclampsia during therapy to determine the effectiveness of therapy according to the methods disclosed herein. Suitable diagnostic methods are disclosed in, e.g., U.S. Pat. Nos. 7,335,362; 7,435,419; and 7,407,659.

In certain embodiments, diagnostic methods are employed that determine and/or monitor the concentration of sFlt-1 and/or sEng in a subject's blood in order to identify subjects suitable for treatment or prevention using the methods disclosed herein. In certain embodiments, diagnostic methods are employed to identify subjects at risk of developing a pregnancy-related hypertensive disorder such as pre-eclampsia or eclampsia where the subjects are pregnant women with sFlt-1 and sEng blood concentrations of greater than about 5 ng/ml, greater than about 6 ng/ml, greater than about 7 ng/ml, greater than about 8 ng/ml, greater than about 9 ng/ml, greater than about 10 ng/ml, greater than about 15 ng/ml, greater than about 20 ng/ml, greater than about 25 ng/ml, greater than about 30 ng/ml, greater than about 40 ng/ml, or greater than about 45 ng/ml, greater than about 60 ng/ml, or greater than about 100 ng/ml, but who show no other signs of a pregnancy-related hypertensive disorder such as pre-eclampsia.

Accordingly, provided is a method of identifying a subject having, or at risk of developing, a pregnancy-related hypertensive disorder and then practicing the ex vivo methods disclosed herein on the subject so identified, thereby treating or preventing the pregnancy-related hypertensive disorder. In certain embodiments, a pregnant human is identified as a subject suitable for treatment or prevention by the methods disclosed herein if the concentrations of sFlt-1 and sEng in the subject's blood during the second trimester of pregnancy is determined to be above about 3.5 ng/ml, above about 4 ng/ml, above about 5 ng/ml, above about 7.5 ng/ml, above about 10 ng/ml, above about 20 ng/ml, above about 30 ng/ml, above about 40 ng/ml, or above about 50 ng/ml.

In certain embodiments where the subject's blood levels of sFlt-1 and sEng are determined and/or monitored, the methods described herein may be employed until the concentrations of sFlt-1 and/or sEng in the subject's blood are less than about 50 ng/ml, less than about 45 ng/ml, less than about 40 ng/ml, less than about 35 ng/ml, less than about 30 ng/ml, less than about 25 ng/ml, less than about 20 ng/ml, less than about 15 ng/ml, less than about 10 ng/ml, less than about 7.5 ng/ml, less than about 5 ng/ml, less than about 4 ng/ml, less than about 3 ng/ml, less than about 2 ng/ml, less than about 1.5 ng/ml, or less than about 1 ng/ml.

In certain embodiments, the methods disclosed herein may be employed until an improvement is detected in the symptoms of a pregnancy-related hypertensive disorder. In certain embodiments, the pregnancy-related hypertensive disorder is pre-eclampsia and the improvement is a decrease in blood pressure to a value of less than 140 mmHg (systolic) and/or less than 90 mmHg (diastolic).

It is to be understood that this invention is not limited to the particular molecules, compositions, methodologies, or protocols described, as these may vary. Any methods and materials similar or equivalent to those described herein can be used in the practice or testing of embodiments of the present invention. It is further to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes those possibilities).

All other referenced publications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

To facilitate a better understanding of the present invention, the following examples of specific embodiments are given. The following examples should not be read to limit or define the entire scope of the invention.

EXAMPLES

Example 1: Examples of Anti-sFlt-1 Antibodies Anti-sEng Antibodies

Antibodies AG10B and cENG10

The generation of anti-sFlt-1 antibody AG10B was previously described in U.S. Pat. No. 9,592,331, which is incorporated by reference in its entirety herein. Briefly, from a screen of mouse antibodies against the human sFlt-1 protein, antibody R543 was chosen as the lead antibody based on its high affinity to sFlt-1 and effective depletion of recombinant sFlt-1 spiked into plasma or endogenous sFlt-1 from pre-eclampsia serum. The variable regions $V_H$ and $V_L$ of R543 were cloned and their gene sequences were fused in frame with the sequences encoding the human IgG1 constant regions containing an N298Q mutation to produce the chimeric AG10B construct.

The generation of the anti-sEng antibody is described in commonly assigned, U.S. Application Provisional No. 62/947,759, filed Dec. 13, 2020, which is incorporated by reference herein in its entirety. Briefly, from a screen of mouse antibodies against human sEng protein, antibody MAb 210 was chosen as the lead antibody based on its high affinity to its target protein sEng and effective depletion of recombinant sEng spiked in plasma or endogenous sEng from pre-eclampsia serum. The variable regions $V_H$ and $V_L$ of MAb210 were cloned and their gene sequences were fused in frame with the sequences encoding the human IgG1 constant regions containing an N300Q mutation that minimizes FcR engagement for enhanced safety to produce the chimeric cENG10 antibody construct. Table 1 provides a summary of the CDR sequences for anti-sFlt-1 antibody AG10B and anti-sEng antibody cENG10. Table 2 provides a summary of the heavy and light chain sequences for AG10B and cENG10.

TABLE 1

CDR sequences for anti-sFlt-1 antibody
AG10B and anti-sEng antibody cENG10

| CDR | Amino Acid Sequence | SEQ ID NO: | Antibody |
|---|---|---|---|
| CDR1H | GYTFTDYVIS | 1 | AG10B |
| CDR2H | WIGEIYPGSGSIYYNEKFKG | 2 | AG10B |
| CDR3H | GHYYGYFDY | 3 | AG10B |
| CDR1L | KASQDVTITVAWY | 4 | AG10B |
| CDR2L | LLIYSASYRYT | 5 | AG10B |
| CDR3L | QQHYTTPWT | 6 | AG10B |
| CDR1H | GYTITEHTLH | 7 | cENG10 |
| CDR2H | GINFDNGGTTYRQKFKD | 8 | cENG10 |
| CDR3H | RAYYYGSAFDY | 9 | cENG10 |
| CDR1L | RASSSVNYVY | 10 | cENG10 |
| CDR2L | YTSNLAP | 11 | cENG10 |
| CDR3L | QQFISFPYT | 12 | cENG10 |

TABLE 2

Summary of relevant sequences for anti-sFlt-1
antibody AG10B and anti-sEng antibody cENG10

| SEQ ID NO: | Sequence | Type of Sequence | Antibody |
|---|---|---|---|
| 13 | Variable domain of heavy chain | Nucleotide | AG10B |
| 14 | Variable domain of heavy chain | Amino acid | AG10B |
| 15 | Variable domain of light chain | Nucleotide | AG10B |
| 16 | Variable domain of light chain | Amino acid | AG10B |
| 17 | Heavy chain | Nucleotide | AG10B |
| 18 | Heavy chain | Amino acid | AG10B |
| 19 | Light chain | Nucleotide | AG10B |
| 20 | Light chain | Amino acid | AG10B |
| 21 | Variable domain of heavy chain | Nucleotide | cENG10 |
| 22 | Variable domain of heavy chain | Amino acid | cENG10 |
| 23 | Variable domain of light chain | Nucleotide | cENG10 |
| 24 | Variable domain of light chain | Amino acid | cENG10 |
| 25 | Heavy chain | Nucleotide | cENG10 |
| 26 | Heavy chain | Amino acid | cENG10 |
| 27 | Light chain | Nucleotide | cENG10 |
| 28 | Light chain | Amino acid | cENG10 |

Nucleotide sequence of chimeric anti-sFlt-1 antibody AG10B variable domain of heavy chain ($V_H$) (without leader sequence)—SEQ ID NO:13.

```
CAGGTTCAGC TGCAGCAGTC TGGACCTGAG CTGGTGAAGC

CTGGGGCTTC AGTGAAGATG TCCTGCAAGG CTTCTGGATA

CACATTCACT GACTATGTTA TAAGTTGGGT GAAACAGAGA

ACTGGACAGG GCCTTGAGTG GATTGGAGAG ATTTATCCTG

GAAGTGGTAG TATTTACTAC AATGAGAAGT TCAAGGGCAA

GGCCACACTG ACTGCAGACA CATCCTCCAA CACAGCCTAC
```

```
ATGCAGCTCA GCAGCCTGAC ATTTGAGGAC TCTGCGGTCA

TTTTCTGTGC AAGAGGGCAT TATTACGGTT ACTTTGACTA

CTGGGGCCAA GGCACCACTC TCACAGTCTC CTCA
```

Amino acid sequence of chimeric anti-sFlt-1 antibody AG10B variable domain of heavy chain ($V_H$) (without leader sequence)—SEQ ID NO:14. CDRs are indicated in bold.

```
QVQLQQSGPE LVKPGASVKM SCKASGYTFT DYVISWVKQR

TGQGLEWIGE IYPGSGSIYY NEKFKGKATL TADTSSNTAY

MQLSSLTFED SAVIECARGH YYGYFDYWGQ GTTLTVSS
```

Nucleotide sequence of chimeric anti-sFlt-1 antibody AG10B variable domain of light chain ($V_L$) (without leader sequence)—SEQ ID NO:15.

```
GACATTGTGA TGACCCAGTC TCACAAATTC ATGTCCACAT

CAGTAGGAGA CAGGGTCAGC ATCACCTGCA AGGCCAGTCA

GGATGTGACT ATTACTGTAG CCTGGTATCA ACAGAAACCA

GGACAATCTC CTAAACTTCT GATTTACTCG GCATCCTACC

GGTACACTGG AGTCCCTGAT CGCTTCACTG GCAGTGGATC

TGGGACGGAT TTCACTTTCA CCATCAGCAG TGTGCAGGCT

GAAGACCTGG CAGTTTATTA CTGTCAGCAA CATTATACTA

CTCCGTGGAC GTTCGGTGGA GGCACCAAGC TGGAAATCAA

A
```

Amino acid sequence of chimeric anti-sFlt-1 antibody AG10B variable domain of light chain ($V_L$) (without leader sequence)—SEQ ID NO:16. CDRs are indicated in bold.

```
DIVMTQSHKE MSTSVGDRVS ITCKASQDVT ITVAWYQQKP

GQSPKLLIYS ASYRYTGVPD RFTGSGSGTD FTFTISSVQA

EDLAVYYCQQ HYTTPWTFGG GTKLEIK
```

Nucleotide sequence of chimeric anti-sEng antibody cENG10 variable domain of heavy chain ($V_H$) (without leader sequence)—SEQ ID NO:21.

```
GAGGTCCAGC TGGAACAGTC TGGACCTGAA GTGGTGAAGC

CTGGGACTTC AGTGAAGATA TCCTGCAAGA CTTCTGGATA

CACAATCACT GAACACACCT TGCACTGGAT AAAGCAGAAC

CAGGGAAAGA GCCTTGAGTG GATTGGTGGT ATTAATTTTG

ACAATGGTGG TACTACCTAC AGGCAGAAAT TCAAGGACAA

GGCCACATTG ACTGTGGACA AGTCCTCCAG CACAGCCTTC

ATGGAGCTCC GCAGCCTGAC TTCTGATGAT TCTGCAGTCT

ATTTCTGCGC AAGAAGGGGC TATTACTACG GTAGTGCCTT

TGACTACTGG GGCCAAGGCA CCACTCTCAC AGTCTCCTCA
```

Amino acid sequence of chimeric anti-sEng antibody cENG10 variable domain of heavy chain (V$_H$) (without leader sequence)—SEQ ID NO:22. CDRs are indicated in bold.

```
EVQLEQSGPE VVKPGTSVKI SCKTSGYTIT EHTLHWIKQN

QGKSLEWIGG INFDNGGTTY RQKFKDKATL TVDKSSSTAF

MELRSLTSDD SAVYFCARRA YYYGSAFDYW GQGTTLTVSS
```

Nucleotide sequence of chimeric anti-sEng antibody cENG10 variable domain of light chain (V$_L$) (without leader sequence)—SEQ ID NO:23.

```
GAAAATGTGC TCACCCAGTC TCCAGCAATC ATGTCTGCAT

CTCTAGGGGA GAAGGTCACC ATGACCTGCA GGGCCAGCTC

AAGTGTGAAT TACGTGTACT GGTACCAGCA GAAGTCAGAT

GCCTCCCCCA AACTATGGAT TTATTACACT TCCAACCTGG

CTCCTGGAGT CCCAGCTCGC TTCAGTGGCA GTGGGTCTGG
```

```
GAACTCTTAT TCTCTCACAA TCAGCAGCAT GGAGGGTGAA

GATGCTGCCA CTTATTACTG CCAGCAGTTT ATTAGTTTCC

CATACACGTT CGGAGGGGGG ACCAAGCTGG AAATAAAA
```

Amino acid sequence of chimeric anti-sEng antibody cENG10 variable domain of light chain (V$_L$) (without leader sequence)—SEQ ID NO:24. CDRs are indicated in bold.

```
ENVLTQSPAI MSASLGEKVT MTCRASSSVN YVYWYQQKSD

ASPKLWIYYT SNLAPGVPAR FSGSGSGNSY SLTISSMEGE

DAATYYCQQF ISFPYTFGGG TKLEIK
```

Nucleotide sequence of chimeric anti-sFlt-1 antibody AGB10 heavy chain—SEQ ID NO:17. The leader sequence encoding the secretion signal peptide (19 amino acid residues, nucleotides 1-57) is underlined. The sequence encoding the variable chain (V$_H$) is indicated in bold (nucleotides 58-411). The human IgG C$_H$1-C$_H$3 portion of the heavy chain spans nucleotides 412-1398. The codon encoding the N298Q mutation is underlined, bold, and cursive.

```
ATGATGTCCT TTGTCTCTCT GCTCCTGGTA GGCATCCTAT TCCATGCCAC

CCAGGCCCAG GTTCAGCTGC AGCAGTCTGG ACCTGAGCTG GTGAAGCCTG 100

GGGCTTCAGT GAAGATGTCC TGCAAGGCTT CTGGATACAC ATTCACTGAC

TATGTTATAA GTTGGGTGAA ACAGAGAACT GGACAGGGCC TTGAGTGGAT 200

TGGAGAGATT TATCCTGGAA GTGGTAGTAT TTACTACAAT GAGAAGTTCA

AGGGCAAGGC CACACTGACT GCAGACACAT CCTCCAACAC AGCCTACATG 300

CAGCTCAGCA GCCTGACATT TGAGGACTCT GCGGTCATTT TCTGTGCAAG

AGGGCATTAT TACGGTTACT TTGACTACTG GGGCCAAGGC ACCACTCTCA 400

CAGTCTCCTC AGCTAGCACC AAGGGCCCAT CGGTCTTCCC CCTGGCACCC

TCCTCCAAGA GCACCTCTGG GGGCACAGCG GCCCTGGGCT GCCTGGTCAA 500

GGACTACTTC CCCGAACCGG TGACGGTGTC GTGGAACTCA GGCGCCCTGA

CCAGCGGCGT GCACACCTTC CCGGCTGTCC TACAGTCCTC AGGACTCTAC 600

TCCCTCAGCA GCGTGGTGAC CGTGCCCTCC AGCAGCTTGG GCACCCAGAC

CTACATCTGC AACGTGAATC ACAAGCCCAG CAACACCAAG GTGGACAAGA 700

GAGTTGAGCC CAAATCTTGT GACAAAACTC ACACATGCCC ACCGTGCCCA

GCACCTGAAC TCCTGGGGGG ACCGTCAGTC TTCCTCTTCC CCCCAAAACC 800

CAAGGACACC CTCATGATCT CCCGGACCCC TGAGGTCACA TGCGTGGTGG

TGGACGTGAG CCACGAAGAC CCTGAGGTCA AGTTCAACTG GTATGTGGAC 900

GGCGTGGAGG TGCATAATGC CAAGACAAAG CCGCGGGAGG AGCAGTACCA

AAGCACGTAC CGTGTGGTCA GCGTCCTCAC CGTCCTGCAC CAAGACTGGC 1000

TGAATGGCAA GGAGTACAAG TGCAAGGTCT CCAACAAAGC CCTCCCAGCC

CCCATCGAGA AAACCATCTC CAAAGCCAAA GGGCAGCCCC GAGAACCACA 1100

GGTGTACACC CTGCCCCCAT CCCGGGAGGA GATGACCAAG AACCAAGTCA

GCCTGACCTG CCTGGTCAAA GGCTTCTATC CCAGCGACAT CGCCGTGGAG 1200

TGGGAGAGCA ATGGGCAGCC GGAGAACAAC TACAAGACCA CGCCTCCCGT
```

```
GCTGGACTCC GACGGCTCCT TCTTCCTCTA TTCCAAGCTC ACCGTGGACA 1300

AGAGCAGGTG GCAGCAGGGG AACGTCTTCT CATGCTCCGT GATGCATGAG

GCTCTGCACA ACCACTACAC GCAGAAGAGC CTCTCCCTGT CTCCGGGCTG 1400

A                                                    1401
```

Amino acid sequence of chimeric anti-sFlt-1 antibody AGB10 heavy chain SEQ ID NO:18. The variable chain (V$_H$) is indicated in bold (amino acids 1-118). The human IgG C$_H$1-C$_H$3 portion of the heavy chain spans amino acids 119-447. The N298Q mutation is underlined, bold, and cursive.

```
QVQLQQSGPE LVKPGASVKM SCKASGYTFT DYVISWVKQR

TGQGLEWIGE IYPGSGSIYY NEKFKGKATL TADTSSNTAY

MQLSSLTFED SAVIFCARGH YYGYFDYWGQ GTTLTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPELLGGPS

VFLFPPKPKD TLMISRTPEV TCVVVDVSHE DPEVKFNWYV

DGVEVHNAKT KPREEQYQST YRVVSVLTVL HQDWLNGKEY

KCKVSNKALP APIEKTISKA KGQPREPQVY TLPPSREEMT
```

Nucleotide sequence of chimeric anti-sFlt-1 antibody AGB10 light chain—SEQ ID NO:19. The leader sequence encoding the secretion signal peptide (19 amino acid residues, nucleotides 1-57) is underlined. The sequence encoding the variable chain (V$_L$) is indicated in bold (nucleotides 58-378). The human IgG kappa CL portion of the light chain spans nucleotides 379-699.

Amino acid sequence of chimeric anti-sFlt-1 antibody AGB10 light chain—SEQ ID NO:20. The variable chain (V$_L$) is indicated in bold (amino acids 1-107). The human IgG kappa CL portion of the light chain spans nucleotides 108-214.

```
DIVMTQSHKF MSTSVGDRVS ITCKASQDVT ITVAWYQQKP

GQSPKLLIYS ASYRYTGVPD RFTGSGSGTD FTFTISSVQA

EDLAVYYCQQ HYTTPWTFGG GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

Nucleotide sequence of chimeric anti-sEng antibody cENG10 heavy chain—SEQ ID NO:25. The leader sequence encoding the secretion signal peptide (19 amino acid residues, nucleotides 1-57) is underlined. The sequence encoding the variable chain (V$_H$) is indicated in bold (nucleotides 58-417). The human IgG C$_H$1-C$_H$3 portion of the heavy chain spans nucleotides 418-1404. The codon encoding the N300Q mutation is underlined, bold, and cursive.

```
ATGATGTCCT TTGTCTCTCT GCTCCTGGTA GGCATCCTAT TCCATGCCAC

CCAGGCCGAC ATTGTGATGA CCCAGTCTCA CAAATTCATG TCCACATCAG 100

TAGGAGACAG GGTCAGCATC ACCTGCAAGG CCAGTCAGGA TGTGACTATT

ACTGTAGCCT GGTATCAACA GAAACCAGGA CAATCTCCTA AACTTCTGAT 200

TTACTCGGCA TCCTACCGGT ACACTGGAGT CCCTGATCGC TTCACTGGCA

GTGGATCTGG GACGGATTTC ACTTTCACCA TCAGCAGTGT GCAGGCTGAA 300

GACCTGGCAG TTTATTACTG TCAGCAACAT TATACTACTC CGTGGACGTT

CGGTGGAGGC ACCAAGCTGG AAATCAAACG GACTGTGGCT GCACCATCTG 400

TCTTCATCTT CCCGCCATCT GATGAGCAGT TGAAATCTGG AACTGCCTCT

GTTGTGTGCC TGCTGAATAA CTTCTATCCC AGAGAGGCCA AAGTACAGTG 500

GAAGGTGGAT AACGCCCTCC AATCGGGTAA CTCCCAGGAG AGTGTCACAG

AGCAGGACAG CAAGGACAGC ACCTACAGCC TCAGCAGCAC CCTGACGCTG 600

AGCAAAGCAG ACTACGAGAA ACACAAAGTC TACGCCTGCG AAGTCACCCA

TCAGGGCCTG AGCTCGCCCG TCACAAAGAG CTTCAACAGG GGAGAGTGTT 700

AG                                                   702
```

ATGGGATGGT CATGTATCAT CCTTTTTCTA GTAGCAACTG CAACTGGAGT

ACATTCAGAG GTCCAGCTGG AACAGTCTGG ACCTGAAGTG GTGAAGCCTG 100

GGACTTCAGT GAAGATATCC TGCAAGACTT CTGGATACAC AATCACTGAA

CACACCTTGC ACTGGATAAA GCAGAACCAG GGAAAGAGCC TTGAGTGGAT 200

TGGTGGTATT AATTTTGACA ATGGTGGTAC TACCTACAGG CAGAAATTCA

AGGACAAGGC CACATTGACT GTGGACAAGT CCTCCAGCAC AGCCTTCATG 300

GAGCTCCGCA GCCTGACTTC TGATGATTCT GCAGTCTATT TCTGCGCAAG

AAGGGCCTAT TACTACGGTA GTGCCTTTGA CTACTGGGGC CAAGGCACCA 400

CTCTCACAGT CTCCTCAGCT AGCACCAAGG GCCCATCGGT CTTCCCCCTG

GCACCCTCCT CCAAGAGCAC CTCTGGGGGC ACAGCGGCCC TGGGCTGCCT 500

GGTCAAGGAC TACTTCCCCG AACCGGTGAC GGTGTCGTGG AACTCAGGCG

CCCTGACCAG CGGCGTGCAC ACCTTCCCGG CTGTCCTACA GTCCTCAGGA 600

CTCTACTCCC TCAGCAGCGT GGTGACCGTG CCCTCCAGCA GCTTGGGCAC

CCAGACCTAC ATCTGCAACG TGAATCACAA GCCCAGCAAC ACCAAGGTGG 700

ACAAGAGAGT TGAGCCCAAA TCTTGTGACA AAACTCACAC ATGCCCACCG

TGCCCAGCAC CTGAACTCCT GGGGGGACCG TCAGTCTTCC TCTTCCCCCC 800

AAAACCCAAG GACACCCTCA TGATCTCCCG GACCCCTGAG GTCACATGCG

TGGTGGTGGA CGTGAGCCAC GAAGACCCTG AGGTCAAGTT CAACTGGTAT 900

GTGGACGGCG TGGAGGTGCA TAATGCCAAG ACAAAGCCGC GGGAGGAGCA

GTACCAAAGC ACGTACCGTG TGGTCAGCGT CCTCACCGTC CTGCACCAAG 1000

ACTGGCTGAA TGGCAAGGAG TACAAGTGCA AGGTCTCCAA CAAAGCCCTC

CCAGCCCCCA TCGAGAAAAC CATCTCCAAA GCCAAAGGGC AGCCCCGAGA 1100

ACCACAGGTG TACACCCTGC CCCCATCCCG GGAGGAGATG ACCAAGAACC

AAGTCAGCCT GACCTGCCTG GTCAAAGGCT TCTATCCCAG CGACATCGCC 1200

GTGGAGTGGG AGAGCAATGG GCAGCCGGAG AACAACTACA AGACCACGCC

TCCCGTGCTG GACTCCGACG GCTCCTTCTT CCTCTATTCC AAGCTCACCG 1300

TGGACAAGAG CAGGTGGCAG CAGGGGAACG TCTTCTCATG CTCCGTGATG

CATGAGGCTC TGCACAACCA CTACACGCAG AAGAGCCTCT CCCTGTCTCC 1400

GGGCTGA 1407

Amino acid sequence of chimeric anti-sEng antibody cENG10 heavy chain SEQ ID NO:26. The variable chain ($V_H$) is indicated in bold (amino acids 1-120). The human IgG $C_H1$-$C_H3$ portion of the heavy chain spans amino acids 121-449. The N300Q mutation is underlined, bold, and cursive.

EVQLEQSGPE VVKPGTSVKI SCKTSGYTIT EHTLHWIKQN

QGKSLEWIGG INFDNGGTTY RQKFKDKATL TVDKSSSTAF

MELRSLTSDD SAVYFCARRA YYYGSAFDYW GQGTTLTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPELLGG

-continued

PSVFLFPPKP KDTLMISRTP EVTCVVVDVS HEDPEVKFNW

YVDGVEVHNA KTKPREEQYQ STYRVVSVLT VLHQDWLNGK

EYKCKVSNKA LPAPIEKTIS KAKGQPREPQ VYTLPPSREE

MTKNQVSLTC LVKGFYPSDI AVEWESNGQP ENNYKTTPPV

LDSDGSFFLY SKLTVDKSRW QQGNVFSCSV MHEALHNHYT

QKSLSLSPG

Nucleotide sequence of chimeric anti-sEng antibody cENG10 light chain—SEQ ID NO:27. The leader sequence encoding the secretion signal peptide (19 amino acid residues, nucleotides 1-57) is underlined. The sequence encoding the variable chain ($V_L$) is indicated in bold (nucleotides 58-375). The human IgG kappa CL portion of the light chain spans nucleotides 376-696.

```
ATGGGATGGT CATGTATCAT CCTTTTTCTA GTAGCAACTG CAACTGGAGT

ACATTCAGAA AATGTGCTCA CCCAGTCTCC AGCAATCATG TCTGCATCTC 100

TAGGGGAGAA GGTCACCATG ACCTGCAGGG CCAGCTCAAG TGTGAATTAC

GTGTACTGGT ACCAGCAGAA GTCAGATGCC TCCCCCAAAC TATGGATTTA 200

TTACACTTCC AACCTGGCTC CTGGAGTCCC AGCTCGCTTC AGTGGCAGTG

GGTCTGGGAA CTCTTATTCT CTCACAATCA GCAGCATGGA GGGTGAAGAT 300

GCTGCCACTT ATTACTGCCA GCAGTTTATT AGTTTCCCAT ACACGTTCGG

AGGGGGGACC AAGCTGGAAA TAAAACGGAC TGTGGCTGCA CCATCTGTCT 400

TCATCTTCCC GCCATCTGAT GAGCAGTTGA AATCTGGAAC TGCCTCTGTT

GTGTGCCTGC TGAATAACTT CTATCCCAGA GAGGCCAAAG TACAGTGGAA 500

GGTGGATAAC GCCCTCCAAT CGGGTAACTC CCAGGAGAGT GTCACAGAGC

AGGACAGCAA GGACAGCACC TACAGCCTCA GCAGCACCCT GACGCTGAGC 600

AAAGCAGACT ACGAGAAACA CAAAGTCTAC GCCTGCGAAG TCACCCATCA

GGGCCTGAGC TCGCCCGTCA CAAAGAGCTT CAACAGGGGA GAGTGTTAG 699
```

Amino acid sequence of chimeric anti-sEng antibody cENG10 light chain—SEQ ID NO:28. The variable chain ($V_L$) is indicated in bold (amino acids 1-106). The human IgG kappa CL portion of the light chain spans nucleotides 107-213.

```
ENVLTQSPAI MSASLGEKVT MTCRASSSVN YVYWYQQKSD

ASPKLWIYYT SNLAPGVPAR FSGSGSGNSY SLTISSMEGE

DAATYYCQQF ISFPYTFGGG TKLEIKRTVA APSVFIFPPS

DEQLKSGTAS VVCLLNNFYP REAKVQWKVD NALQSGNSQE

SVTEQDSKDS TYSLSSTLTL SKADYEKHKV YACEVTHQGL

SSPVTKSFNR GEC
```

Expression and Purification of AG10B

A Chinese Hamster Ovary (CHO) cell pool LC4/HC3 (or IG10_IgG1mut) containing multiple copies of integrated light chain (LC) and heavy chain (HC) of the chimeric AG10B gene sequences was produced using the Catalent Biologics GPEx technology.

The AG10B antibody used in this study was purified from supernatants of 8×1.4 L (total 11.2 L) of shake flask cultures of LC4/HC3 cells by Protein A chromatography, followed by flow-through Q anion-exchange chromatography step, viral inactivation by low-pH 3.51 hold for 30 min, and buffer-exchanged into phosphate buffer (10 mM Sodium phosphate+150 mM Sodium chloride, pH 7.4) at final concentration of 5.0 mg/mL (using E0.1% at A280=1.54) and final yield of 2.57 grams. The quality control analysis showed that purified AG10B was 98% monomer by size exclusion chromatography (SEC)-high performance liquid chromatography HPLC, very low or no bioburden and endotoxin levels (<0.05 EU/mg).

Expression and Purification of cENG10

Human embryonic kidney (HEK)-293F suspension-adapted cells or CHOZN GS −/− cells were transiently transfected with polyethylenimine (PEI) and pIRES bicistronic expression vector DNA containing the cENG10 Heavy Chain (HC) gene under the control of Cytomegalovirus (CMV) immediate early (IE) promoter, followed by an encephalomycocarditis virus (ECMV) internal ribosome entry site (IRES) and the cENG10 Light Chain (LC) gene. The secreted cENG10 antibody in the conditioned media was purified by Protein-A affinity chromatography and Ion-Exchange Chromatography.

Example 2: Spiked sEng Depletion by cENG10 Immunoabsorption Device

The performance of cENG10 device columns at 1 ml scale was evaluated using a range of apheresis parameters to be used in clinical settings, including flow rates (volumetric and linear) and residence (contact) times.

Volumetric Flow Rate

The effect of the flow rate on sEng depletion by antibody cENG10 conjugated to Sepharose matrix at a ratio of 0.2 mg antibody per ml beads was determined. This ratio which is approximately 5 fold lower than the antibody density to be used for the prototype of the dual Immunoabsorption device (see Examples 3 and 4). Anti-sFlt-1 antibody AG10B served as a negative control.

A 1-ml cENG10 device column was evaluated for depletion of spiked sEng in horse serum. For each column, 0.2 mg cENG10 or AG10B MAb was covalently conjugated to 1 mL of CNBr-activated Sepharose 4FF beads for 0.2 mg per mL beads ratio. For each test, 10 mL of serum containing 60 ng/mL of sEng, median concentration in severe pre-eclampsia patients, was applied for one cycle over the column. The first 1 ml containing pre-equilibration buffer was not collected in the flow-through (FT) fraction and the last 1 mL of input remaining in column was chased with 1 CV of PBS buffer and pooled into the FT fraction. The % sEng depletion was calculated by dividing the difference in concentration between input and FT by input concentration:

$$([sEng]_{input} - [sEng]_{FT}) / [sEng]_{input}$$

For flow rates<0.5 mL/min, no less than 92% of the spiked sEng protein were depleted by the cENG10 column (see Table 3). The sEng depletion by the cENG10 device was specific for all flow rates tested, as the control AG10B device does not deplete sEng significantly from the serum. Thus, at 1 mL scale, if the MAb density is 0.2 mg MAb to mL beads ratio or lower, the flow rate may be kept <0.5 mL/min. If the column volume were to be scaled up and the aspect ratio of the column kept constant, this would be equivalent to 25 mL plasma/min for a 50 mL column, the size of the prototype device to be used for patients (see Examples 3 and 4). For example, if a half body plasma volume (~2 L in pregnant women) is to be processed at flow rate equivalent to 0.5 mL/min at 1-mL scale, it would take ~80 min to complete treatment.

TABLE 3

| Effect of volumetric low rate on sEng depletion | | |
|---|---|---|
| Flow Rate (mL/min) | cENG10 Column | AG10B Column |
| 0.25 | 97% | 5% |
| 0.50 | 92% | 4% |
| 2.00 | 58% | 3% |

Linear Flow Rate

The linear flow rate takes the dimension of the packed column into consideration. Therefore, the effect of the linear flow rate on sEng depletion by the cENG10 column (density 0.2 mg MAb per mL beads) at 1 mL scale was determined.

A 1-mL cENG10 device column covalently conjugated with 0.2 mg of either cENG10 (anti-human sEng) or AG10B (anti-human sFlt-1) MAb was tested for depletion of sEng spiked in horse serum. For input, 10 mL of serum containing 60 ng/mL of sEng was applied for one cycle over the column. The flow-through fraction was collected as previously described. The % sEng depletion was calculated by dividing the difference in concentration between input and FT by input concentration:

$$([sEng]_{input}-[sEng]_{FT})/[sEng]_{input}$$

Under these conditions, effective depletion of sEng was achieved by using linear flow rates<18 cm/hour (or <0.3 cm/min), see Table 4. The control AG10B did not deplete sEng significantly as expected.

TABLE 4

| Effect of linear flow rate on sEng depletion | | |
|---|---|---|
| Linear Flow Rate (cm/h) | cENG10 Column | AG10B Column |
| 9 | 97% | 5% |
| 18 | 92% | 4% |
| 73 | 58% | 3% |

Residence Time

The residence (or column contact) time is an important parameter to consider in this mode of affinity-mediated apheresis treatment.

A 1-mL cENG10 device column covalently conjugated with 0.2 mg of either cENG10 (anti-human sEng) or AG10B (anti-human sFlt-1) MAb was tested for depletion of sEng spiked in horse serum and the flow-through fraction was collected as previously described. The % sEng depletion was calculated by dividing the difference in concentration between input and FT by input concentration:

$$([sEng]_{input}-[sEng]_{FT})/[sEng]_{input}$$

As shown in Table 5, at 1 mL scale, residence time of 2 min or greater lead to effective (>90%) sEng depletion. The control AG10B did not significantly deplete sEng even at all residence times tested up to 4 min.

TABLE 5

| Effect of residence (contact) time on sEng depletion | | |
|---|---|---|
| Residence Time (min) | cENG10 Column | AG10B Column |
| 0.5 | 58% | 3% |
| 2.0 | 92% | 4% |
| 4.0 | 97% | 5% |

Antibody to Beads Ratio (Density)

When antibodies are covalently conjugated using CNBr-activated beads, it is possible that only a subset of the antibodies is in orientations favorable for antigen capture. For instance, non-covalent conjugation of antibodies to Protein-G beads, which bind to the Fc region of the antibody, likely orients all antibodies in a similar way. On the other hand, covalent immobilization of the antibody on CNBr-activated beads likely results in conjugation of the antibodies at different accessible amine groups and therefore varying orientations.

The 1-mL cENG10 device column covalently conjugated with varying amounts of cENG10 (anti-human sEng) or 1 mg of AG10B (anti-human sFlt-1) MAb were tested for depletion of sEng in human plasma. The % sEng depletion (or similarly for % sFlt-1 depletion) was calculated by dividing the difference in concentration between input and FT by input concentration:

$$([sEng]_{input}-[sEng]_{FT})/[sEng]_{input}$$

As shown in Table 6, the use of >0.5 mg of cENG10 antibody per mL beads resulted in a depletion of >80% of the sEng spiked into human plasma. For subsequent device development, MAb density of 0.8 or 1 mg MAb per mL beads was used for conjugation.

TABLE 6

| Effect of antibody: bead ratio (density) on sEng depletion | | |
|---|---|---|
| MAb Density (mg/mL beads) | cENG10 Column | AG10B Column |
| 0.2 | 65% | Not tested |
| 0.5 | 82% | Not tested |
| 1.0 | 85% | 8% |
| 2.0 | 88% | Not tested |

Example 3: A Dual Immunoabsorption Column Comprising Anti-sFlt-1 and Anti-sEng Antibodies Effectively Removes sFlt-1 and sEng from Plasma Circulating sEng and sFlt-1 proteins are elevated in pre-eclampsia patients and are postulated to be major causal factors of disease onset and progression. To test whether a cENG10/AG10B dual device is capable of removing these endogenous sEng and sFlt-1 proteins from patient serum, micro-scale 0.1 mL columns conjugated with cENG10, AG10B, or both cENG10 and AG10B MAbs were prepared. cENG10 column specifically removed>90% of endogenous sEng in pre-eclamptic serum but not endogenous sFlt-1, and the AG10B column specifically removed>90% of endogenous sFlt-1 in pre-eclamptic serum but not endogenous sEng. The cENG10/AG10B dual device column, in which a mixture of the two antibodies at 1 mg each per mL beads were conjugated simultaneously, removed>90% of both sEng and sFlt-1 proteins. The control mock-conjugated column did not deplete either sEng or sFlt-1 (see Table 7).

TABLE 7

| Depletion of endogenous sEng and sFlt-1 depletions from patient serum | | |
|---|---|---|
| Column | % sEng Depleted | % sFlt-1 Depleted |
| cENG10 | 96% | 3% |
| AG10B | –3% | 95% |
| CENG10 + AG10B | 99% | 93% |
| Beads (negative control) | 0% | 0% |

Example 4: Development of a Full-Size 50-mL Dual Immunoabsorption Device

For apheresis treatment, a dual Immunoabsorption device column can be integrated into an apheresis instrument (exemplified in FIG. 1) that separates plasma from cell components, directs plasma through the dual device column, and after removing excess sEng and sFlt-1, recombines plasma with cells and returns treated blood to patient circulation.

Figure 2:
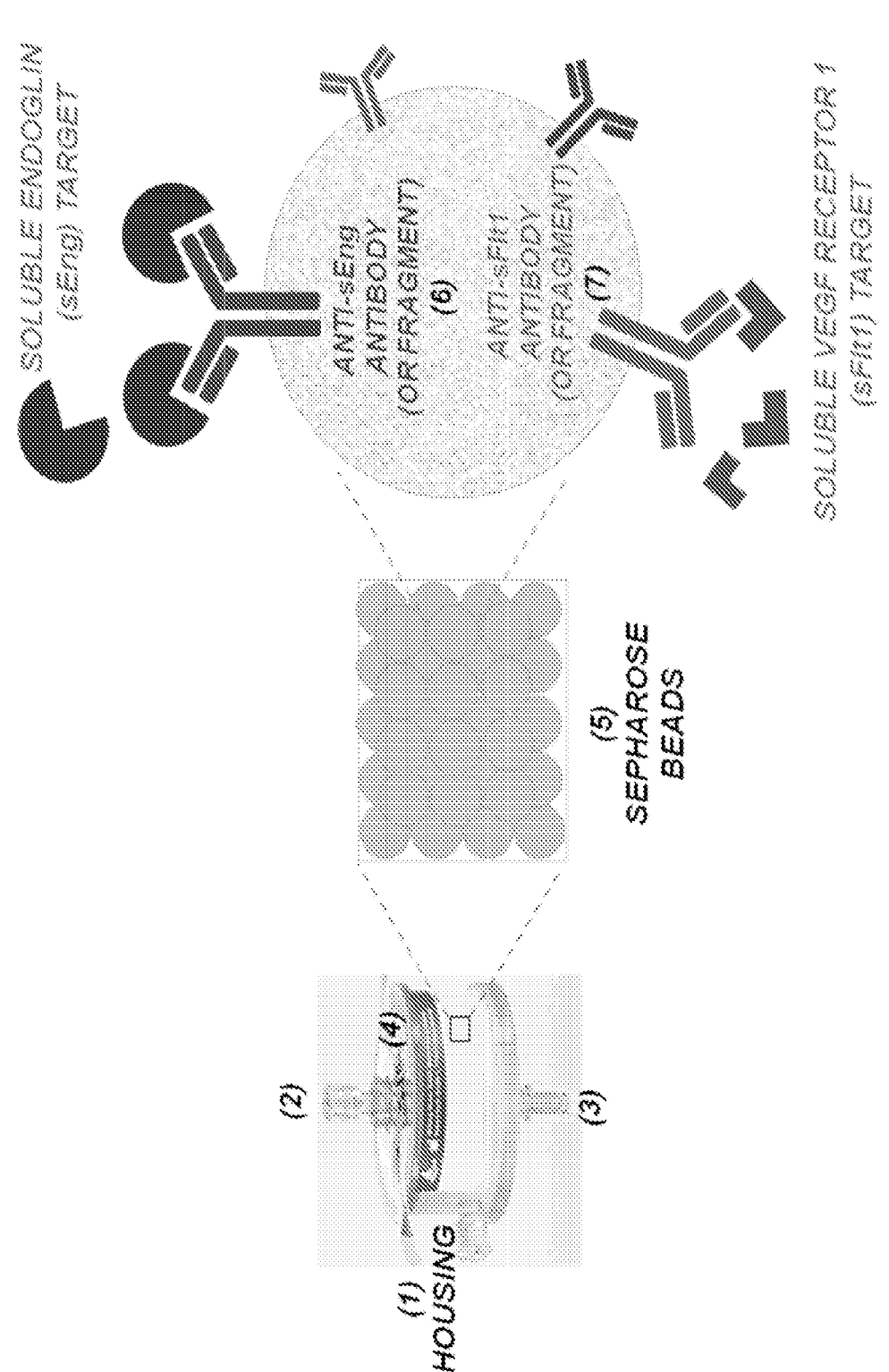
FIG. 2 shows one embodiment of a dual immunoadsorption device cartridge. The exemplified prototype cartridge is composed of the housing 1, inlet port at the top 2, outlet port at the bottom 3 and membrane filters 4 at the top and bottom of the housing. Plasma that is separated from cell components by an apheresis system flows into the inlet port 2 and through the inner compartment of the cartridge containing Sepharose beads 5 covalently conjugated with anti-sEng 6 and anti-sFlt-1 7 antibodies. These immobilized antibodies capture their respective targets sEng and sFlt-1 proteins as the plasma passes through the cartridge. The treated plasma then flows out of the cartridge through outlet port 3 and recombines with cells and back into patient circulation. 1, 2, 3, and 4 are made of blood compatible synthetic materials and are interconnected by conventional techniques.

FIG. 2 depicts the components of an exemplary 50-mL prototype dual Immunoabsorption device column. The housing (1) of the device cartridge contains membrane filters (4) above and below housing to prevent clogging and ports for inflow and outflow of plasma. The plasma separated from cell components enters the inflow port (2) and flows into and through the bed of Sepharose beads (5) inside the device cartridge. The Sepharose beads are conjugated with equal mixtures of anti-sEng chimeric cENG10 antibody (6) and anti-sFlt-1 chimeric AG10B antibody (7) that target and remove excess sEng and sFlt-1, respectively.

A full-size 50-mL prototype dual column was generated by conjugating 50 mg each of highly purified cENG10 and AG10B monoclonal antibodies to CNBr-activated Sepharose 4FF beads for ~1 h. After blocking with 0.1 M Tris-HCl pH 8.0, the beads were pre-equilibrated in PBS buffer. For depletion experiments, purified sEng (human Endoglin ectodomain residues 26 to 586 with C-terminal 6× His tag expressed in HEK-293F cells) and purified sFlt-1 domains 1 to 3 (N-terminal minimal domains sufficient to bind VEGF and PlGF ligands) were spiked into donated human or horse plasma at 60 ng/mL (sEng) and 40 ng/mL (sFlt-1), mean concentrations found in pre-eclampsia patient sera, and applied onto the prototype device at defined flow rates. After each 250 mL of the input plasma containing spiked sEng had been processed at residence time of 5 min, similar to clinical apheresis parameter range, aliquots of the flow-through fractions were collected and saved, up to 2 L of processed plasma. The amounts of sEng and sFlt-1 in input plasma and in the flow-through fractions, i.e. the target proteins not captured by the device, were measured by human Endoglin and VEGF R1 DuoSet ELISA assays, respectively.

Figure 3:
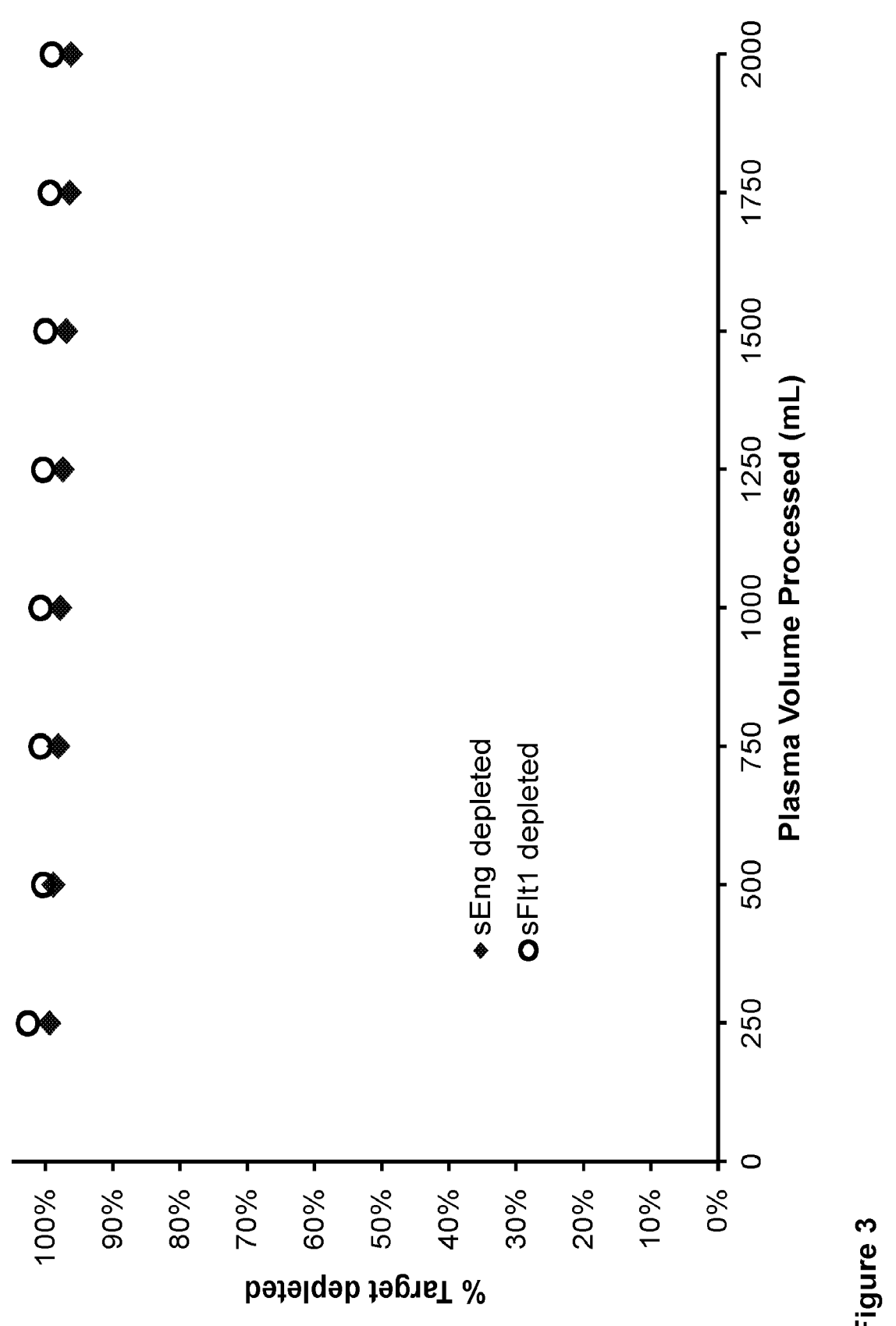
FIG. 3 illustrates the depletion of sEng and sFlt-1 proteins using a dual immunoadsorption device comprising both anti-sFlt-1 and anti-sEng antibodies. A full-size 50-mL prototype device contained Sepharose beads conjugated with 50 mg each of cENG10 and AG10B (for 1 mg monoclonal antibody (MAb) per mL beads coupling density) was used for this experiment. Horse serum containing 60 ng/mL of recombinant human sEng (amino acid residues 26-586) and 40 ng/mL of sFlt-1 (domains 1 to 3) was applied to the 50-mL prototype device column at a volumetric flow rate of 10 mL/min, which is equivalent to residence time of ~5 min.
Figure 4:
FIG. 4 illustrates the depletion of sEng and sFlt-1 proteins using a dual immunoadsorption device comprising both anti-sFlt-1 and anti-sEng antibodies. This 50-mL device was manufactured under sterile conditions and contained Sepharose beads conjugated with 50 mg each of cENG10 and AG10B (for 1 mg MAb per mL beads coupling density). Human plasma containing 60 ng/mL of recombinant human sEng (residues 26-586) and 40 ng/mL of sFlt-1 (domains 1 to 3) was applied to the 50-mL prototype device column at a volumetric flow rate of 10 mL/min, which is equivalent to residence time of ~5 min.

As shown in FIG. 3, the prototype dual immunoabsorption device removed>95% of both sEng and sFlt-1 targets from at least 2 L of spiked plasma. Similar results were obtained using a device produced under sterile conditions by a manufacturer using Sepharose 6C$_L$ (see FIG. 4). The latter device depleted 100% of both sEng and sFlt-1 for up to 2 L processed plasma.

What is claimed is:

1. A method of treating a pregnancy-related hypertensive disorder in a subject in need thereof, the method comprising providing ex vivo to the subject an anti-soluble Endoglin (sEng) antibody or sEng-binding fragment thereof and an anti-soluble fms-like tyrosine kinase 1 (sFlt-1) antibody or sFlt-1-binding fragment thereof, wherein the anti-sEng antibody or sEng-binding fragment thereof comprises a heavy chain variable region and a light chain variable region, wherein each of the heavy chain and the light chain variable regions comprises a CDR1, CDR2, and CDR3, and wherein:

the sequence of CDR1H comprises SEQ ID NO:7;
the sequence of CDR2H comprises SEQ ID NO:8;
the sequence of CDR3H comprises SEQ ID NO:9;
the sequence of CDR1L comprises SEQ ID NO:10;
the sequence of CDR2L comprises SEQ ID NO:11;
the sequence of CDR3L comprises SEQ ID NO:12; and wherein the anti-sFlt-1 antibody or sFlt-1-binding fragment thereof comprises a heavy chain variable region and a light chain variable region, wherein each of the heavy chain and the light chain variable regions comprises a CDR1, CDR2, and CDR3, and wherein:

the sequence of CDR1H comprises SEQ ID NO:1;
the sequence of CDR2H comprises SEQ ID NO:2;
the sequence of CDR3H comprises SEQ ID NO:3;
the sequence of CDR1L comprises SEQ ID NO:4;
the sequence of CDR2L comprises SEQ ID NO:5; and
the sequence of CDR3L comprises SEQ ID NO:6.

2. The method of claim 1, wherein:

(a) the heavy chain variable region of the anti-sEng antibody or sEng-binding fragment thereof comprises a sequence at least 85% identical to SEQ ID NO:22, wherein the light chain variable region of the anti-sEng antibody or sEng-binding fragment thereof comprises a sequence at least 85% identical to SEQ ID NO:24; and (b) the heavy chain variable region of the anti-sFlt-1 antibody or sFlt-1-binding fragment thereof comprises a sequence at least 85% identical to SEQ ID NO:14, and wherein the light chain variable region of the anti-sFlt-1 antibody or sFlt-1-binding fragment thereof comprises a sequence at least 85% identical to SEQ ID NO:16.

3. The method of claim 1, wherein:

(a) the heavy chain variable region of the anti-sEng antibody or sEng-binding fragment thereof comprises SEQ ID NO:22, wherein the light chain variable region of the anti-sEng antibody or sEng-binding fragment thereof comprises SEQ ID NO:24; and (b) the heavy chain variable region of the anti-sFlt-1 antibody or sFlt-1-binding fragment thereof comprises SEQ ID NO: 14, and wherein the light chain variable region of the anti-sFlt-1 antibody or sFlt-1-binding fragment thereof comprises SEQ ID NO:16.

4. The method of claim 1, wherein:

(a) the anti-sEng antibody or sEng-binding fragment thereof has a heavy chain comprising a sequence at least 85% identical to SEQ ID NO:26, wherein the anti-sEng antibody or sEng-binding fragment thereof has a light chain comprising a sequence at least 85% identical to SEQ ID NO:28; and (b) the anti-sFlt-1 antibody or sFlt-1-binding fragment thereof has a heavy chain comprising a sequence at least 85% identical to SEQ ID NO:18 and wherein the anti-sFlt-1 antibody or sFlt-1-binding fragment thereof has a light chain comprising a sequence at least 85% identical to SEQ ID NO: 20.

5. The method of claim 1, wherein:
(a) the anti-sEng antibody or sEng-binding fragment thereof has a heavy chain comprising SEQ ID NO: 26, wherein the anti-sEng antibody or sEng-binding fragment thereof has a light chain comprising SEQ ID NO:28; and
(b) the anti-sFlt-1 antibody or sFlt-1-binding fragment thereof has a heavy chain comprising SEQ ID NO: 18 and wherein the anti-sFlt-1 antibody or sFlt-1-binding fragment thereof has a light chain comprising SEQ ID NO:20.

6. The method of claim 1, wherein the pregnancy-related hypertensive disorder is eclampsia, pre-eclampsia, or HELLP syndrome.

7. The method of claim 6, wherein the pregnancy-related hypertensive disorder is pre-eclampsia.

8. The method of claim 6, wherein the pregnancy-related hypertensive disorder is HELLP syndrome.

9. The method of claim 1, wherein the subject is a pregnant human or a postpartum human.

10. The method of claim 9, wherein, the subject is a pregnant human.

11. The method of claim 1, wherein the anti-sEng antibody or sEng-binding fragment thereof and the anti-sFlt-1 antibody or sFlt-1-binding fragment thereof are bound to one or more solid supports.

12. The method of claim 11, wherein the support-bound anti-sEng antibody or sEng-binding fragment thereof and the support-bound anti-sFlt-1 antibody or sFlt-1-binding fragment thereof are bound to the same solid support.

13. The method of claim 11, wherein the support-bound sEng antibody or sEng-binding fragment thereof and the support-bound anti-sFlt-1 antibody or sFlt-1-binding fragment thereof are bound to different solid supports.

14. The method of claim 1, the method comprising:
(a) removing blood from the subject,
(b) passing the blood or a component thereof over one or more solid supports to which are bound anti-sEng antibodies or sEng-binding fragments thereof and anti-sFlt-1 antibodies or sFlt-1-binding fragments thereof, to decrease the levels of sEng and sFlt-1 in the blood or component thereof, and
(c) returning the blood or component thereof to the subject's body.

15. The method of claim 14, wherein the blood or a component thereof comprises plasma and the method comprises removing a volume of the subject's blood and separating the blood into plasma and cellular components and passing the plasma over the one or more solid supports.

16. The method of claim 14, wherein the support-bound anti-sEng antibody or sEng-binding fragment thereof and the support-bound anti-sFlt-1 antibody or sFlt-1-binding fragment thereof are provided in a single column.

17. The method of claim 14, wherein the support-bound anti-sEng antibody or sEng-binding fragment thereof is provided in a first column and the support-bound anti-sFlt-1 antibody or sFlt-1-binding fragment thereof is provided in a second column.

18. An immunoadsorption device comprising:
(a) the anti-sEng antibody or sEng-binding fragment thereof of claim 1 and the anti-sFlt-1 antibody or sFlt-1-binding fragment thereof of claim 1, wherein the anti-sEng antibody or sEng-binding fragment thereof and the anti-sFlt-1 antibody or sFlt-1-binding fragment thereof are bound to one or more solid supports;

82

(b) a first means for conveying blood or a component thereof from a subject to the anti-sEng antibody or sEng-binding fragment thereof and anti-sFlt-1 antibody or sFlt-1-binding fragment thereof bound to the one or more solid supports so as to contact the blood or a component thereof with the anti-sEng antibody or sEng-binding fragment thereof and the anti-sFlt-1 antibody or sFlt-1-binding fragment thereof and thereby to remove sEng and sFlt-1 from the blood or a component thereof, wherein the first means comprises: (i) an access device, inserted into a blood vessel of the subject, for accessing the subject's blood system; and (ii) a conduit system, which fluidly connects the access device to the anti-sEng antibody or sEng-binding fragment thereof and the anti-sFlt-1 antibody or sFlt-1-binding fragment thereof, bound to the one or solid supports, thereby allowing the subject's blood or a component thereof to flow to and contact the anti-sEng antibody or sEng-binding fragment thereof and the anti-sFlt-1 antibody or sFlt-1-binding fragment thereof; and
a second means for conveying the blood or a component thereof to the subject following contact of the blood or a component thereof with the anti-sEng antibody or sEng-binding fragment thereof and the anti-sFlt-1 antibody or sFlt-1-binding fragment thereof, wherein the second means comprises: (i) a conduit system; and (ii) a return device, where the return device is inserted into a blood vessel of the subject, and where the conduit system fluidly connects the blood or a component thereof in contact with the anti-sEng antibody or sEng-binding fragment thereof and the anti-sFlt-1 antibody or sFlt-1-binding fragment thereof, to the return device so as to allow for the return of the blood or a component thereof to the subject.

19. The immunoadsorption device of claim 18, wherein the first means comprises a device for separating the subject's blood into plasma and cellular components.

20. The immunoadsorption device of claim 19, wherein the device for separating the subject's blood into plasma and cellular components is a centrifuge or an apheresis device.

21. The immunoadsorption device of claim 18, wherein the support-bound anti-sEng antibody or sEng-binding fragment thereof and the support-bound anti-sFlt-1 antibody or sFlt-1-binding fragment thereof are bound to the same solid support.

22. The immunoadsorption device of claim 18, wherein the support-bound anti-sEng antibody or sEng-binding fragment thereof and the support-bound anti-sFlt-1 antibody or sFlt-1-binding fragment thereof are bound to different solid supports.

23. A column comprising:
(a) the anti-sEng antibody or sEng-binding fragment thereof of claim 1; and
(b) the anti-sFlt-1 antibody or sFlt-1-binding fragment thereof of claim 1;
wherein the anti-sEng antibody or sEng-binding fragment thereof and the anti-sFlt-1 antibody or sFlt-1-binding fragment thereof are bound to a solid support.

24. The column of claim 23, wherein the support-bound anti-sEng antibody or sEng-binding fragment thereof and the support-bound anti-sFlt-1 antibody or sFlt-1-binding fragment thereof are bound to the same solid support.

25. A combination comprising:
(a) a first column comprising the anti-sEng antibody or sEng-binding fragment thereof of claim 1; and (b) a second column comprising the anti-sFlt-1 antibody
   or sFlt-1-binding fragment thereof of claim 1.

\*    \*    \*    \*    \*